US010640556B2

(12) United States Patent
Yarden et al.

(10) Patent No.: US 10,640,556 B2
(45) Date of Patent: May 5, 2020

(54) ANTI AMPHIREGULIN ANTIBODIES, COMPOSITIONS COMPRISING SAME AND USES THEREOF

(71) Applicant: Yeda Research and Development Co. Ltd., Rehovot (IL)

(72) Inventors: Yosef Yarden, Rehovot (IL); Silvia Carvalho, Rehovot (IL); Moshit Lindzen, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 16/044,636

(22) Filed: Jul. 25, 2018

(65) Prior Publication Data

US 2018/0327488 A1 Nov. 15, 2018

Related U.S. Application Data

(60) Division of application No. 15/271,515, filed on Sep. 21, 2016, now abandoned, which is a continuation-in-part of application No. PCT/IL2016/050299, filed on Mar. 17, 2016.

(30) Foreign Application Priority Data

Mar. 19, 2015 (IL) .......................................... 237852

(51) Int. Cl.
| | | |
|---|---|---|
| *C07K 16/22* | (2006.01) | |
| *A61K 39/00* | (2006.01) | |
| *A61K 31/704* | (2006.01) | |
| *A61K 33/24* | (2019.01) | |
| *G01N 33/574* | (2006.01) | |
| *A61K 45/06* | (2006.01) | |

(52) U.S. Cl.
CPC ............ *C07K 16/22* (2013.01); *A61K 31/704* (2013.01); *A61K 33/24* (2013.01); *A61K 45/06* (2013.01); *G01N 33/57407* (2013.01); *G01N 33/57449* (2013.01); *A61K 2039/505* (2013.01); *C07K 2317/24* (2013.01); *C07K 2317/565* (2013.01); *G01N 33/57438* (2013.01); *G01N 2333/485* (2013.01); *G01N 2333/495* (2013.01); *G01N 2800/52* (2013.01)

(58) Field of Classification Search
None
See application file for complete search history.

(56) References Cited

U.S. PATENT DOCUMENTS

| | | |
|---|---|---|
| 2004/0210040 A1 | 10/2004 | Landolfi et al. |
| 2006/0246448 A1 | 11/2006 | Ullrich et al. |
| 2010/0111965 A1 | 5/2010 | Johnston et al. |
| 2017/0002068 A1 | 1/2017 | Yarden et al. |

FOREIGN PATENT DOCUMENTS

| | | |
|---|---|---|
| EP | 1449538 | 8/2004 |
| WO | WO 2004/068931 | 8/2004 |
| WO | WO 2008/044068 | 4/2008 |
| WO | WO 2009/127881 | 10/2009 |
| WO | WO 2011/132182 | 10/2011 |
| WO | WO 2016/147194 | 9/2016 |

OTHER PUBLICATIONS

Communication Under Rule 164(2)(a) EPC dated Sep. 20, 2018 From the European Patent Office Re. Application No. 16715905.2. (4 Pages).
Communication Pursuant to Rule 164(2)(b) and Article 94(3) EPC dated Sep. 20, 2018 From the European Patent Office Re. Application No. 16715905.2. (6 Pages).
Communication Relating to the Results of the Partial International Search dated Jun. 24, 2016 From the International Searching Authority Re. Application No. PCT/IL2016/050299.
International Preliminary Report on Patentability dated Sep. 28, 2017 From the International Bureau of WIPO Re. Application No. PCT/IL2016/050299. (11 Pages).
International Search Report and the Written Opinion dated Aug. 29, 2016 From the International Searching Authority Re. Application No. PCT/IL2016/050299.
Office Action dated Mar. 19, 2018 From the Israel Patent Office Re. Application No. 237852 and Its Translation Into English. (6 Pages).
Official Action dated May 1, 2018 From the US Patent and Trademark Office Re. U.S. Appl. No. 15/271,515. (21 pages).
Official Action dated Sep. 13, 2017 From the US Patent and Trademark Office Re. U.S. Appl. No. 15/271,515. (11 pages).
Alinari et al. "Combination Anti-CD74 (Milatuzumab) and Anti-CD20 (Rituximab) Monoclonal Antibody Therapy Has In Vitro and In Vivo Activity in Mantle Cell Lymphoma", Blood, 117(17): 4530-4541, Published Online Jan. 12, 2011.
Eckstein et al. "Epidermal Growth Factor Receptor Pathway Analysis Identifies Amphiregulin as a Key Factor for Cisplatin Resistance of Human Breast Cancer Cells", The Journal of Biological Chemistry, XP055280410, 283(2): 739-750, Jan. 11, 2008.
Hrabovska et al. "A Novel System for the Efficient Generation of Antibodies Following Immunization of Unique Knockout Mouse Strains", PLoS ONE, 5(9): e12892-1-e12892-7, Sep. 23, 2010.

(Continued)

*Primary Examiner* — Marianne P Allen

(57) ABSTRACT

A method of determining the suitability of a subject to a treatment with an anti-amphiregulin antibody, wherein the subject has a cancer selected from the group consisting of ovarian cancer, head and neck cancer and pancreatic cancer exhibiting resistance to chemotherapy, is provided. The method comprising analyzing in a biological sample of the subject expression level of amphiregulin, transforming growth factor alpha (TGF-alpha) and heparin-binding epidermal growth factor (HB-EGF), wherein a level of expression of the amphiregulin above a predetermined threshold and no expression of the TGF-alpha and/or the HB-EGF or an expression below a predetermined level of the TGF-alpha and/or the HB-EGF is indicative of the suitability of the subject to treatment with the anti-amphiregulin antibody. Methods for treating cancer are also provided, as well as antibodies and pharmaceutical compositions.

9 Claims, 27 Drawing Sheets
(22 of 27 Drawing Sheet(s) Filed in Color)
Specification includes a Sequence Listing.

(56) References Cited

OTHER PUBLICATIONS

Pliarchopoulou et al. "Epithelial Ovarian Cancer: Focus on Targeted Therapy", Critical Reviews in Oncology/Hematology 79: 17-23, 2011.
Roberts et al. "Identification of Genes Associated with Platinum Drug Sensitivity and Resistance in Human Ovarian Cancer Cells", British Journal of Cancer, 92: 1149-1158, 2005.
So et al. "Amphiregulin Induces Human Ovarian Cancer Cell Invasion by Down-Regulating E-Cadherin Expression", FEBS Letters, 588(21): 3998-4007, Available Online Sep. 23, 2014.
Yotsumoto et al. "Amphiregulin Regulates the Activation of ERK and Akt Through Epidermal Growth Factor Receptor and HER3 Signals Involved in the Progression of Pancreatic Cancer", Cancer Science, XP055226799, 101(11): 2351-2360, Published Online Aug. 17, 2010. Abstract, p. 2352, col. 1, Para 1, Fig.1a.

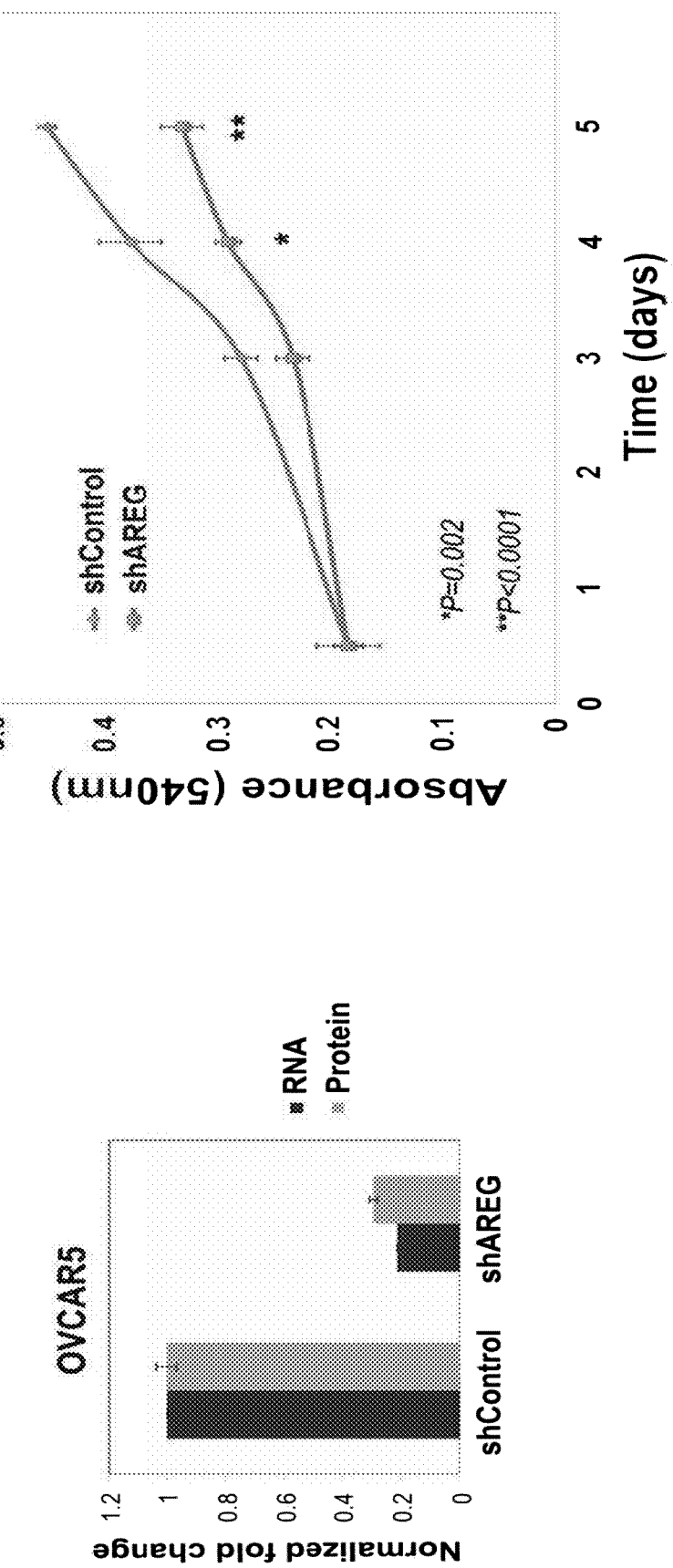

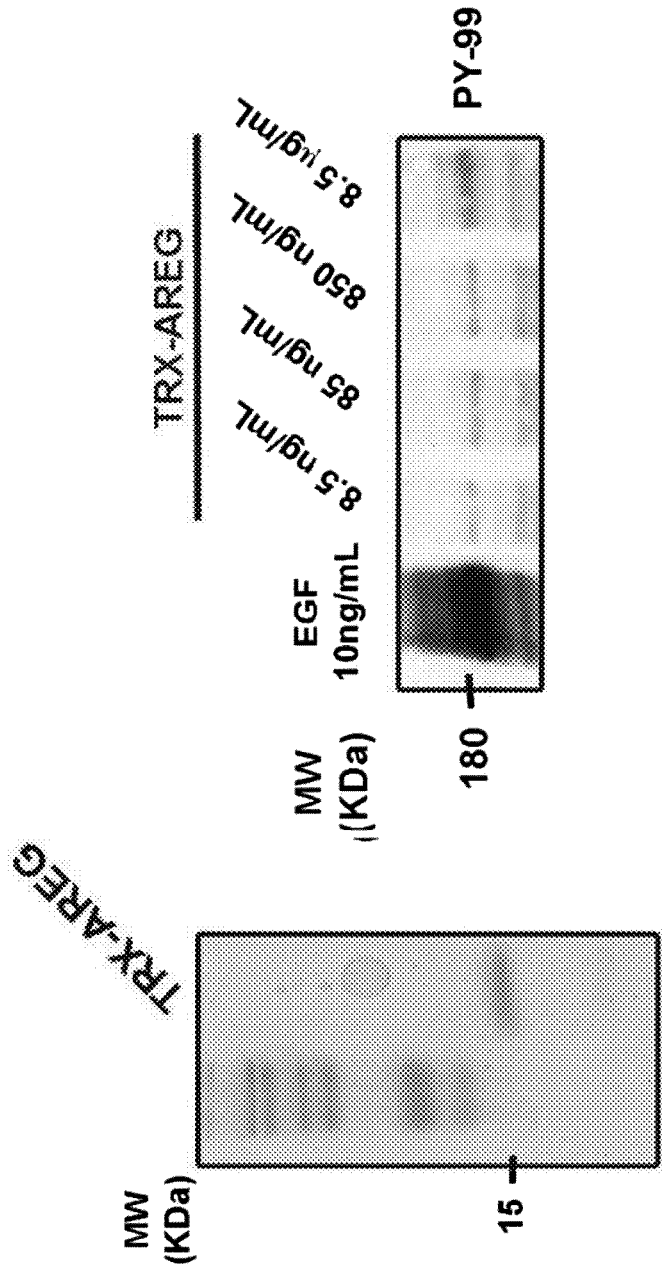

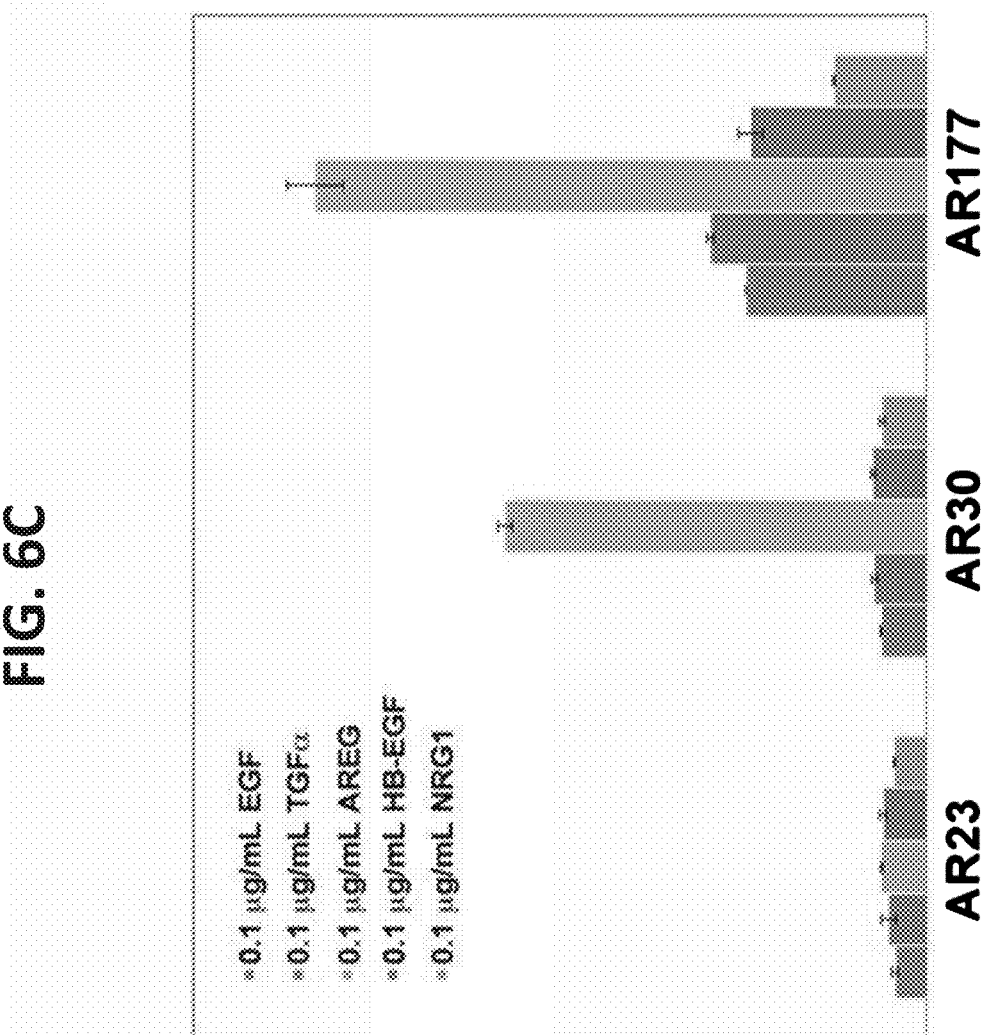

SEQUENCE LISTING

<160> NUMBER OF SEQ ID NOS: 104

<210> SEQ ID NO 1
<211> LENGTH: 360
<212> TYPE: DNA
<213> ORGANISM: Artificial sequence
<220> FEATURE:
<223> OTHER INFORMATION: AR30 heavy chain (IgG) complete nucleotide coding sequence

<400> SEQUENCE: 1

```
gaggttcagc tgcagcagtc tggggcagag cttgtgaggt caggggcctc agtcaagttg      60
tcctgcacag cttctggctt caacattaaa gactcctata tgcactgggt gaaacagagg     120
cctgaacagg gcctggagtg gattggatgg gttgatcctg ataatggtga tactgaatat     180
gccccggagt tccagggcag ggccactctg actgcagaca cattctccag cacagcctac     240
ctgcagctca ccagcctgac atctgaggac actgccgtct attactgtaa tgccccatct     300
acctatggtc actacggttt tgcttactgg ggccaaggaa ctctggtcac tgtctctgca     360
```

<210> SEQ ID NO 2
<211> LENGTH: 120
<212> TYPE: PRT
<213> ORGANISM: Artificial sequence
<220> FEATURE:
<223> OTHER INFORMATION: AR30 heavy chain (IgG) complete amino acids coding sequence

<400> SEQUENCE: 2

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Ser
            20                  25                  30

Tyr Met His Trp Val Lys Gln Arg Pro Glu Gln Gly Leu Glu Trp Ile
        35                  40                  45

Gly Trp Val Asp Pro Asp Asn Gly Asp Thr Glu Tyr Ala Pro Glu Phe
    50                  55                  60

Gln Gly Arg Ala Thr Leu Thr Ala Asp Thr Phe Ser Ser Thr Ala Tyr
65                  70                  75                  80

Leu Gln Leu Thr Ser Leu Thr Ser Glu Asp Thr Ala Val Tyr Tyr Cys
                85                  90                  95

Asn Ala Pro Ser Thr Tyr Gly His Tyr Gly Phe Ala Tyr Trp Gly Gln
            100                 105                 110

Gly Thr Leu Val Thr Val Ser Ala
        115                 120

<210> SEQ ID NO 3
<211> LENGTH: 24
<212> TYPE: DNA
<213> ORGANISM: Artificial sequence
<220> FEATURE:
<223> OTHER INFORMATION: AR30 heavy chain CDR1 nucleotide coding sequence

<400> SEQUENCE: 3

```
ggcttcaaca ttaaagactc ctat                                             24
```

<210> SEQ ID NO 4
<211> LENGTH: 8
<212> TYPE: PRT
<213> ORGANISM: Artificial sequence
<220> FEATURE:

```
<223> OTHER INFORMATION: AR30 heavy chain CDR1 amino acids coding
      sequence

<400> SEQUENCE: 4

Gly Phe Asn Ile Lys Asp Ser Tyr
1               5

<210> SEQ ID NO 5
<211> LENGTH: 24
<212> TYPE: DNA
<213> ORGANISM: Artificial sequence
<220> FEATURE:
<223> OTHER INFORMATION: AR30 heavy chain CDR2 nucleotide coding
      sequence

<400> SEQUENCE: 5
gttgatcctg ataatggtga tact                                          24

<210> SEQ ID NO 6
<211> LENGTH: 8
<212> TYPE: PRT
<213> ORGANISM: Artificial sequence
<220> FEATURE:
<223> OTHER INFORMATION: AR30 heavy chain CDR2 amino acids coding
      sequence

<400> SEQUENCE: 6

Val Asp Pro Asp Asn Gly Asp Thr
1               5

<210> SEQ ID NO 7
<211> LENGTH: 39
<212> TYPE: DNA
<213> ORGANISM: Artificial sequence
<220> FEATURE:
<223> OTHER INFORMATION: AR30 heavy chain CDR3 nucleotide coding
      sequence

<400> SEQUENCE: 7
aatgccccat ctacctatgg tcactacggt tttgcttac                           39

<210> SEQ ID NO 8
<211> LENGTH: 13
<212> TYPE: PRT
<213> ORGANISM: Artificial sequence
<220> FEATURE:
<223> OTHER INFORMATION: AR30 heavy chain CDR3 amino acids coding
      sequence

<400> SEQUENCE: 8

Asn Ala Pro Ser Thr Tyr Gly His Tyr Gly Phe Ala Tyr
1               5                   10

<210> SEQ ID NO 9
<211> LENGTH: 75
<212> TYPE: DNA
<213> ORGANISM: Artificial sequence
<220> FEATURE:
<223> OTHER INFORMATION: AR30 heavy chain FRM1 nucleotide coding
      sequence

<400> SEQUENCE: 9
gaggttcagc tgcagcagtc tggggcagag cttgtgaggt caggggcctc agtcaagttg    60
tcctgcacag cttct                                                    75

<210> SEQ ID NO 10
```

```
<211> LENGTH: 25
<212> TYPE: PRT
<213> ORGANISM: Artificial sequence
<220> FEATURE:
<223> OTHER INFORMATION: AR30 heavy chain FRM1 amino acids coding
      sequence

<400> SEQUENCE: 10

Glu Val Gln Leu Gln Gln Ser Gly Ala Glu Leu Val Arg Ser Gly Ala
1               5                   10                  15

Ser Val Lys Leu Ser Cys Thr Ala Ser
            20                  25

<210> SEQ ID NO 11
<211> LENGTH: 51
<212> TYPE: DNA
<213> ORGANISM: Artificial sequence
<220> FEATURE:
<223> OTHER INFORMATION: AR30 heavy chain FRM2 nucleotide coding
      sequence

<400> SEQUENCE: 11
atgcactggg tgaaacagag gcctgaacag ggcctggagt ggattggatg g         51

<210> SEQ ID NO 12
<211> LENGTH: 17
<212> TYPE: PRT
<213> ORGANISM: Artificial sequence
<220> FEATURE:
<223> OTHER INFORMATION: AR30 heavy chain FRM2 amino acids coding
      sequence

<400> SEQUENCE: 12

Met His Trp Val Lys Gln Arg Pro Glu Gln Gly Leu Glu Trp Ile Gly
1               5                   10                  15

Trp

<210> SEQ ID NO 13
<211> LENGTH: 114
<212> TYPE: PRT
<213> ORGANISM: Artificial sequence
<220> FEATURE:
<223> OTHER INFORMATION: AR30 heavy chain FRM3 nucleotide coding
      sequence

<400> SEQUENCE: 13

Gly Ala Ala Thr Ala Thr Gly Cys Cys Cys Gly Gly Ala Gly Thr
1               5                   10                  15

Thr Cys Cys Ala Gly Gly Gly Cys Ala Gly Gly Gly Cys Ala Cys
            20                  25                  30

Thr Cys Thr Gly Ala Cys Thr Gly Cys Ala Gly Ala Cys Ala Cys Ala
            35                  40                  45

Thr Thr Cys Thr Cys Cys Ala Gly Cys Ala Cys Ala Gly Cys Cys Thr
            50                  55                  60

Ala Cys Cys Thr Gly Cys Ala Gly Cys Thr Cys Ala Cys Cys Ala Gly
65                  70                  75                  80

Cys Cys Thr Gly Ala Cys Ala Thr Cys Thr Gly Ala Gly Gly Ala Cys
                    85                  90                  95

Ala Cys Thr Gly Cys Cys Gly Thr Cys Thr Ala Thr Ala Cys Thr
                100                 105                 110

Gly Thr
```

```
<210> SEQ ID NO 14
<211> LENGTH: 26
<212> TYPE: DNA
<213> ORGANISM: Artificial sequence
<220> FEATURE:
<223> OTHER INFORMATION: AR30 heavy chain FRM3 amino acids coding
      sequence

<400> SEQUENCE: 14
yagrattadt sstaytststsd tavyyc                                        26

<210> SEQ ID NO 15
<211> LENGTH: 339
<212> TYPE: DNA
<213> ORGANISM: Artificial sequence
<220> FEATURE:
<223> OTHER INFORMATION: AR30 light chain (kappa) complete nucleotide
      coding sequence

<400> SEQUENCE: 15
gatattgtga tgacccaggc tgcaccctct gtacctgtca ctcctggaga gtcagtatcc      60
atctcctgca ggtctagtaa gagtctcctg catagtaatg gcaaagctta cttgtattgg    120
ttcctgcaga ggccgggcca gtctcctcag ctcctaatat atcggatgtc aaccttgcc     180 tcaggagtcc cagacaggtt cagtggcagt gggtcgggaa ctgcttttac actgagaatc    240
agtagagtgg aggctgagga tgtgggtgtt tattactgta tgcaacatct agaatatccg    300
ctcacgttcg gtgctggcac aaagctcgag ctaaaacgt                           339

<210> SEQ ID NO 16
<211> LENGTH: 113
<212> TYPE: PRT
<213> ORGANISM: Artificial sequence
<220> FEATURE:
<223> OTHER INFORMATION: AR30 light chain (kappa) complete amino acids
      coding sequence

<400> SEQUENCE: 16

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Lys Ala Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

Arg

<210> SEQ ID NO 17
<211> LENGTH: 33
<212> TYPE: DNA
<213> ORGANISM: Artificial sequence
<220> FEATURE:
<223> OTHER INFORMATION: AR30 light chain CDR1 nucleotide coding
      sequence

<400> SEQUENCE: 17
```

```
aagagtctcc tgcatagtaa tggcaaagct tac                                    33
```

```
<210> SEQ ID NO 18
<211> LENGTH: 11
<212> TYPE: PRT
<213> ORGANISM: Artificial sequence
<220> FEATURE:
<223> OTHER INFORMATION: AR30 light chain CDR1 amino acids coding
      sequence

<400> SEQUENCE: 18

Lys Ser Leu Leu His Ser Asn Gly Lys Ala Tyr
1               5                   10
```

```
<210> SEQ ID NO 19
<211> LENGTH: 9
<212> TYPE: DNA
<213> ORGANISM: Artificial sequence
<220> FEATURE:
<223> OTHER INFORMATION: AR30 light chain CDR2 nucleotide coding
      sequence

<400> SEQUENCE: 19 cggatgtcc                                                                9
```

```
<210> SEQ ID NO 20
<211> LENGTH: 3
<212> TYPE: PRT
<213> ORGANISM: Artificial sequence
<220> FEATURE:
<223> OTHER INFORMATION: AR30 light chain CDR2 amino acids coding
      sequence

<400> SEQUENCE: 20

Arg Met Ser
1
```

```
<210> SEQ ID NO 21
<211> LENGTH: 27
<212> TYPE: DNA
<213> ORGANISM: Artificial sequence
<220> FEATURE:
<223> OTHER INFORMATION: AR30 light chain CDR3 nucleotide coding
      sequence

<400> SEQUENCE: 21
atgcaacatc tagaatatcc gctcacg                                           27
```

```
<210> SEQ ID NO 22
<211> LENGTH: 9
<212> TYPE: PRT
<213> ORGANISM: Artificial sequence
<220> FEATURE:
<223> OTHER INFORMATION: AR30 light chain CDR3 amino acids coding
      sequence

<400> SEQUENCE: 22

Met Gln His Leu Glu Tyr Pro Leu Thr
1               5
```

```
<210> SEQ ID NO 23
<211> LENGTH: 78
<212> TYPE: DNA
<213> ORGANISM: Artificial sequence
<220> FEATURE:
<223> OTHER INFORMATION: AR30 light chain FRM1 nucleotide coding
      sequence
```

-continued

<400> SEQUENCE: 23
gatattgtga tgacccaggc tgcaccctct gtacctgtca ctcctggaga gtcagtatcc    60
atctcctgca ggtctagt                                                 78

<210> SEQ ID NO 24
<211> LENGTH: 26
<212> TYPE: PRT
<213> ORGANISM: Artificial sequence
<220> FEATURE:
<223> OTHER INFORMATION: AR30 light chain FRM1 amino acids coding
      sequence

<400> SEQUENCE: 24

Asp Ile Val Met Thr Gln Ala Ala Pro Ser Val Pro Val Thr Pro Gly
1               5                   10                  15

Glu Ser Val Ser Ile Ser Cys Arg Ser Ser
            20                  25

<210> SEQ ID NO 25
<211> LENGTH: 51
<212> TYPE: DNA
<213> ORGANISM: Artificial sequence
<220> FEATURE:
<223> OTHER INFORMATION: AR30 light chain FRM2 nucleotide coding
      sequence

<400> SEQUENCE: 25
ttgtattggt tcctgcagag gccgggccag tctcctcagc tcctaatata t              51

<210> SEQ ID NO 26
<211> LENGTH: 17
<212> TYPE: PRT
<213> ORGANISM: Artificial sequence
<220> FEATURE:
<223> OTHER INFORMATION: AR30 light chain FRM2 amino acids coding
      sequence

<400> SEQUENCE: 26

Leu Tyr Trp Phe Leu Gln Arg Pro Gly Gln Ser Pro Gln Leu Leu Ile
1               5                   10                  15

Tyr

<210> SEQ ID NO 27
<211> LENGTH: 108
<212> TYPE: DNA
<213> ORGANISM: Artificial sequence
<220> FEATURE:
<223> OTHER INFORMATION: AR30 light chain FRM3 nucleotide coding
      sequence

<400> SEQUENCE: 27
aaccttgcct caggagtccc agacaggttc agtggcagtg gtcgggaac tgcttttaca    60 ctgagaatca gtagagtgga ggctgaggat gtgggtgttt attactgt               108

<210> SEQ ID NO 28
<211> LENGTH: 36
<212> TYPE: PRT
<213> ORGANISM: Artificial sequence
<220> FEATURE:
<223> OTHER INFORMATION: AR30 light chain FRM3 amino acids coding
      sequence

<400> SEQUENCE: 28

```
Asn Leu Ala Ser Gly Val Pro Asp Arg Phe Ser Gly Ser Gly Ser Gly
 1               5                  10                  15

Thr Ala Phe Thr Leu Arg Ile Ser Arg Val Glu Ala Glu Asp Val Gly
                20                  25                  30

Val Tyr Tyr Cys
            35
```

<210> SEQ ID NO 29
<211> LENGTH: 369
<212> TYPE: DNA
<213> ORGANISM: Artificial sequence
<220> FEATURE:
<223> OTHER INFORMATION: AR558 heavy chain (IgG) complete nucleotide coding sequence
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 29

```
caggtccngc tgcagcagtc tggggcagaa cttgtgaagc cnggggcctc agtcaagttg      60
tcctgcacag cttctggctt caacattaaa gacacctata tgcactgggt gaaacagagg     120
cctgaacagg gcctggagtg gattggaagg attgatcctg cgaatcgtag tactaaatat     180
gaccccgaagt tccagggcaa ggccactata acagcagaca catcctccaa cacagccgac     240
ctgcacctca gcagcctgac atctgaggac actgccgtct attactgtgc tagactttat     300
ggtgactccg tctggtactt cgatgtctgg ggcgcaggga ccacggtcac cgtctcctca     360
gccaaaacg                                                             369
```

<210> SEQ ID NO 30
<211> LENGTH: 123
<212> TYPE: PRT
<213> ORGANISM: Artificial sequence
<220> FEATURE:
<223> OTHER INFORMATION: AR558 heavy chain IgG complete amino acids coding sequence

<400> SEQUENCE: 30

```
Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Arg Ser Thr Lys Tyr Asp Pro Lys Phe
        50                  55                  60

Gln Gly Lys Ala Thr Ile Thr Ala Asp Thr Ser Ser Asn Thr Ala Asp
 65                  70                  75                  80

Leu His Leu Ser Ser Leu Thr Ser Glu Asp Thr Ala Val Tyr Tyr Cys
                85                  90                  95

Ala Arg Leu Tyr Gly Asp Ser Val Trp Tyr Phe Asp Val Trp Gly Ala
            100                 105                 110

Gly Thr Thr Val Thr Val Ser Ser Ala Lys Thr
            115                 120
```

<210> SEQ ID NO 31

-continued

```
<211> LENGTH: 24
<212> TYPE: DNA
<213> ORGANISM: Artificial sequence
<220> FEATURE:
<223> OTHER INFORMATION: AR558 heavy chain CDR1 nucleotide coding
      sequence

<400> SEQUENCE: 31
ggcttcaaca ttaaagacac ctat                                            24

<210> SEQ ID NO 32
<211> LENGTH: 8
<212> TYPE: PRT
<213> ORGANISM: Artificial sequence
<220> FEATURE:
<223> OTHER INFORMATION: AR558 heavy chain CDR1 amino acids coding
      sequence

<400> SEQUENCE: 32

Gly Phe Asn Ile Lys Asp Thr Tyr
1               5

<210> SEQ ID NO 33
<211> LENGTH: 24
<212> TYPE: DNA
<213> ORGANISM: Artificial sequence
<220> FEATURE:
<223> OTHER INFORMATION: AR558 heavy chain CDR2 nucleotide coding
      sequence

<400> SEQUENCE: 33
attgatcctg cgaatcgtag tact                                            24

<210> SEQ ID NO 34
<211> LENGTH: 8
<212> TYPE: PRT
<213> ORGANISM: Artificial sequence
<220> FEATURE:
<223> OTHER INFORMATION: AR558 heavy chain CDR2 amino acids coding
      sequence

<400> SEQUENCE: 34

Ile Asp Pro Ala Asn Arg Ser Thr
1               5

<210> SEQ ID NO 35
<211> LENGTH: 39
<212> TYPE: DNA
<213> ORGANISM: Artificial sequence
<220> FEATURE:
<223> OTHER INFORMATION: AR558 heavy chain CDR3 nucleotide coding
      sequence

<400> SEQUENCE: 35
gctagacttt atggtgactc cgtctggtac ttcgatgtc                            39

<210> SEQ ID NO 36
<211> LENGTH: 13
<212> TYPE: PRT
<213> ORGANISM: Artificial sequence
<220> FEATURE:
<223> OTHER INFORMATION: AR558 heavy chain CDR3 amino acids coding
      sequence

<400> SEQUENCE: 36

Ala Arg Leu Tyr Gly Asp Ser Val Trp Tyr Phe Asp Val
1               5                   10
```

<210> SEQ ID NO 37
<211> LENGTH: 75
<212> TYPE: DNA
<213> ORGANISM: Artificial sequence
<220> FEATURE:
<223> OTHER INFORMATION: AR558 heavy chain FRM1 nucleotide coding
      sequence

<400> SEQUENCE: 37
gaggtccagc tgcagcagtc tggggcagaa cttgtgaagc caggggcctc agtcaagttg    60
tcctgcacag cttct                                                    75

<210> SEQ ID NO 38
<211> LENGTH: 25
<212> TYPE: PRT
<213> ORGANISM: Artificial sequence
<220> FEATURE:
<223> OTHER INFORMATION: AR558 heavy chain FRM1 amino acids coding
      sequence

<400> SEQUENCE: 38

Glu Val Gln Leu Gln Gln Ser Gly Ala Glu Leu Val Lys Pro Gly Ala
1               5                   10                  15

Ser Val Lys Leu Ser Cys Thr Ala Ser
            20                  25

<210> SEQ ID NO 39
<211> LENGTH: 51
<212> TYPE: DNA
<213> ORGANISM: Artificial sequence
<220> FEATURE:
<223> OTHER INFORMATION: AR558 heavy chain FRM2 nucleotide coding
      sequence

<400> SEQUENCE: 39
atgcactggg tgaaacagag gcctgaacag ggcctggagt ggattggaag g             51

<210> SEQ ID NO 40
<211> LENGTH: 17
<212> TYPE: PRT
<213> ORGANISM: Artificial sequence
<220> FEATURE:
<223> OTHER INFORMATION: AR558 heavy chain FRM2 amino acids coding
      sequence

<400> SEQUENCE: 40

Met His Trp Val Lys Gln Arg Pro Glu Gln Gly Leu Glu Trp Ile Gly
1               5                   10                  15

Arg

<210> SEQ ID NO 41
<211> LENGTH: 114
<212> TYPE: DNA
<213> ORGANISM: Artificial sequence
<220> FEATURE:
<223> OTHER INFORMATION: AR558 heavy chain FRM3 nucleotide coding
      sequence

<400> SEQUENCE: 41
aaatatgacc cgaagttcca gggcaaggcc actataacag cagacacatc ctccaacaca    60
gccgacctgc acctcagcag cctgacatct gaggacactg ccgtctatta ctgt         114

<210> SEQ ID NO 42
<211> LENGTH: 38

```
<212> TYPE: PRT
<213> ORGANISM: Artificial sequence
<220> FEATURE:
<223> OTHER INFORMATION: AR558 heavy chain FRM3 amino acids coding
      sequence

<400> SEQUENCE: 42

Lys Tyr Asp Pro Lys Phe Gln Gly Lys Ala Thr Ile Thr Ala Asp Thr
1               5                   10                  15

Ser Ser Asn Thr Ala Asp Leu His Leu Ser Ser Leu Thr Ser Glu Asp
            20                  25                  30

Thr Ala Val Tyr Tyr Cys
        35

<210> SEQ ID NO 43
<211> LENGTH: 42
<212> TYPE: DNA
<213> ORGANISM: Artificial sequence
<220> FEATURE:
<223> OTHER INFORMATION: AR558 heavy chain FRM4 nucleotide coding
      sequence

<400> SEQUENCE: 43
tggggcgcag ggaccacggt caccgtctcc tcagccaaaa cg                        42

<210> SEQ ID NO 44
<211> LENGTH: 14
<212> TYPE: PRT
<213> ORGANISM: Artificial sequence
<220> FEATURE:
<223> OTHER INFORMATION: AR558 heavy chain FRM4 amino acids coding
      sequence

<400> SEQUENCE: 44

Trp Gly Ala Gly Thr Thr Val Thr Val Ser Ser Ala Ser Thr
1               5                   10

<210> SEQ ID NO 45
<211> LENGTH: 327
<212> TYPE: DNA
<213> ORGANISM: Artificial sequence
<220> FEATURE:
<223> OTHER INFORMATION: AR558 light chain (kappa) complete nucleotide
      coding sequence

<400> SEQUENCE: 45
caaattgttc tctcccagtc tccagcaatc ctgtctgcat ctccagggga gaaggtcaca      60
atgacttgca gggccggctc aagtgtaaat tacatacact ggtaccagca gaagccagga     120
tcctccccca aaccctggat ttatgccaca tccaacctgg cttctggagt ccctgctcgc     180
ttcagtggca gtgggtctgg gacctcttac tctctcacaa tcagcagagt ggaggctgaa     240
gatgctgcca cttattactg ccagcagtgg agtggttacc cccccatgct cacgttcggt     300
gctggcacaa agctcgagct aaaacgt                                         327

<210> SEQ ID NO 46
<211> LENGTH: 109
<212> TYPE: PRT
<213> ORGANISM: Artificial sequence
<220> FEATURE:
<223> OTHER INFORMATION: AR558 light chain (kappa) complete amino acids
      coding sequence

<400> SEQUENCE: 46

Gln Ile Val Leu Thr Gln Ser Pro Ala Ile Leu Ser Ala Ser Pro Gly
```

```
  1               5                   10                  15
Glu Lys Val Thr Met Thr Cys Arg Ala Gly Ser Ser Val Asn Tyr Ile
                 20                  25                  30

His Trp Tyr Gln Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Gly Tyr Pro Pro Met
                 85                  90                  95

Leu Thr Phe Gly Ala Gly Thr Lys Leu Glu Leu Lys Arg
             100                 105
```

<210> SEQ ID NO 47
<211> LENGTH: 15
<212> TYPE: DNA
<213> ORGANISM: Artificial sequence
<220> FEATURE:
<223> OTHER INFORMATION: AR558 light chain CDR1 nucleotide coding
      sequence

<400> SEQUENCE: 47
tcaagtgtaa attac                                                15

<210> SEQ ID NO 48
<211> LENGTH: 5
<212> TYPE: PRT
<213> ORGANISM: Artificial sequence
<220> FEATURE:
<223> OTHER INFORMATION: AR558 light chain CDR1 amino acids coding
      sequence

<400> SEQUENCE: 48

Ser Ser Val Asn Tyr
1               5

<210> SEQ ID NO 49
<211> LENGTH: 9
<212> TYPE: DNA
<213> ORGANISM: Artificial sequence
<220> FEATURE:
<223> OTHER INFORMATION: AR558 light chain CDR2 nucleotide coding
      sequence

<400> SEQUENCE: 49 gccacatcc                                                        9

<210> SEQ ID NO 50
<211> LENGTH: 3
<212> TYPE: PRT
<213> ORGANISM: Artificial sequence
<220> FEATURE:
<223> OTHER INFORMATION: AR558 light chain CDR2 amino acids coding
      sequence

<400> SEQUENCE: 50

Ala Thr Ser
1

<210> SEQ ID NO 51
<211> LENGTH: 33
<212> TYPE: DNA
<213> ORGANISM: Artificial sequence

```
<220> FEATURE:
<223> OTHER INFORMATION: AR558 light chain CDR3 nucleotide coding
      sequence

<400> SEQUENCE: 51
cagcagtgga gtggttaccc ccccatgctc acg                                    33

<210> SEQ ID NO 52
<211> LENGTH: 11
<212> TYPE: PRT
<213> ORGANISM: Artificial sequence
<220> FEATURE:
<223> OTHER INFORMATION: AR558 light chain CDR3 amino acids coding
      sequence

<400> SEQUENCE: 52

Gln Gln Trp Ser Gly Tyr Pro Pro Met Leu Thr
1               5                   10

<210> SEQ ID NO 53
<211> LENGTH: 78
<212> TYPE: DNA
<213> ORGANISM: Artificial sequence
<220> FEATURE:
<223> OTHER INFORMATION: AR558 light chain FRM1 nucleotide coding
      sequence

<400> SEQUENCE: 53
caaattgttc tctcccagtc tccagcaatc ctgtctgcat ctccagggga gaaggtcaca       60
atgacttgca gggccggc                                                    78

<210> SEQ ID NO 54
<211> LENGTH: 26
<212> TYPE: PRT
<213> ORGANISM: Artificial sequence
<220> FEATURE:
<223> OTHER INFORMATION: AR558 light chain FRM1 amino acids coding
      sequence

<400> SEQUENCE: 54

Gln Ile Val Leu Thr Gln Ser Pro Ala Ile Leu Ser Ala Ser Pro Gly
1               5                   10                  15

Glu Lys Val Thr Met Thr Cys Arg Ala Gly
            20                  25

<210> SEQ ID NO 55
<211> LENGTH: 51
<212> TYPE: DNA
<213> ORGANISM: Artificial sequence
<220> FEATURE:
<223> OTHER INFORMATION: AR558 light chain FRM2 nucleotide coding
      sequence

<400> SEQUENCE: 55
atacactggt accagcagaa gccaggatcc tcccccaaac cctggattta t                51

<210> SEQ ID NO 56
<211> LENGTH: 17
<212> TYPE: PRT
<213> ORGANISM: Artificial sequence
<220> FEATURE:
<223> OTHER INFORMATION: AR558 light chain FRM2 amino acids coding
      sequence

<400> SEQUENCE: 56

Ile His Trp Tyr Gln Gln Lys Pro Gly Ser Ser Pro Lys Pro Trp Ile
```

Tyr

<210> SEQ ID NO 57
<211> LENGTH: 108
<212> TYPE: DNA
<213> ORGANISM: Artificial sequence
<220> FEATURE:
<223> OTHER INFORMATION: AR558 light chain FRM3 nucleotide coding
      sequence

<400> SEQUENCE: 57
aacctggctt ctggagtccc tgctcgcttc agtggcagtg ggtctgggac ctcttactct      60
ctcacaatca gcagagtgga ggctgaagat gctgccactt attactgc                  108

<210> SEQ ID NO 58
<211> LENGTH: 36
<212> TYPE: PRT
<213> ORGANISM: Artificial sequence
<220> FEATURE:
<223> OTHER INFORMATION: AR558 light chain FRM3 amino acids coding
      sequence

<400> SEQUENCE: 58

Asn Leu Ala Ser Gly Val Pro Ala Arg Phe Ser Gly Ser Gly Ser Gly
1               5                   10                  15

Thr Ser Tyr Ser Leu Thr Ile Ser Arg Val Glu Ala Glu Asp Ala Ala
            20                  25                  30

Thr Tyr Tyr Cys
        35

<210> SEQ ID NO 59
<211> LENGTH: 33
<212> TYPE: DNA
<213> ORGANISM: Artificial sequence
<220> FEATURE:
<223> OTHER INFORMATION: AR558 light chain FRM4 nucleotide coding
      sequence

<400> SEQUENCE: 59
ttcggtgctg gcacaaagct cgagctaaaa cgt                                   33

<210> SEQ ID NO 60
<211> LENGTH: 11
<212> TYPE: PRT
<213> ORGANISM: Artificial sequence
<220> FEATURE:
<223> OTHER INFORMATION: AR558 light chain FRM4 amino acids coding
      sequence

<400> SEQUENCE: 60

Phe Gly Ala Gly Thr Lys Leu Glu Leu Lys Arg
1               5                   10

<210> SEQ ID NO 61
<211> LENGTH: 351
<212> TYPE: DNA
<213> ORGANISM: Artificial sequence
<220> FEATURE:
<223> OTHER INFORMATION: AR37 heavy chain (IgG) complete nucleotide
      coding sequence

<400> SEQUENCE: 61
gaggtgaagc tggtggagtc tgggggagac ttagtgaagc ctggagggtc cctgaaactc      60

```
tcctgtgcag cctctggatt cactttcagt aactctggca tgtcttggtt tcgcctgact    120
ccagacaaga ggctggagtg ggtcgcaacc attagtagtg gtagtactta cacct tctat   180 ccagacactg tgaaggggcg attcatcatc tccagagaca atgccaagaa caccctgtac    240
ctgcaaatga gcagtctgaa gtctgaggac acagccatat attactgtgt aagagaaata    300
tggcccgtct ggggcgcagg gaccacgatc accgtctcct cagccaaaac g             351
```

<210> SEQ ID NO 62
<211> LENGTH: 117
<212> TYPE: PRT
<213> ORGANISM: Artificial sequence
<220> FEATURE:
<223> OTHER INFORMATION: AR37 heavy chain IgG complete amino acids
      coding sequence
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 62

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Ser
            20                  25                  30

Gly Met Xaa Trp Phe Arg Leu Thr Pro Asp Lys Arg Leu Glu Trp Val
        35                  40                  45

Ala Thr Ile Ser Ser Gly Ser Thr Tyr Thr Phe Tyr Pro Asp Thr Val
    50                  55                  60

Lys Gly Arg Phe Ile Ile Ser Arg Xaa Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Val Arg Glu Ile Trp Pro Val Trp Gly Ala Gly Thr Thr Ile Thr Val
            100                 105                 110

Ser Ser Ala Lys Thr
        115

<210> SEQ ID NO 63
<211> LENGTH: 24
<212> TYPE: DNA
<213> ORGANISM: Artificial sequence
<220> FEATURE:
<223> OTHER INFORMATION: AR37 heavy chain CDR1 nucleotide coding
      sequence

<400> SEQUENCE: 63

```
ggattcactt tcagtaactc tggc                                           24
```

<210> SEQ ID NO 64
<211> LENGTH: 8
<212> TYPE: PRT
<213> ORGANISM: Artificial sequence
<220> FEATURE:
<223> OTHER INFORMATION: AR37 heavy chain CDR1 amino acids coding
      sequence

<400> SEQUENCE: 64

Gly Phe Thr Phe Ser Asn Ser Gly
1               5

<210> SEQ ID NO 65
<211> LENGTH: 24
<212> TYPE: DNA
<213> ORGANISM: Artificial sequence
<220> FEATURE:
<223> OTHER INFORMATION: AR37 heavy chain CDR2 nucleotide coding
      sequence

<400> SEQUENCE: 65
attagtagtg gtagtactta cacc                                          24

<210> SEQ ID NO 66
<211> LENGTH: 8
<212> TYPE: PRT
<213> ORGANISM: Artificial sequence
<220> FEATURE:
<223> OTHER INFORMATION: AR37 heavy chain CDR2 amino acids coding
      sequence

<400> SEQUENCE: 66

Ile Ser Ser Gly Ser Thr Tyr Thr
1               5

<210> SEQ ID NO 67
<211> LENGTH: 21
<212> TYPE: DNA
<213> ORGANISM: Artificial sequence
<220> FEATURE:
<223> OTHER INFORMATION: AR37 heavy chain CDR3 nucleotide coding
      sequence

<400> SEQUENCE: 67
gtaagagaaa tatggcccgt c                                             21

<210> SEQ ID NO 68
<211> LENGTH: 7
<212> TYPE: PRT
<213> ORGANISM: Artificial sequence
<220> FEATURE:
<223> OTHER INFORMATION: AR37 heavy chain CDR3 amino acids coding
      sequence

<400> SEQUENCE: 68

Val Arg Glu Ile Trp Pro Val
1               5

<210> SEQ ID NO 69
<211> LENGTH: 75
<212> TYPE: DNA
<213> ORGANISM: Artificial sequence
<220> FEATURE:
<223> OTHER INFORMATION: AR37 heavy chain FRM1 nucleotide coding
      sequence

<400> SEQUENCE: 69
gaggtgcagc tggtggagtc tgggggagac ttagtgaagc tggagggtc cctgaaactc     60 tcctgtgcag cctct                                                    75

<210> SEQ ID NO 70
<211> LENGTH: 25
<212> TYPE: PRT
<213> ORGANISM: Artificial sequence
<220> FEATURE:
<223> OTHER INFORMATION: AR37 heavy chain FRM1 amino acids coding
      sequence

<400> SEQUENCE: 70

Glu Val Gln Leu Gln Gln Ser Gly Gly Asp Leu Val Lys Pro Gly Gly
1               5                   10                  15

Ser Leu Lys Leu Ser Cys Ala Ala Ser
            20                  25

<210> SEQ ID NO 71
<211> LENGTH: 51
<212> TYPE: DNA
<213> ORGANISM: Artificial sequence
<220> FEATURE:
<223> OTHER INFORMATION: AR37 heavy chain FRM2 nucleotide coding
      sequence

<400> SEQUENCE: 71
atgtcttggt tcgcctgac tccagacaag aggctggagt gggtcgcaac c        51

<210> SEQ ID NO 72
<211> LENGTH: 17
<212> TYPE: PRT
<213> ORGANISM: Artificial sequence
<220> FEATURE:
<223> OTHER INFORMATION: AR37 heavy chain FRM2 amino acids coding
      sequence

<400> SEQUENCE: 72

Met Ser Trp Phe Arg Leu Thr Pro Asp Lys Arg Leu Glu Trp Val Ala
1               5                   10                  15

Thr

<210> SEQ ID NO 73
<211> LENGTH: 114
<212> TYPE: DNA
<213> ORGANISM: Artificial sequence
<220> FEATURE:
<223> OTHER INFORMATION: AR37 heavy chain FRM3 nucleotide coding
      sequence

<400> SEQUENCE: 73
ttctatccag acactgtgaa ggggcgattc atcatctcca gagacaatgc caagaacacc    60
ctgtacctgc aaatgagcag tctgaagtct gaggacacag ccatatatta ctgt         114

<210> SEQ ID NO 74
<211> LENGTH: 38
<212> TYPE: PRT
<213> ORGANISM: Artificial sequence
<220> FEATURE:
<223> OTHER INFORMATION: AR37 heavy chain FRM3 amino acids coding
      sequence

<400> SEQUENCE: 74

Phe Tyr Pro Asp Thr Val Lys Gly Arg Phe Ile Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Ile Tyr Tyr Cys
        35

<210> SEQ ID NO 75
<211> LENGTH: 42
<212> TYPE: DNA
<213> ORGANISM: Artificial sequence
<220> FEATURE:
<223> OTHER INFORMATION: AR37 heavy chain FRM4 nucleotide coding -continued sequence

<400> SEQUENCE: 75
tggggcgcag ggaccacgat caccgtctcc tcagccaaaa cg        42

<210> SEQ ID NO 76
<211> LENGTH: 14
<212> TYPE: PRT
<213> ORGANISM: Artificial sequence
<220> FEATURE:
<223> OTHER INFORMATION: AR37 heavy chain FRM4 amino acids coding
      sequence

<400> SEQUENCE: 76

Trp Gly Ala Gly Thr Thr Ile Thr Val Ser Ser Ala Lys Thr
1               5                   10

<210> SEQ ID NO 77
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 77
acttcataga ctccatcaag aa        22

<210> SEQ ID NO 78
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 78
ctcgtccagc ttgactcgat        20

<210> SEQ ID NO 79
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 79
tccatcttct acaggcagtc ct        22

<210> SEQ ID NO 80
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 80
agccacacgt ggattgtctt        20

<210> SEQ ID NO 81
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 81
cactggagcc aaaacctgtc        20

<210> SEQ ID NO 82
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 82
agtgactgag cggctaatgc                                                    20

<210> SEQ ID NO 83
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 83
gctgtggtgc tgtcatctgt                                                    20

<210> SEQ ID NO 84
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 84
tcatgcccaa cttcactttc t                                                  21

<210> SEQ ID NO 85
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 85
gtttttggtg caggaggaca                                                    20

<210> SEQ ID NO 86
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 86
caccaacgta cccagaatgg                                                    20

<210> SEQ ID NO 87
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 87
gccactgctt tgcagaaaat                                                    20

<210> SEQ ID NO 88
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 88
cctcttcatg tggtcccaag                                          20

<210> SEQ ID NO 89
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 89
tgcctgccgt gtgaaccatg t                                        21

<210> SEQ ID NO 90
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 90
tgcggcatct tcaaacctcc atga                                     24

<210> SEQ ID NO 91
<211> LENGTH: 294
<212> TYPE: DNA
<213> ORGANISM: Artificial sequence
<220> FEATURE:
<223> OTHER INFORMATION: AREGs EGF-like domain (human)

<400> SEQUENCE: 91
tcagtcagag ttgaacaggt agttaagccc ccccaaaaca agacggaaag tgaaaatact    60
tcagataaac ccaaaagaaa gaaaaaggga ggcaaaaatg gaaaaaatag aagaaacaga   120
aagaagaaaa atccatgtaa tgcagaattt caaaatttct gcattcacgg agaatgcaaa   180
tatatagagc acctggaagc agtaacatgc aaatgtcagc aagaatattt cggtgaacgg   240
tgtggggaaa agtccatgaa aactcacagc atgattgaca gtagtttatc aaaa        294

<210> SEQ ID NO 92
<211> LENGTH: 98
<212> TYPE: PRT
<213> ORGANISM: Artificial sequence
<220> FEATURE:
<223> OTHER INFORMATION: AREGs EGF-like domain (human)

<400> SEQUENCE: 92

Ser Val Arg Val Glu Gln Val Val Lys Pro Pro Gln Asn Lys Thr Glu
1               5                   10                  15

Ser Glu Asn Thr Ser Asp Lys Pro Lys Arg Lys Lys Lys Gly Gly Lys
                20                  25                  30

Asn Gly Lys Asn Arg Arg Asn Arg Lys Lys Lys Asn Pro Cys Asn Ala
            35                  40                  45

Glu Phe Gln Asn Phe Cys Ile His Gly Glu Cys Lys Tyr Ile Glu His
        50                  55                  60

Leu Glu Ala Val Thr Cys Lys Cys Gln Gln Glu Tyr Phe Gly Glu Arg
65                  70                  75                  80

Cys Gly Glu Lys Ser Met Lys Thr His Ser Met Ile Asp Ser Ser Leu
                85                  90                  95

Ser Lys

<210> SEQ ID NO 93
<211> LENGTH: 109
<212> TYPE: PRT
<213> ORGANISM: Artificial sequence
<220> FEATURE:
<223> OTHER INFORMATION: AR37 light chain (IgG) complete amino acids
      coding sequence

<400> SEQUENCE: 93

```
Gln Ala Val Val Thr Gln Glu Ser Ala Leu Ser Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Leu Gly Asp Thr Asp Asn Arg Pro Pro Gly Val Pro Ala Arg Phe
    50                  55                  60

Ser Gly Ser Leu Leu Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 94
<211> LENGTH: 9
<212> TYPE: PRT
<213> ORGANISM: Artificial sequence
<220> FEATURE:
<223> OTHER INFORMATION: AR37 light chain CDR1 amino acids coding
      sequence

<400> SEQUENCE: 94

```
Thr Gly Ala Val Thr Thr Ser Asn Tyr
1               5
```

<210> SEQ ID NO 95
<211> LENGTH: 3
<212> TYPE: PRT
<213> ORGANISM: Artificial sequence
<220> FEATURE:
<223> OTHER INFORMATION: AR37 light chain CDR2 amino acids coding
      sequence

<400> SEQUENCE: 95

```
Asp Thr Asp
1
```

<210> SEQ ID NO 96
<211> LENGTH: 9
<212> TYPE: PRT
<213> ORGANISM: Artificial sequence
<220> FEATURE:
<223> OTHER INFORMATION: AR37 light chain CDR3 amino acids coding
      sequence

<400> SEQUENCE: 96

```
Ala Leu Trp Tyr Ser Asn His Trp Val
1               5
```

<210> SEQ ID NO 97
<211> LENGTH: 25
<212> TYPE: PRT

<213> ORGANISM: Artificial sequence
<220> FEATURE:
<223> OTHER INFORMATION: AR37 light chain FRM1 amino acids coding sequence

<400> SEQUENCE: 97

Gln Ala Val Val Thr Gln Glu Ser Ala Leu Ser Thr Ser Pro Gly Glu
1               5                   10                  15

Thr Val Thr Leu Thr Cys Arg Ser Ser
            20                  25

<210> SEQ ID NO 98
<211> LENGTH: 17
<212> TYPE: PRT
<213> ORGANISM: Artificial sequence
<220> FEATURE:
<223> OTHER INFORMATION: AR37 light chain FRM2 amino acids coding sequence

<400> SEQUENCE: 98

Ala Asn Trp Val Gln Glu Lys Pro Asp His Leu Phe Thr Gly Leu Leu
1               5                   10                  15

Gly

<210> SEQ ID NO 99
<211> LENGTH: 36
<212> TYPE: PRT
<213> ORGANISM: Artificial sequence
<220> FEATURE:
<223> OTHER INFORMATION: AR37 light chain FRM3 amino acids coding sequence

<400> SEQUENCE: 99

Asn Arg Pro Pro Gly Val Pro Ala Arg Phe Ser Gly Ser Leu Leu Gly
1               5                   10                  15

Asp Lys Ala Ala Leu Thr Ile Thr Gly Ala Gln Thr Glu Asp Glu Ala
            20                  25                  30

Ile Tyr Phe Cys
        35

<210> SEQ ID NO 100
<211> LENGTH: 116
<212> TYPE: PRT
<213> ORGANISM: Artificial sequence
<220> FEATURE:
<223> OTHER INFORMATION: AR37 light chain FRM4 amino acids coding sequence (including the constant region)

<400> SEQUENCE: 100

Phe Gly Gly Gly Thr Lys Leu Thr Val Leu Gly Gln Pro Lys Ser Ser
1               5                   10                  15

Pro Ser Val Thr Leu Phe Pro Pro Ser Ser Glu Glu Leu Glu Thr Asn
            20                  25                  30

Lys Ala Thr Leu Val Cys Thr Leu Thr Asp Phe Tyr Pro Gly Val Val
            35                  40                  45

Thr Val Asp Trp Lys Val Asp Gly Thr Pro Val Thr Gln Gly Met Glu
        50                  55                  60

Thr Thr Gln Pro Ser Lys Gln Ser Asn Asn Lys Tyr Met Ala Ser Ser
65                  70                  75                  80

Tyr Leu Thr Leu Thr Ala Arg Ala Trp Gln Arg His Ser Ser Tyr Ser
                85                  90                  95

Cys Gln Val Thr His Glu Gly His Thr Val Glu Lys Ser Leu Ser Arg

Ala Asp Cys Ser
    115

<210> SEQ ID NO 101
<211> LENGTH: 27
<212> TYPE: DNA
<213> ORGANISM: Artificial sequence
<220> FEATURE:
<223> OTHER INFORMATION: AR37 light chain CDR1 nucleotide coding
      sequence

<400> SEQUENCE: 101
actggggctg ttacaactag taactat                                         27

<210> SEQ ID NO 102
<211> LENGTH: 9
<212> TYPE: DNA
<213> ORGANISM: Artificial sequence
<220> FEATURE:
<223> OTHER INFORMATION: AR37 light chain CDR2 nucleotide coding
      sequence
<220> FEATURE:
<221> NAME/KEY: misc_feature
<222> LOCATION: (3)..(3)
<223> OTHER INFORMATION: n=T or C
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n=T or C

<400> SEQUENCE: 102 ganacngan                                                              9

<210> SEQ ID NO 103
<211> LENGTH: 75
<212> TYPE: DNA
<213> ORGANISM: Artificial sequence
<220> FEATURE:
<223> OTHER INFORMATION: AR37 light chain FRM1 nucleotide coding
      sequence

<400> SEQUENCE: 103
caggctgttg tgactcagga atctgcactc accacatcac ctggtgaaac agtcacactc     60
acttgtcgct caagt                                                       75

<210> SEQ ID NO 104
<211> LENGTH: 51
<212> TYPE: DNA
<213> ORGANISM: Artificial sequence
<220> FEATURE:
<223> OTHER INFORMATION: AR37 light chain FRM2 nucleotide coding
      sequence

<400> SEQUENCE: 104
gccaactggg tccaagaaaa accagatcat ttattcactg gtctaatagg t              51

ANTI AMPHIREGULIN ANTIBODIES, COMPOSITIONS COMPRISING SAME AND USES THEREOF

RELATED APPLICATIONS

This application is a division of U.S. patent application Ser. No. 15/271,515 filed on Sep. 21, 2016, which is a Continuation-in-Part (CIP) of PCT Patent Application No. PCT/IL2016/050299 filed on Mar. 17, 2016, which claims the benefit of priority of Israel Patent Application No. 237852 filed on Mar. 19, 2015, now abandoned, the contents of which are incorporated herein by reference in their entirety.

SEQUENCE LISTING STATEMENT

The ASCII file, entitled 74548SequenceListing.txt, created on Jul. 25, 2018, comprising 37,496 bytes, submitted concurrently with the filing of this application is incorporated herein by reference.

FIELD AND BACKGROUND OF THE INVENTION

The present invention, in some embodiments thereof, relates to anti-amphiregulin antibodies, compositions comprising same and uses thereof.

Growth factors and their cognate receptors mediate rapid responses to extracellular cues in a process tightly regulated by positive and negative feedback loops. Disturbance of this delicate balance is often implicated in disease development. An example of this scenario is provided by the Epidermal Growth Factor Receptor (EGFR) family of receptor tyrosine kinases (RTKs), and their EGF-like ligands. The family is comprised of four RTKs (EGFR/ERBB1/HER1, ERBB2/HER2, ERBB3/HER3 and ERBB4/HER4) and 11 ligands, polypeptides of the EGF/neuregulin (NRG) family. These ligands might be classified according to their affinity to EGFR, for example, EGF, transforming growth factor alpha (TGF-alpha), heparin-binding epidermal growth factor (HB-EGF), and betacellulin (BTC) are considered high-affinity ligands. By contrast, amphiregulin (AREG), epiregulin (EREG) and epigen (EPG) are considered low-affinity ligands.

It is well established that ligand binding to the extracellular region of EGFR promotes dimerization of the receptor and increases the activity of its intracellular kinase domain, leading to the activation of downstream signaling pathways. Following ligand binding, EGFR is rapidly internalized from the cell surface, which results in signal attenuation, either through the degradation of both receptor and ligand or the ligand alone. Interestingly, although high-affinity ligands stimulate a strong and robust response, the burst of activation is short lived due to potent negative feedback loops. However, under certain conditions the low-affinity ligands, including an engineered ligand, display relatively high mitogenic potency due to incompletely understood mechanisms. This phenomenon is also observed with the many EGFR ligands encoded by poxviruses. These viral ligands often display lower receptor binding affinity, as compared to their mammalian counterparts, but their biological activities are sometime more potent.

Of the low affinity ligands, AREG is being increasingly recognized for the key roles it plays in both normal and disease contexts. Human AREG is located on chromosome band 4q14.3 spanning approximately 10 kb of genomic DNA. AREG is flanked on the 5' region by its family members EREG and EPG and on the 3' region by another kin, BTC. The gene is composed of 6 exons that encode a 1.4 kb mRNA. The corresponding protein is synthesized as a 252 amino acid transmembrane precursor (pro-AREG), which is subjected to proteolytic cleavage within its ectodomain, thereby releasing a biologically active, soluble protein. This process is mediated by the tumor-necrosis factor-alpha converting enzyme (TACE), a member of the disintegrin and metalloproteinase family (also known as ADAM 17).

EGFR may be activated by AREG in several ways: autocrine or paracrine activation by the soluble form of AREG, a juxtacrine mode enabling the un-cleaved transmembrane form to activate EGFR, or by a newly described mode of signaling entailing AREG containing exosomes, that better enhance invasion of recipient cells in comparison to exosomes containing high affinity ligands.

AREG plays pivotal roles in mammary gland development, in oocyte maturation, as well as in branching and morphogenesis occurring within epithelial tissues, such as lung, prostate and kidney. Conversely, AREG has also been linked to the oncogenic process. AREG expression has been associated with worse prognosis of prostate, hepatocellular, pancreatic, breast, lung, colon, and head and neck tumors.

Additional background art includes:

U.S. Patent Application No. 2004/0210040 relates to amphiregulin (AR) antibodies and their use to treat cancer and psoriasis. Specifically, U.S. 2004/0210040 teaches anti-AR antibodies as well as pharmaceutical compositions comprising same and the use of same in inhibiting cancer cell (e.g. ovarian cancer) growth or psoriasis. The antibody of U.S. 2004/0210040 may be conjugated to an effector moiety such as a cytotoxic agent or may be administered in conjunction with a cytotoxic agent (e.g. chemotherapeutic agent).

U.S. Patent Application No. 2006/0246448 relates to inhibition of TACE or amphiregulin for the modulation of EGFR signal transactivation. Specifically, U.S. 2006/0246448 provides antibodies or antibody fragments directed against amphiregulin or TACE and the use of same for the treatment of hyperproliferative disorder such as cancer or psoriasis.

So et al. Febs Lett. 2014 588(21):3998-4007 teaches that increase in AREG induces ovarian cancer metastasis. Specifically, So et al. illustrate that AREG induces ovarian cancer cell invasion by down-regulating E-cadherin expression.

SUMMARY OF THE INVENTION

According to an aspect of some embodiments of the present invention there is provided a method of determining the suitability of a subject to a treatment with an anti-amphiregulin antibody, wherein the subject has a cancer selected from the group consisting of ovarian cancer, head and neck cancer and pancreatic cancer exhibiting resistance to chemotherapy, the method comprising analyzing in a biological sample of the subject expression level of amphiregulin, transforming growth factor alpha (TGF-alpha) and heparin-binding epidermal growth factor (HB-EGF), wherein a level of expression of the amphiregulin above a predetermined threshold and no expression of the TGF-alpha and/or the HB-EGF or an expression below a predetermined level of the TGF-alpha and/or the HB-EGF is indicative of the suitability of the subject to treatment with the anti-amphiregulin antibody.

According to an aspect of some embodiments of the present invention there is provided a composition of matter comprising a biological sample of a subject having a cancer selected from the group consisting of ovarian cancer, head and neck cancer and pancreatic cancer exhibiting resistance to chemotherapy, and a monoclonal antibody to amphiregulin, and optionally TGF-alpha and/or HB-EGF.

According to some embodiments of the invention, the biological sample comprises a biopsy.

According to some embodiments of the invention, the biopsy comprises an ascites fluid or a pleural fluid.

According to some embodiments of the invention, the biological sample comprises a blood sample.

According to some embodiments of the invention, the cancer is ovarian cancer and wherein the chemotherapy is a platinum derivative.

According to an aspect of some embodiments of the present invention there is provided a method of treating cancer, the method comprising administering to a subject selected according to the method of some embodiments of the invention a therapeutically effective amount of an agent which down-regulates an activity or expression of amphiregulin, thereby treating the cancer.

According to an aspect of some embodiments of the present invention there is provided a use of a therapeutically effective amount of an agent which down-regulates an activity or expression of amphiregulin for the manufacture of a medicament identified for treating a cancer in a subject selected according to the method of some embodiments of the invention.

According to an aspect of some embodiments of the present invention there is provided a method of producing an antibody specific for human amphiregulin, the method comprising immunizing an amphiregulin knockout animal with a human amphiregulin protein or peptide thereof so as to produce an antibody response against the amphiregulin protein or peptide thereof, thereby producing the antibody specific for human amphiregulin.

According to some embodiments of the invention, the method further comprises generating monoclonal antibodies from the antibody producing cells of the knockout animal following the immunizing.

According to some embodiments of the invention, the antibody is a polyclonal antibody.

According to an aspect of some embodiments of the present invention there is provided an antibody produced according to the method of some embodiments of the invention.

According to an aspect of some embodiments of the present invention there is provided an antibody comprising an antigen recognition domain which specifically binds amphiregulin and comprises complementarity determining regions (CDRs) as set forth in SEQ ID NOs: 4, 6, 8, 18, 20 and 22 (AR30).

According to an aspect of some embodiments of the present invention there is provided an antibody comprising an antigen recognition domain which specifically binds amphiregulin and comprises complementarity determining regions (CDRs) as set forth in SEQ ID NOs: 32, 34, 36, 48, 50 and 52 (AR558).

According to an aspect of some embodiments of the present invention there is provided an antibody comprising an antigen recognition domain which specifically binds amphiregulin and comprises complementarity determining regions (CDRs) as set forth in SEQ ID NOs: 64, 66 and 68, 94, 95 and 96 (AR37).

According to some embodiments of the invention, the CDRs set forth in SEQ ID NOs: 18, 20 and 22 are arranged in a sequential order from N to C on a light chain of the antibody and the CDRs set forth in SEQ ID NOs: 4, 6 and 8 are arranged in a sequential order from N to C on a heavy chain of the antibody.

According to some embodiments of the invention, the CDRs set forth in SEQ ID NOs: 48, 50 and 52 are arranged in a sequential order from N to C on a light chain of the antibody and the CDRs set forth in SEQ ID NOs: 32, 34 and 36 are arranged in a sequential order from N to C on a heavy chain of the antibody.

According to some embodiments of the invention, the CDRs set forth in SEQ ID NOs: 94, 95 and 96 are arranged in a sequential order from N to C on a light chain of the antibody and the CDRs set forth in SEQ ID NOs: 64, 66 and 68 are arranged in a sequential order from N to C on a heavy chain of the antibody.

According to some embodiments of the invention, the antibody is capable of sensitizing ovarian cancer cells to a chemotherapeutic agent.

According to some embodiments of the invention, the antibody is capable of reducing ovarian tumor size of an ovarian tumor secreting amphiregulin.

According to some embodiments of the invention, the antibody is a pan-amphiregulin antibody.

According to some embodiments of the invention, the antibody does not react with a mouse amphiregulin.

According to some embodiments of the invention, the antibody is humanized.

According to some embodiments of the invention, the antibody is a chimeric antibody.

According to some embodiments of the invention, the antibody is conjugated to an effector moiety.

According to some embodiments of the invention, the effector moiety is selected from the group consisting of a radiotherapy, a toxin, a chemotherapy and a label.

According to some embodiments of the invention, the chemotherapy is platinum based.

According to some embodiments of the invention, the antibody comprises an antigen recognition domain which specifically binds amphiregulin with a $K_D$ below 10 nM.

According to an aspect of some embodiments of the present invention there is provided an antibody combination comprising at least two antibodies with a first antibody of the antibody combination being the antibody of some embodiments of the invention.

According to some embodiments of the invention, the antibody combination comprises the antibodies of some embodiments of the invention.

According to some embodiments of the invention, the second antibody of the antibody combination binds an Epidermal Growth Factor Receptor (EGFR) ligand distinctive from the first antibody.

According to an aspect of some embodiments of the present invention there is provided a pharmaceutical composition comprising as an active ingredient the antibody of some embodiments of the invention or the antibody combination of some embodiments of the invention and a pharmaceutically acceptable carrier.

According to an aspect of some embodiments of the present invention there is provided a method for treating a cancer in a subject in need thereof, the method comprising administering to the subject a therapeutically effective amount of some embodiments of the invention or the antibody combination of some embodiments of the invention, thereby treating the cancer.

According to an aspect of some embodiments of the present invention there is provided a use of a therapeutically effective amount of the antibody of some embodiments of the invention or the antibody combination of some embodiments of the invention for the manufacture of a medicament identified for treating a cancer in a subject in need thereof.

According to some embodiments of the invention, the cancer is selected from the group consisting of an ovarian cancer, a lung cancer, a liver cancer, head and neck cancer, pancreatic cancer, and a breast cancer.

According to some embodiments of the invention, the cancer comprises an ovarian cancer.

According to some embodiments of the invention, the subject is resistant to chemotherapy.

According to some embodiments of the invention, the subject is characterized by an expression level of amphiregulin above a predetermined threshold and optionally no expression of TGF-alpha and/or HB-EGF or an expression below a predetermined level of the TGF-alpha and/or HB-EGF as compared to a healthy subject.

According to some embodiments of the invention, the method further comprises testing the subject for expression levels of amphiregulin and optionally HB-EGF and TGF-alpha prior to the administering.

According to some embodiments of the invention, the method further comprises administering to the subject a chemotherapeutic agent.

According to some embodiments of the invention, the chemotherapeutic agent is a cisplatin or a doxorubicin.

According to some embodiments of the invention, the therapeutically effective amount results in sensitization of cancer cells of the subject to a chemotherapeutic agent following the administering.

According to some embodiments of the invention, the therapeutically effective amount results in reduction in tumor size in the subject following the administering.

According to an aspect of some embodiments of the present invention there is provided an article of manufacture comprising the antibody of some embodiments of the invention or the antibody combination of some embodiments of the invention and a chemotherapy being packaged in a packaging material and identified in print, in or on the packaging material for use in the treatment of cancer.

According to some embodiments of the invention, the antibody or the antibody combination and the chemotherapy are in separate containers.

According to some embodiments of the invention, the chemotherapy is platinum based.

According to an aspect of some embodiments of the present invention there is provided an isolated polynucleotide encoding the antibody of some embodiments of the invention.

According to some embodiments of the invention, the isolated polynucleotide comprises the nucleic acid sequences as set forth in SEQ ID NOs: 3, 5, 7, 17, 19 and 21.

According to an aspect of some embodiments of the present invention there is provided an isolated polynucleotide encoding the antibody of some embodiments of the invention.

According to some embodiments of the invention, the isolated polynucleotide comprises the nucleic acid sequences as set forth in SEQ ID NOs: 31, 33, 35, 47, 49 and 51.

According to an aspect of some embodiments of the present invention there is provided an isolated polynucleotide encoding the antibody of some embodiments of the invention.

According to some embodiments of the invention, the isolated polynucleotide of some embodiments of the invention comprises the nucleic acid sequences as set forth in SEQ ID NOs: 63, 65 and 67.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
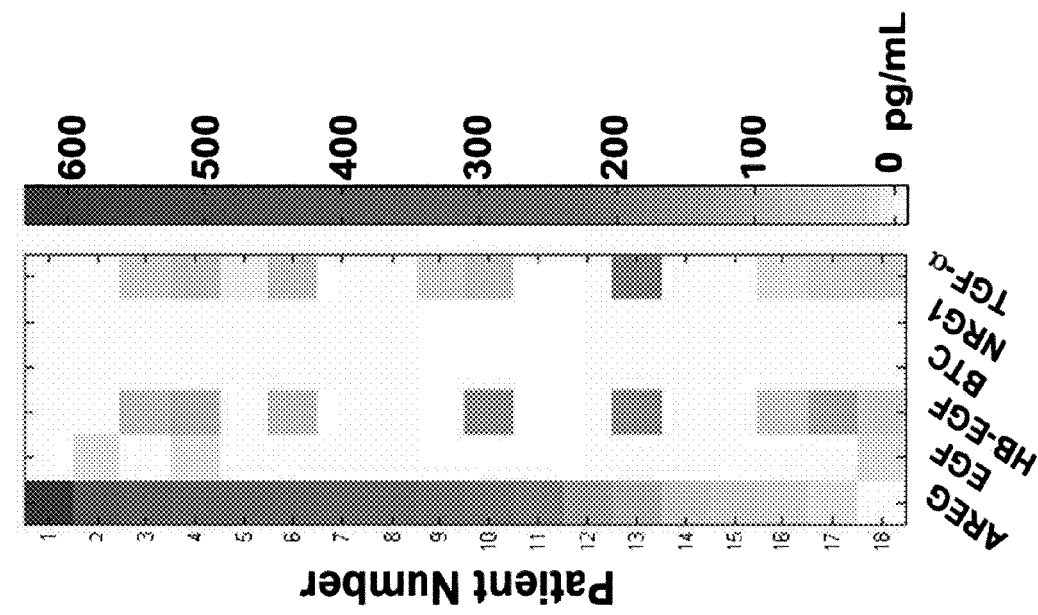
Figure 1A:
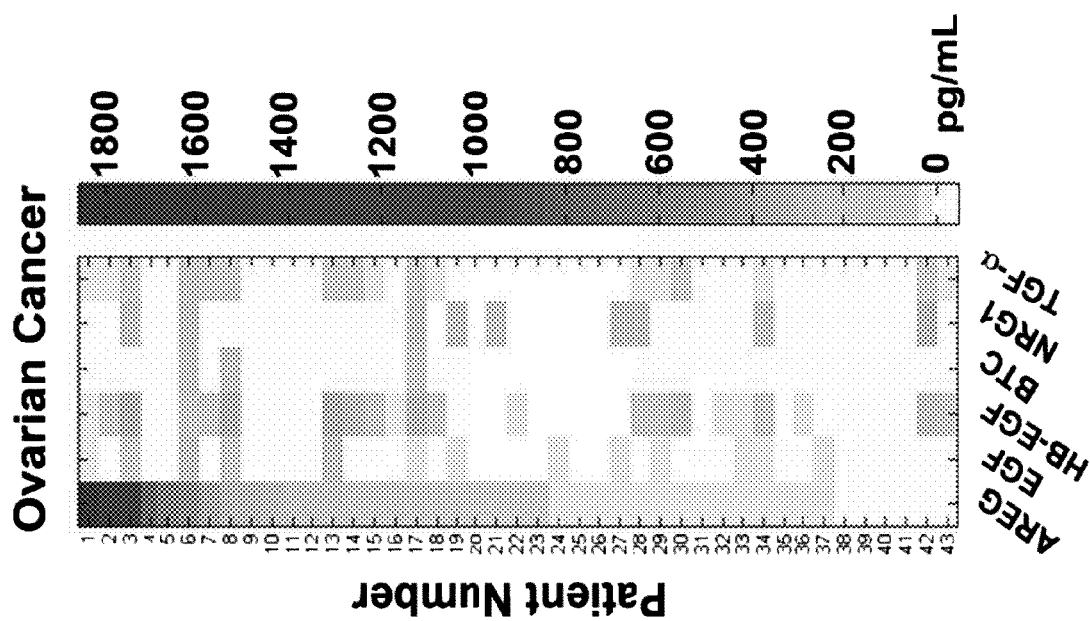
Figure 1C:
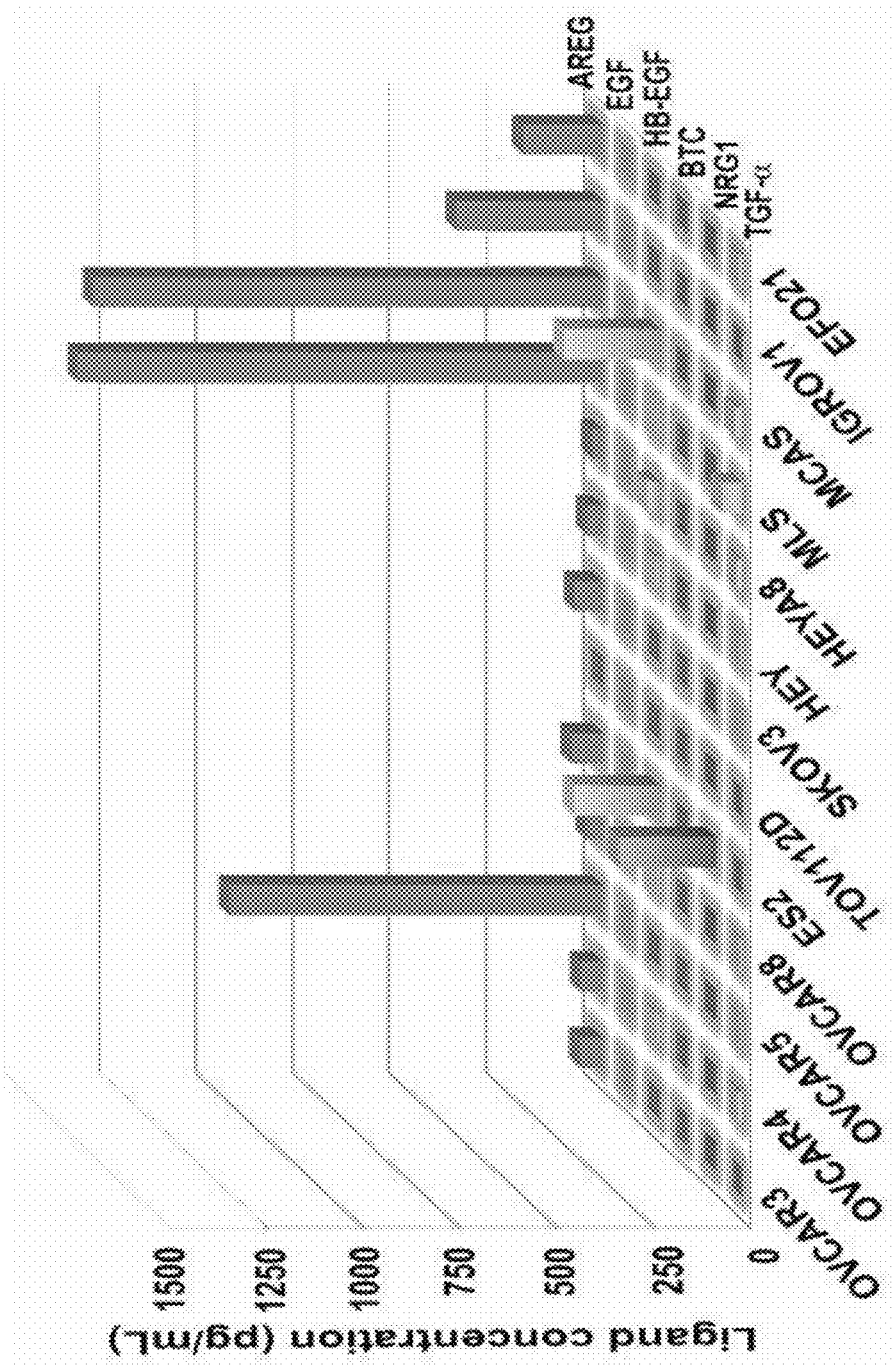
Figure 1D:
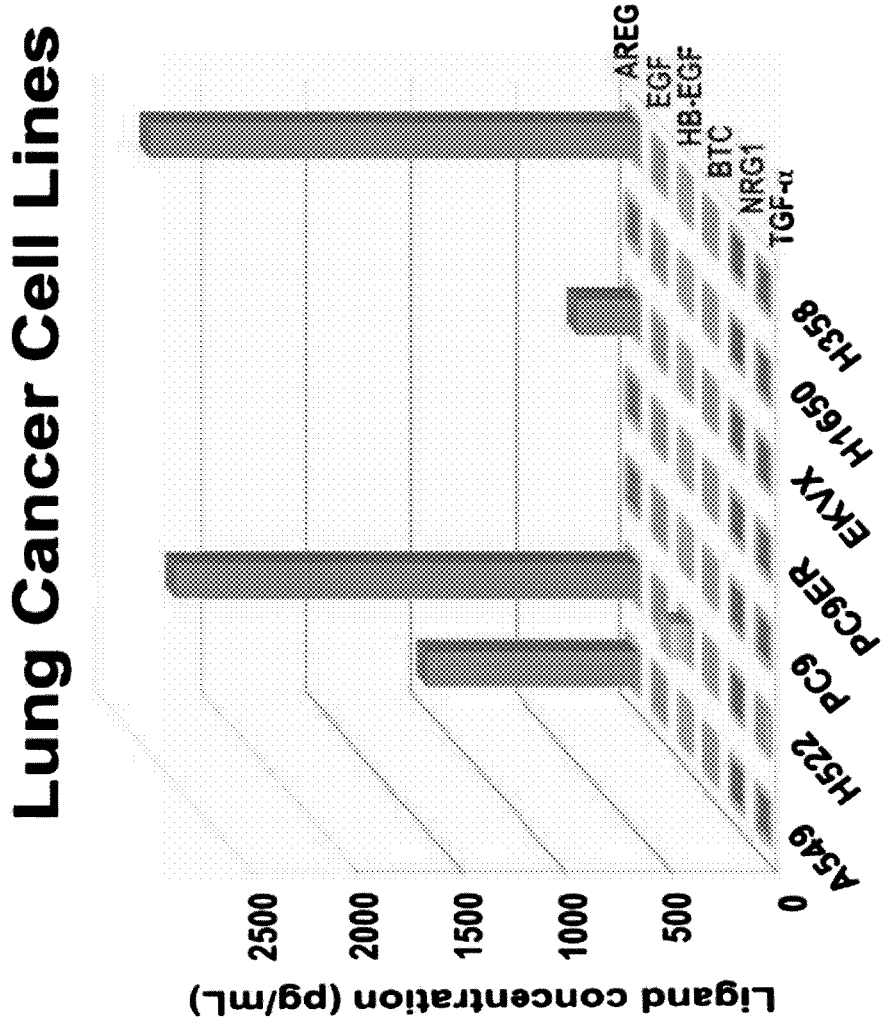

FIGS. 1A-1D illustrate high abundance of AREG in fluids from ovarian and lung cancer patients and in media conditioned by ovarian cancer cells. FIG. 1A is a heatmap representation of the abundance of the indicated EGF-family ligands as determined using ELISA and 43 ascites fluids collected from patients with ovarian cancer. The color range is depicted (right column); FIG. 1B is a heatmap representation of pleural effusion fluids collected from lung cancer patients analyzed as in FIG. 1A; FIG. 1C is a graph illustrating the expression of EGF-family ligands in ovarian cancer cells. The indicated 13 ovarian cell lines were seeded in 10 cm plates, covered with medium (6 mL), and incubated for 4 days. Media were collected and the specified ligands were quantified using ELISA; and FIG. 1D is a graph illustrating the expression of EGF-family ligands in lung cancer cell lines. A panel of seven lung cancer cell lines was analyzed as in FIG. 1C.

Figure 1F:
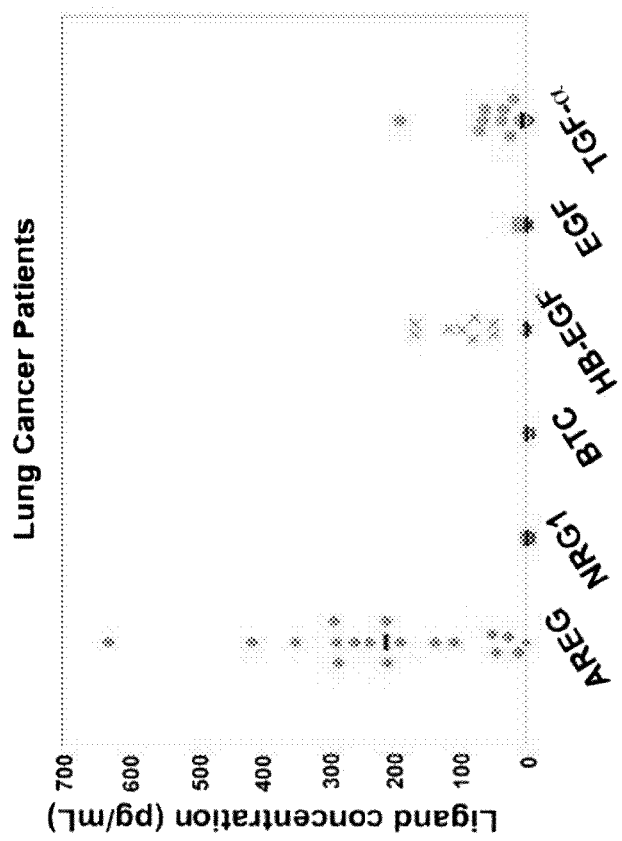
Figure 1E:
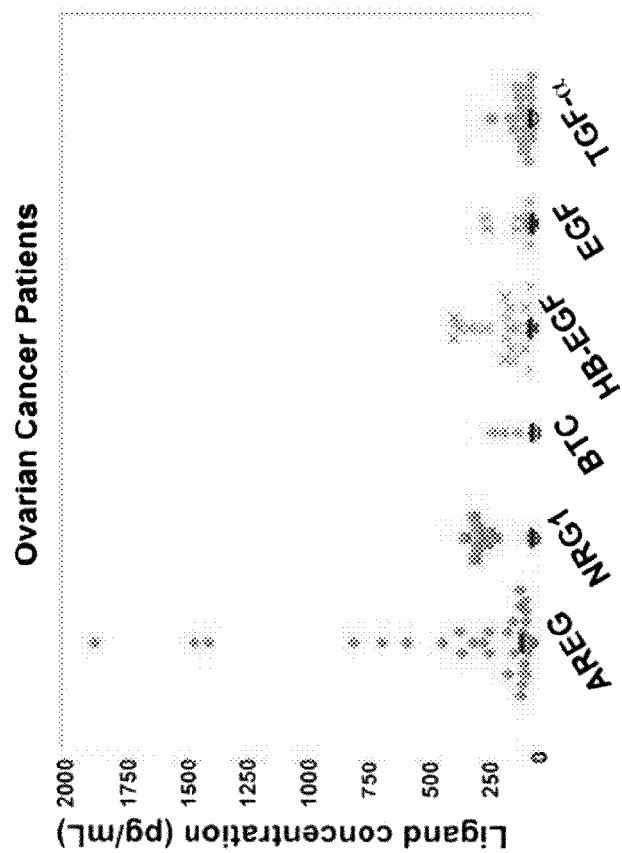

FIGS. 1E-1F illustrate that AREG is commonly detectable in fluids from ovarian and lung cancer patients. FIG. 1E is a scatter plot representation of ELISA determinations of the indicated growth factors in ascites fluids from ovarian cancer patients (n=43); and FIG. 1F is a scatter plot representation, as in FIG. 1E, of the indicated growth factors in pleural effusion fluids from 18 lung cancer patients. Each dot represents one patient (see FIGS. 1A-B and Table 1, below).

Figure 2A:
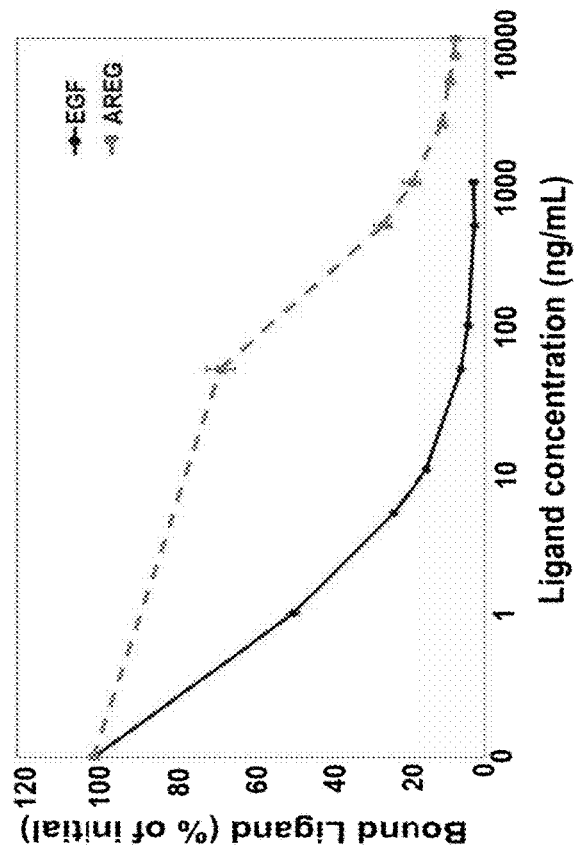
Figure 2B:
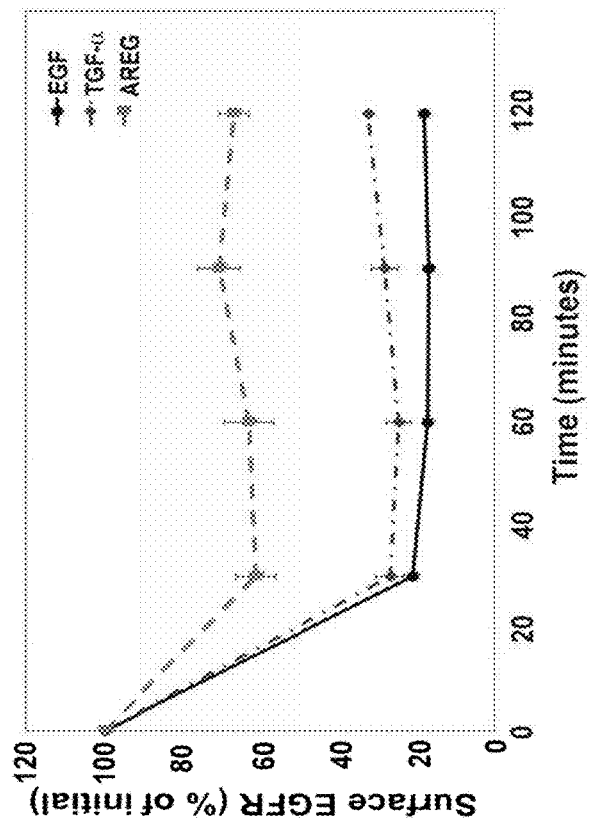
Figure 2D:
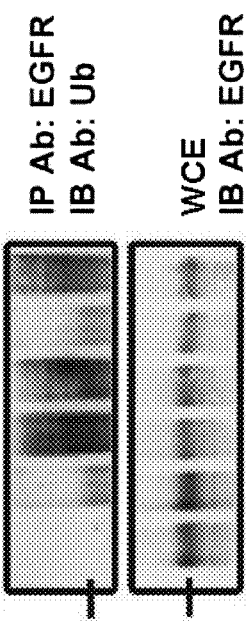
Figure 2F:
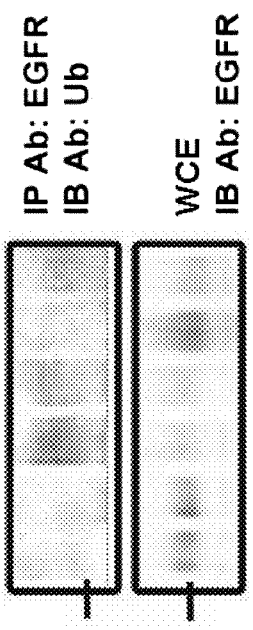
Figure 2C:
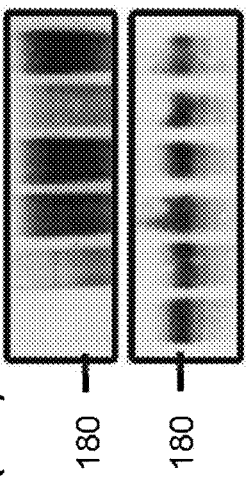
Figure 2E:
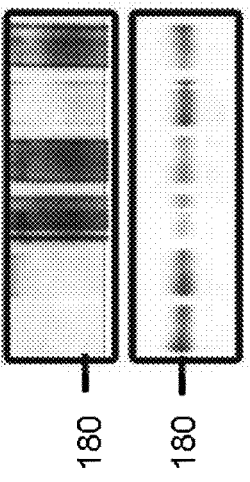

FIGS. 2A-2F illustrate that AREG is a low affinity ligand that induces limited receptor downregulation, as well as weak ubiquitination and degradation of EGFR. FIG. 2A is a graph showing results of MCAS ovarian cancer cells plated in 12-well plates and incubated for 3 hours on ice with a radiolabeled EGF ($^{125}$I-EGF; 50 ng/mL) in the absence or presence of increasing concentrations of the indicated competing (unlabeled) ligand. The cells were later washed and lysed, and the associated radioactivity was determined. The extent of ligand displacement (mean±range of triplicates) was plotted with respect to binding in the absence of an unlabeled ligand; FIG. 2B is a graph showing results of MCAS ovarian cells incubated in a 12 well plate and starved overnight for serum factors. On the following day, cells were stimulated (or un-stimulated) with EGF (10 ng/mL), TGF-alpha (10 ng/mL) or AREG (50 ng/mL) for 30, 60, 90 and 120 minutes. Next, cells were transferred to 4° C. and EGFR downregulation was assayed following exposure to a radioactive EGF ($^{125}$I-EGF; 50 ng/mL) for 60 minutes. The cells were later washed and lysed in 1 N NaOH. Cell-associated radioactivity was determined. Averages of triplicates and S.D. values (bars) are presented; and FIGS. 2C-2F are photographs showing results of whole extracts of the ovarian cancer cell lines MCAS and MLS, as well as the lung cancer cell lines H358 and A549, that were pre-stimulated for 10 minutes with EGF (100 ng/mL), TGF-alpha (100 ng/mL) or AREG (100 ng/mL or 1 µg/mL) and were subjected to immunoprecipitation (IP) of EGFR. Washed immunocomplexes, along with whole extracts, were immunoblotted with the indicated antibodies.

Figure 2G:
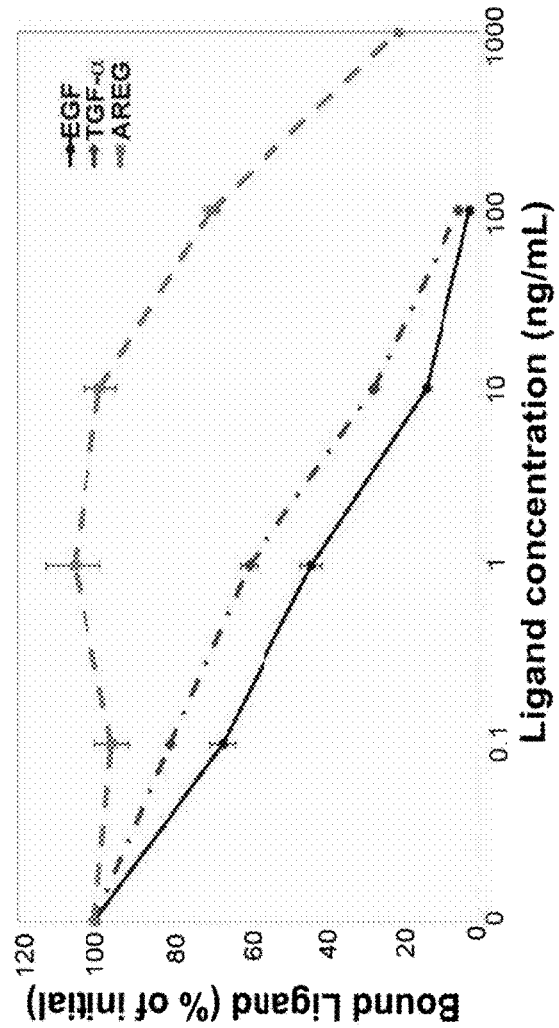
Figure 2H:
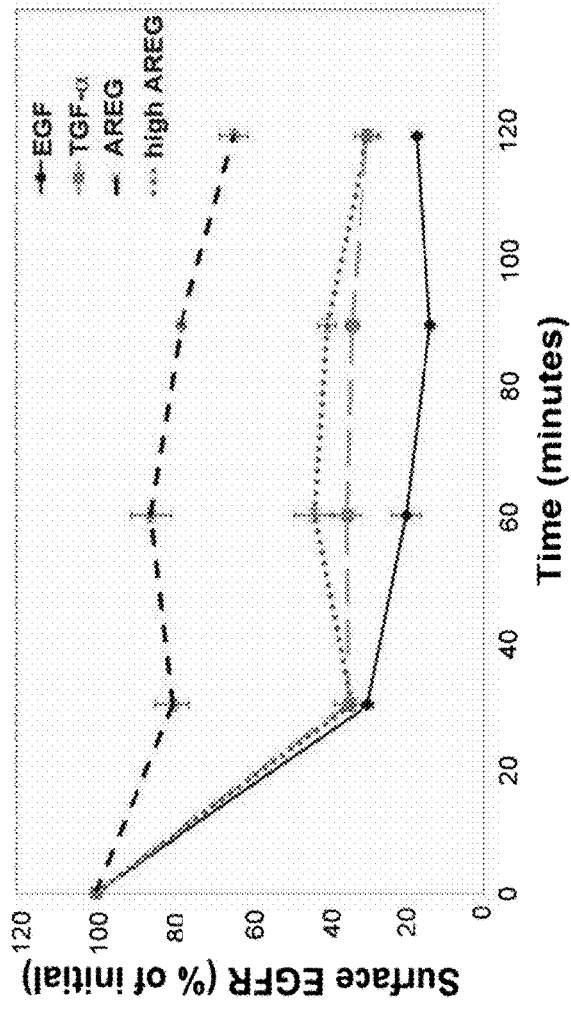
Figure 3A:
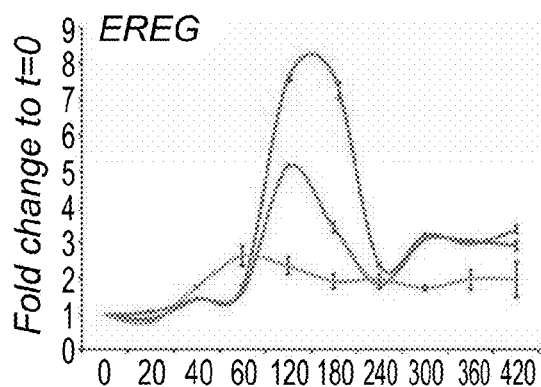
Figure 3D:
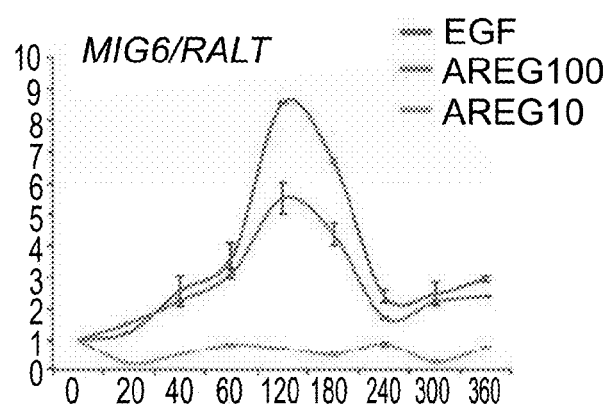
Figure 3B:
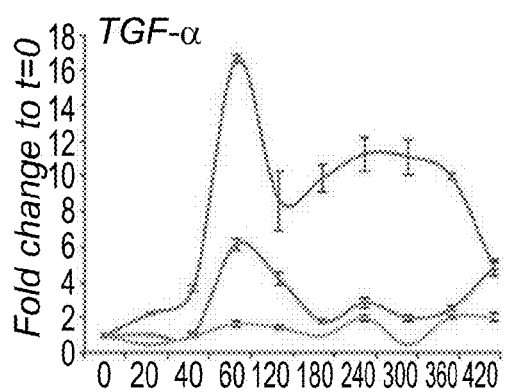
Figure 3E:
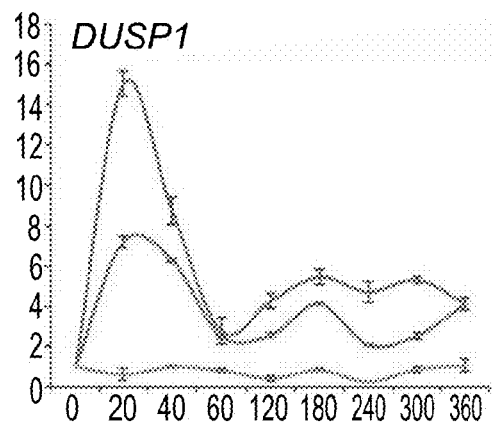
Figure 3C:
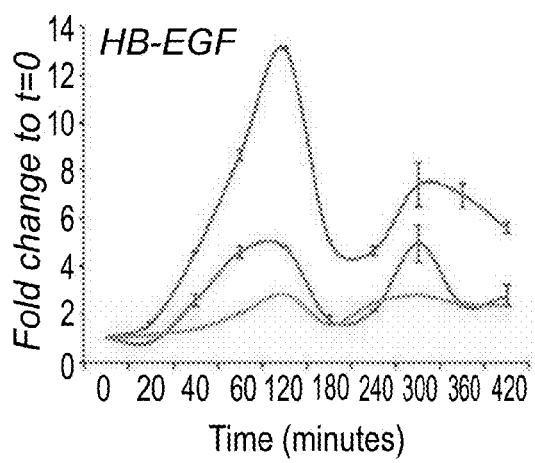
Figure 3F:
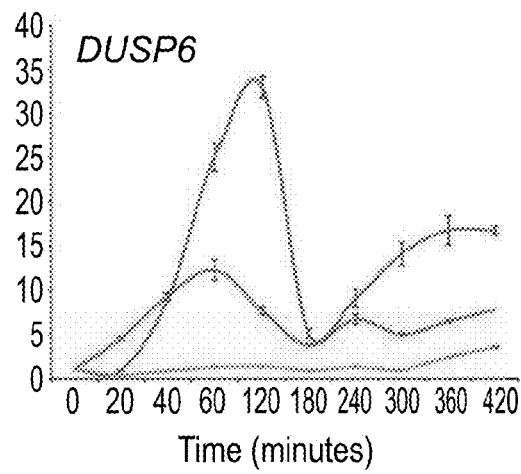

FIGS. 2G-2H illustrate that AREG is a low affinity ligand able to induce only limited receptor downregulation in normal epithelial cells. FIG. 2G is a graph illustrating results of the immortalized human mammary cell line MCF10A used for ligand displacement assays. Cells were plated in 12 well plates and incubated for 3 hours on ice with a radio-labeled EGF ($^{125}$I-EGF; 50 ng/mL) in the absence or presence of increasing concentrations of a competing unlabeled ligand, as indicated. The cells were later washed and lysed, and the associated radioactivity was determined. The extent of ligand displacement (mean±range of triplicates) is depicted; and FIG. 2H is a graph illustrating results of MCF10A cells grown in 12 well plates and starved overnight for serum factors. On the following day the cells were either kept in starvation medium (control) or they were stimulated for the indicated time intervals with EGF (1 ng/mL), TGF-alpha (1 ng/mL) or AREG (1 ng/mL or 100 ng/mL; denoted High). Next, EGFR downregulation was assayed, on ice, using a 60 minute incubation with a radioactive EGF ($^{125}$I-EGF; 50 ng/mL). The cells were later washed, lysed in 1N NaOH and their radioactivity was determined. Averages of triplicates and S.D. values (bars) are presented.

FIGS. 3A-3F illustrate that amphiregulin acts as a weak inducer of transcription-mediated feedback regulatory loops of EGFR signaling. MCF10A cells that were starved overnight for serum factors were treated with EGF (10 ng/ml) or AREG (10 or 100 ng/ml) for the indicated time intervals. qPCR analysis was performed using primers corresponding to mRNAs encoding either negative (MIG6/RALT, DUSP1 and DUSP6) or positive (EREG, TGF-alpha and HB-EGF) feedback regulatory components of the EGFR signaling pathways. Shown are mRNA profiles representative of two independent biological repeats.

Figure 4D:
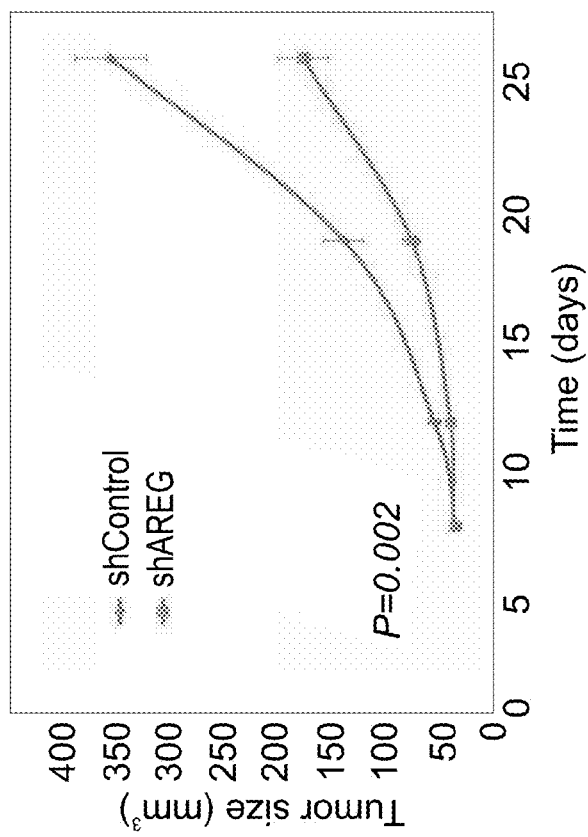
Figure 4C:
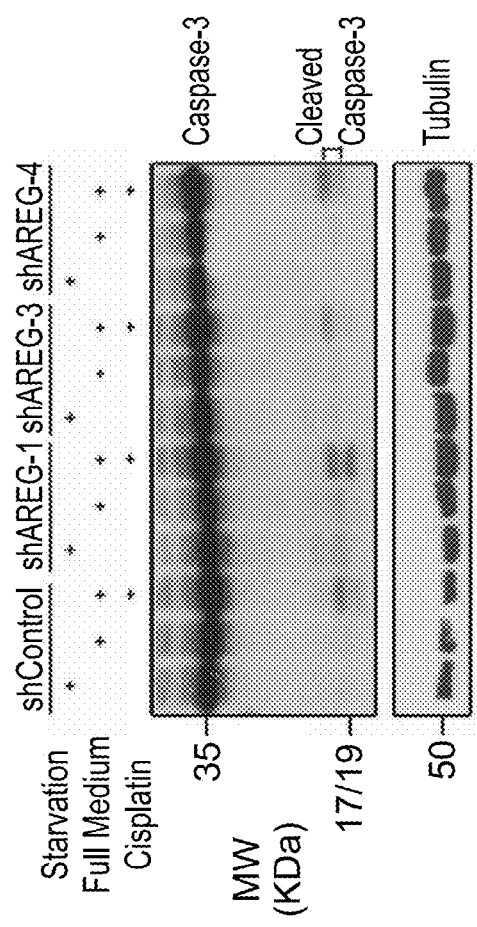

FIGS. 4A-4D illustrate that depletion of AREG expression inhibits tumorigenic growth of human ovarian cancer cells. FIG. 4A is a graph illustrating results of OVCAR5 ovarian cancer cells treated with lentiviral expression constructs, either a scrambled shRNA or an AREG-specific shRNA. Conditioned media were collected three days later and the levels of secreted AREG were assessed using ELISA; FIG. 4B is a graph illustrating the growth rates of shAREG or shControl OVCAR5 cells measured using the MTT assay. Shown are means±S.D. values of hexaplicates (*P<0.005, t-test); FIG. 4C is a photograph illustrating Caspase-3 cleavage as assessed using immunoblotting and OVCAR5 sub-lines stably expressing three different shAREGs, or shControl. The assay was performed either in full medium or under serum starvation. Overnight treatment with cisplatin (5 µg/mL) was used as a positive control. Note that the 35 kilodalton caspase-3 protein was cleaved only in cells incubated for 12 hours in the presence of cisplatin, but no shAREG mimicked this effect; and FIG. 4D is a graph illustrating tumor size. Female nude mice (6 weeks old; 10 per group) were inoculated subcutaneously with OVCAR5 ovarian cells ($3\times10^6$ per animal) pre-treated with either a scrambled shRNA or the AREG-specific shRNA. Tumor volumes were measured as indicated. Data points are presented as mean volume±S.D. values (*P<0.005, t-test).

Figures 4E, 4F:
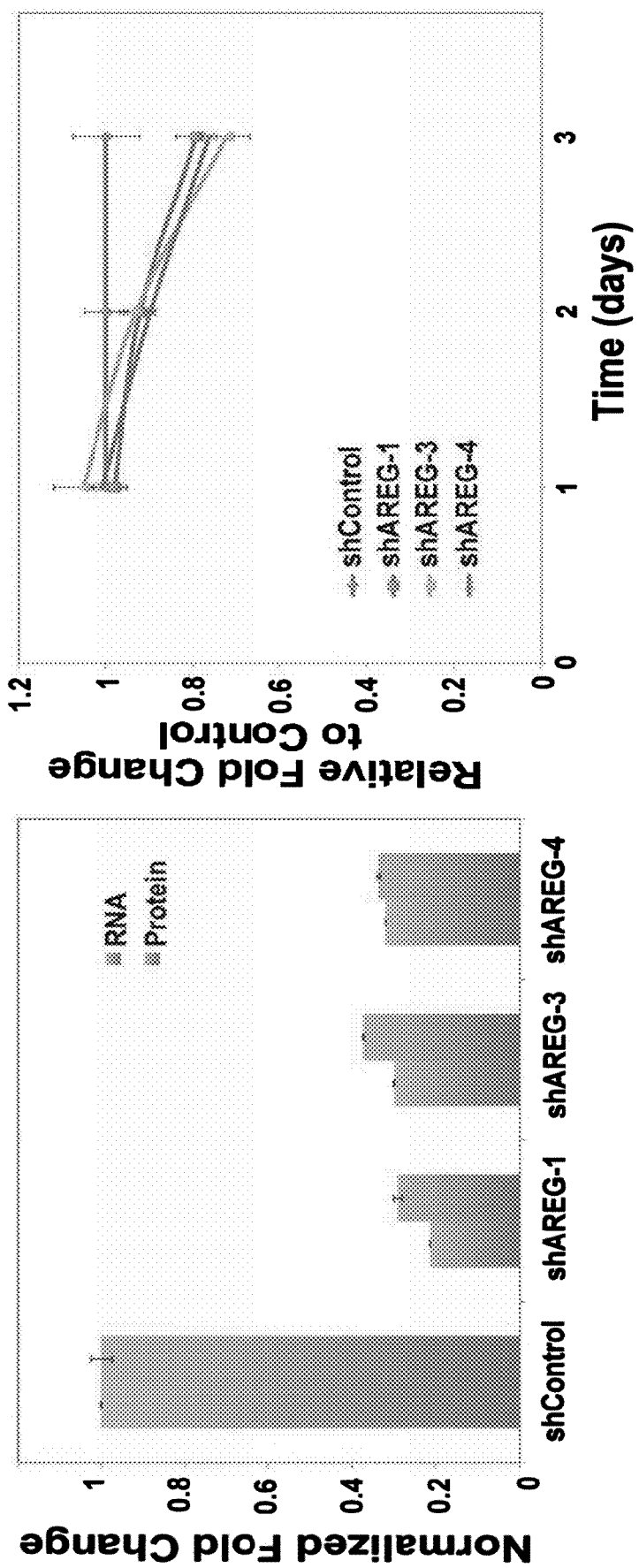
Figures 4G, 4H:
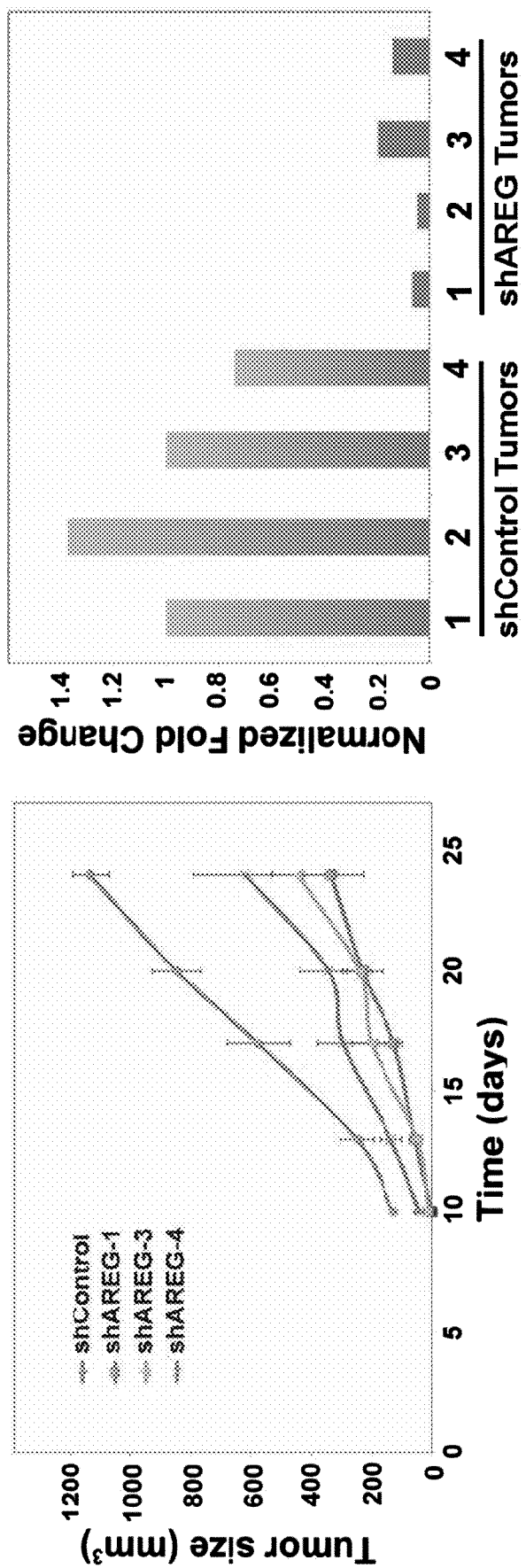

FIGS. 4E-4H illustrate that RNA hairpins specific to AREG inhibit growth of ovarian cancer cells in vitro and in animals. FIG. 4E is a graph illustrating OVCAR5 ovarian cancer cells treated with lentiviral expression constructs, either a scrambled shRNA (shControl) or AREG-specific shRNAs. Analysis of the efficacy of knockdown was conducted using real-time PCR. Likewise, the corresponding effect on protein levels was assessed by applying ELISA on conditioned media collected over a period of three days. Each result represents a triplicate determination; FIG. 4F is a graph illustrating the growth rates of the three different shAREG, or shControl, stably expressed OVCAR5 sub-lines measured using the MTT assay. Shown are means±S.D. values of hexaplicates; FIG. 4G is a graph illustrating the results of female nude mice (6 weeks old; 5 animals per group) inoculated subcutaneously with OVCAR5 ovarian cancer cells ($3\times10^6$ per animal), pre-treated with either a scrambled shRNA (shControl) or one of the three AREG-specific shRNA. Tumor volumes were measured at the indicated time intervals. Data points are presented as mean volume±S.D. values; and FIG. 4H is a graph illustrating the results of OVCAR5 ovarian cancer cells treated with lentiviral expression constructs, either a scrambled shRNA (shControl) or AREG-specific shRNAs. Each cell line was then inoculated into the flank of immunocompromised mice. The tumors that formed were removed, fixed in paraffin and RNA was extracted. Analysis of the efficacy of knockdown was conducted using real-time PCR and palpable tumors. Note that the differences in AREG expression were maintained in the xenografts.

Figure 5A:
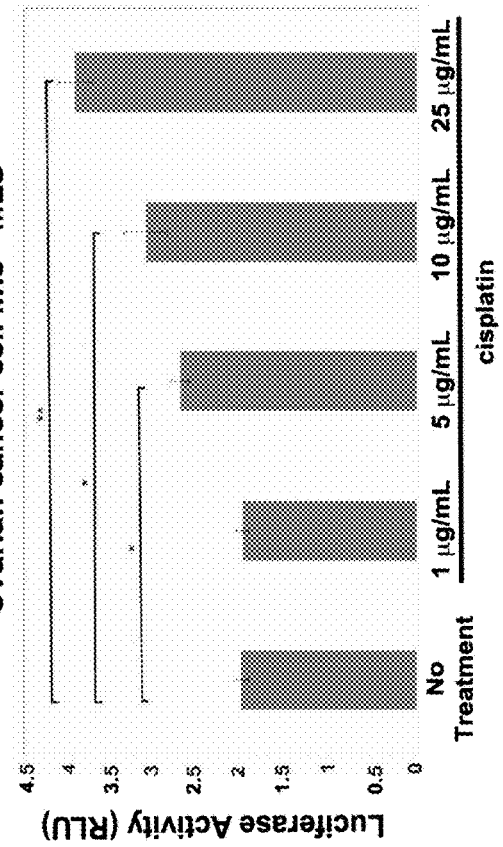
Figure 5B:
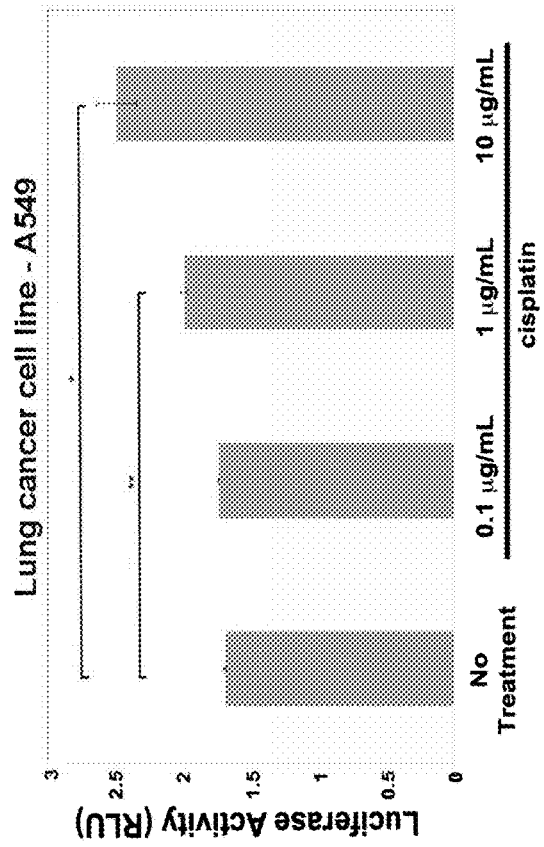

FIGS. 5A-5B illustrate transcriptional activation of the AREG promoter by cisplatin. FIG. 5A is a graph illustrating the results of MLS cells transfected with a luciferase reporter containing the promoter region of AREG. Luciferase activity derived from the *Renilla* luciferase, was determined and normalized to that derived from the firefly luciferase reporter. Twenty-four hours after transfection, increasing concentrations of cisplatin were added and 48 hours later the cells were subjected to luciferase assay; and FIG. 5B illustrates the results of A549 lung cancer cells treated as in FIG. 5A. Averages of triplicates and S.D. values (bars) are presented (*P<0.03, **P<0.01, t-test).

Figure 5D:
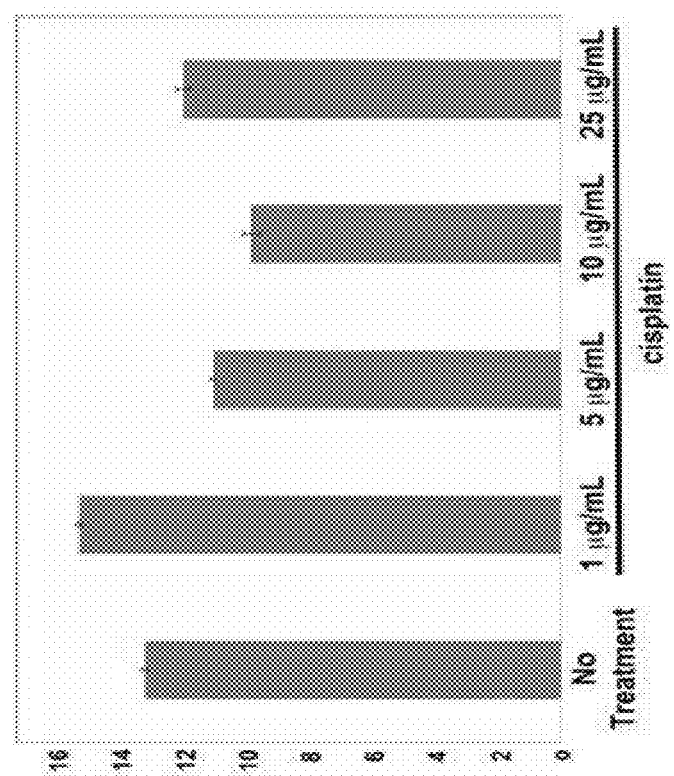
Figure 5C:
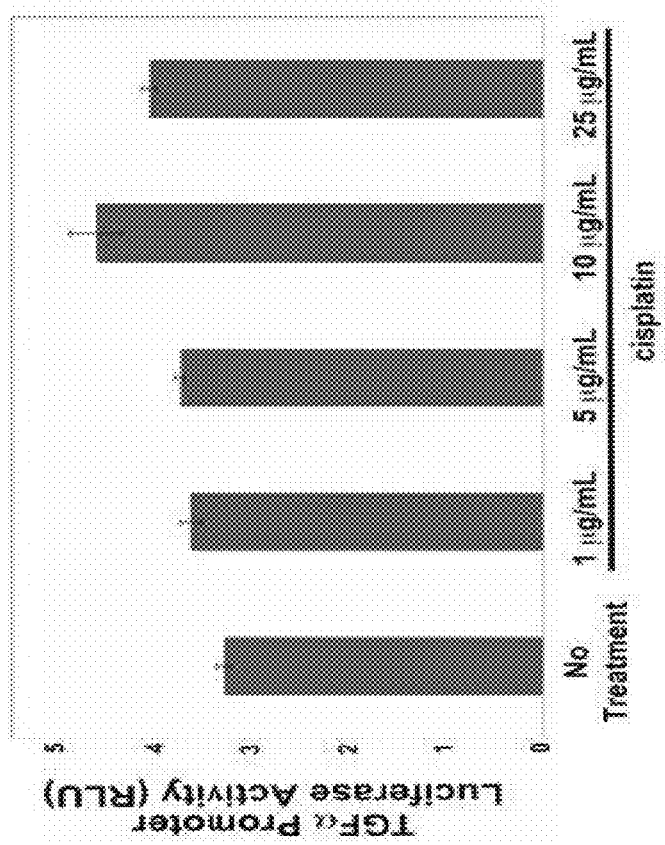
Figure 5F:
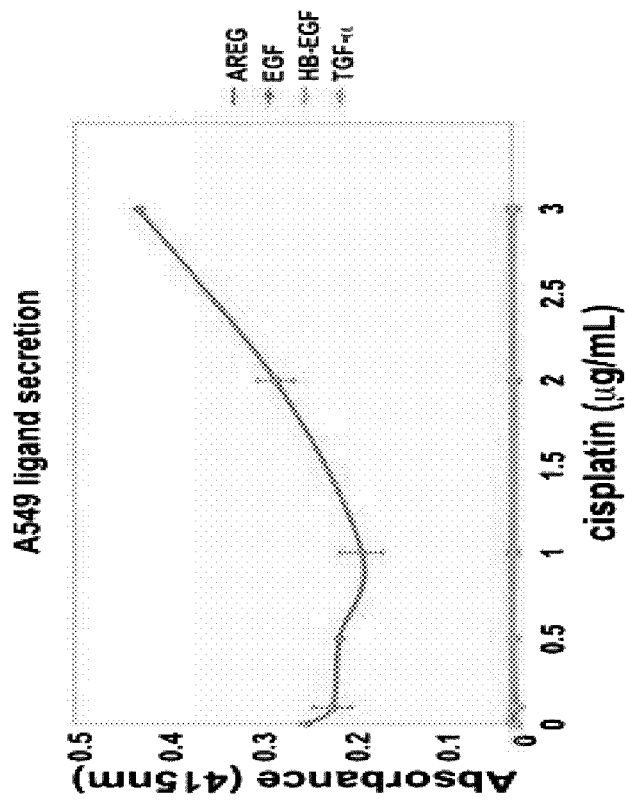
Figure 5E:
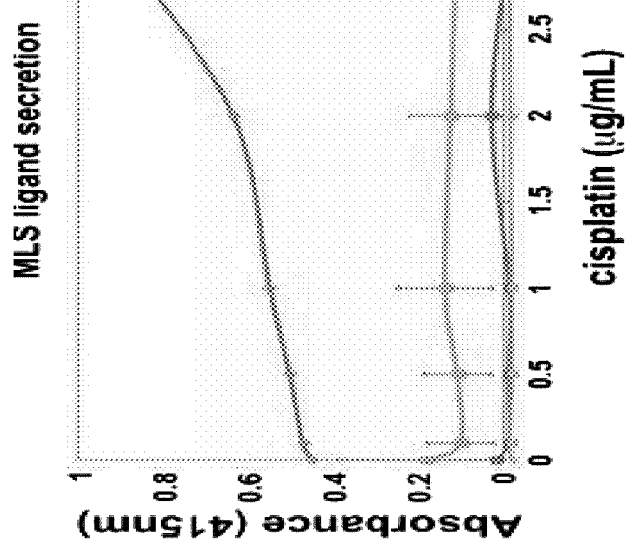

FIGS. 5C-5F illustrate that AREG, unlike HB-EGF and TGF-alpha, undergoes up-regulation in response to a chemotherapeutic agent. FIG. 5C is a graph illustrating results of MLS cells transfected with a luciferase reporter containing the promoter region of TGF-alpha. The luciferase activity derived from the *Renilla* luciferase was normalized to that derived from the firefly luciferase (co-transfection control). Twenty-four hours after transfection, increasing concentrations of cisplatin were added, and 24 hours later the cells were subjected to luciferase assays; FIG. 5D is a graph illustrating assessment of GAPDH promoter activity as described in FIG. 5C; FIG. 5E is a graph illustrating the results of MLS ovarian cancer cells exposed to increasing concentrations of cisplatin. Cells were assessed for the secretion of the indicated ligands using ELISA; and FIG. 5F is a graph illustrating assessment of the A549 lung cancer cell line analyzed as in FIG. 5E.

Figure 6E:
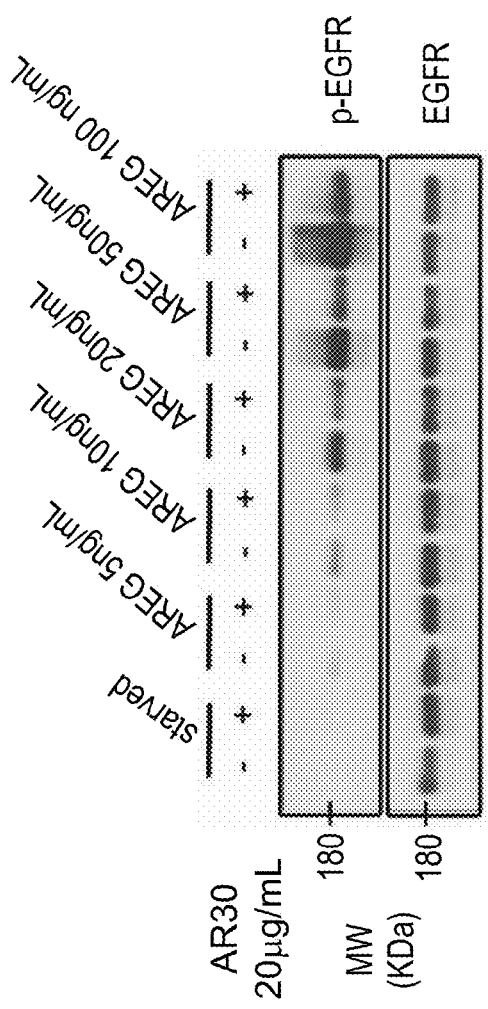
Figure 6D:
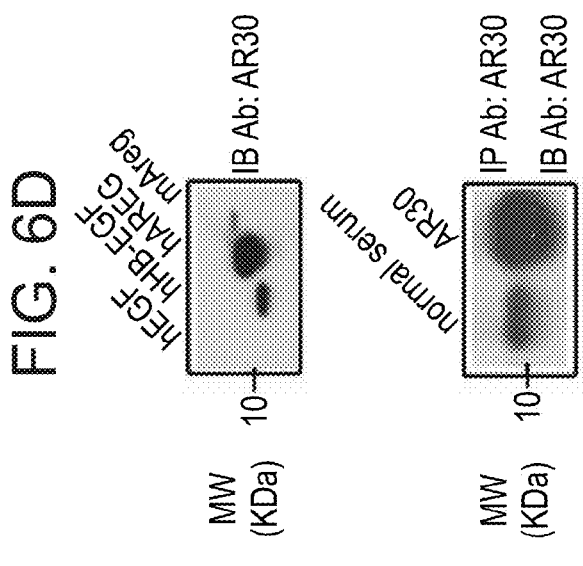

FIGS. 6A-6F illustrate AR30, an anti-AREG monoclonal antibody, that inhibits auto-phosphorylation of EGFR. FIG. 6A is a photograph of a Coomassie blue staining of an acrylamide gel showing a purified fraction of AREG isolated from bacteria and purified on a NiNTA column. The molecular weight marker lane indicates a 15 kilodalton band; FIG. 6B, cells were seeded in a 24 well plate, washed and incubated with increasing concentrations of the purified TRX-AREG fusion protein (8.5, 85, 850, 8500 ng/ml). EGF (10 ng/ml) was used as a positive control. Following a 10-min long incubation, the cells were lysed and cleared extracts immunoblotted (IB) with an anti-phosphotyrosine antibody (PY-99); FIG. 6C, 96 well plates were coated with the indicated ligands (0.1 μg/ml), and then incubated for 3 hours with three different mAbs specific to AREG. Thereafter, wells were incubated for two hours with an anti-mouse antibody conjugated to HRP, followed by a 30 minutes incubation with ATBS. Signals were determined using an ELISA reader (set at 420 nm); FIG. 6D, human EGF, HB-EGF and AREG, as well as murine AREG, were immunoblotted (IB) with the AR30 mAb, either directly (upper panel) or following immunoprecipitation (IP) using the same antibody (lower panel). Serum from non-immunized mice was used as a negative control; FIG. 6E, HeLa cells were pre-incubated with (or without) mAb AR30 (20 μg/mL) and increasing concentrations of AREG. Thereafter, whole cell lysates were immunoblotted (IB) using an antibody specific to the phosphorylated form of EGFR (tyrosine 1068) or an antibody to EGFR; and FIG. 6F, HeLa cells were incubated with (or without) AREG (100 ng/mL) in the presence of increasing concentrations of mAb AR30 (5, 10, 20 and 50 μg/mL). Thereafter, cells were lysed and cleared extracts immunoblotted (IB) using the indicated antibodies.

Figure 7A:
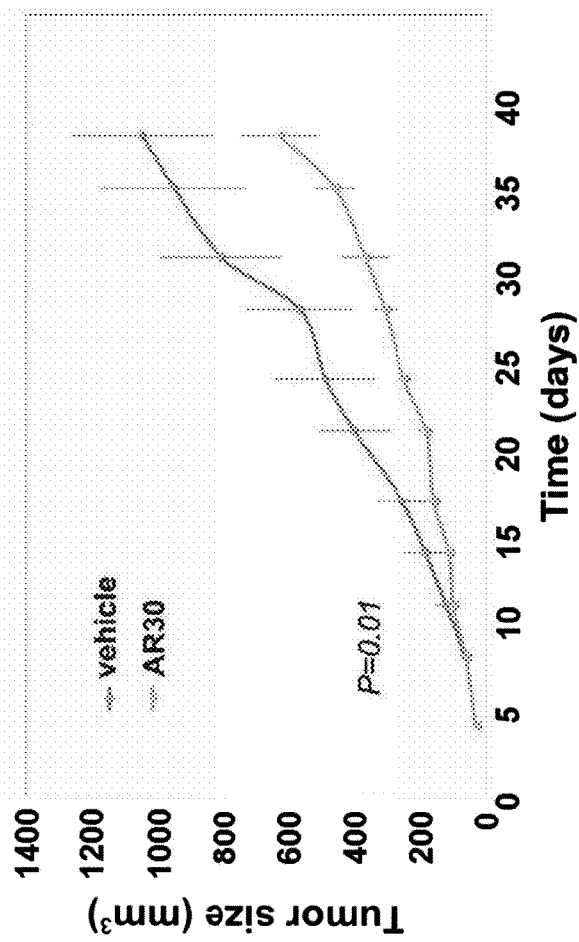
Figure 7B:
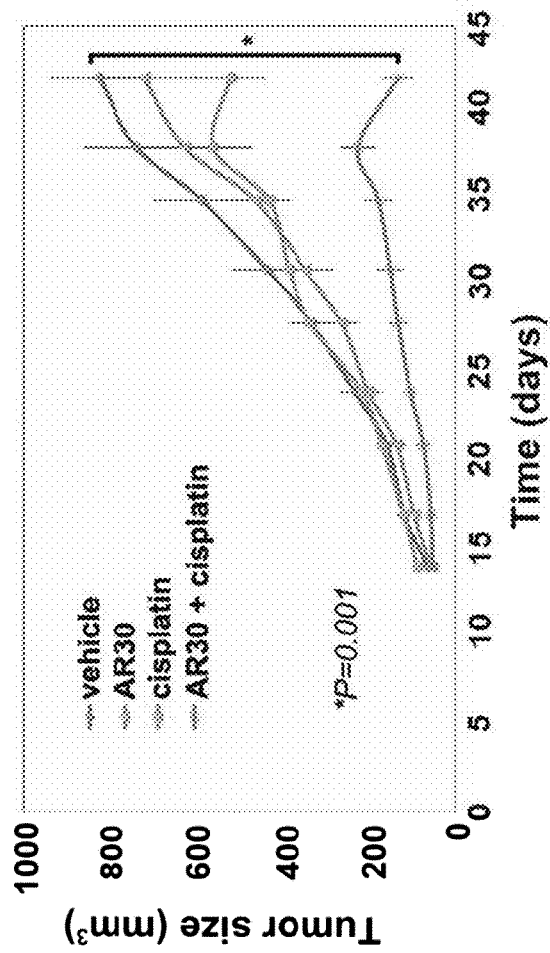
Figure 7C:
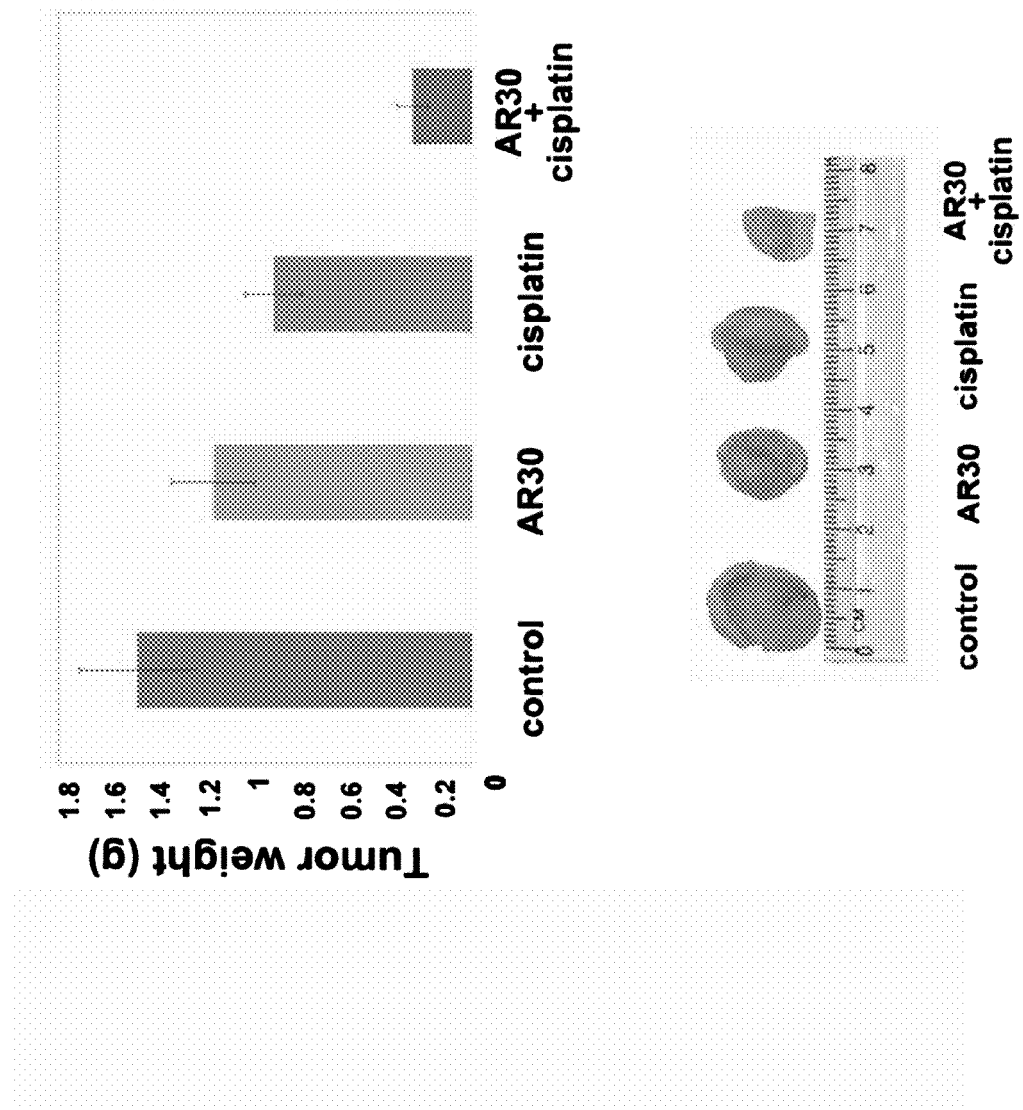

FIGS. 7A-7C illustrate that AR30, an anti-AREG monoclonal antibody, inhibits tumorigenic growth of human ovarian cancer cells in mice. FIG. 7A, female nude mice (6 weeks old) were inoculated subcutaneously with MLS ovarian cancer cells ($2 \times 10^6$ per animal). Once tumors became palpable, mice were randomized into two groups. Eleven mice were injected intraperitoneally with an anti-AREG mAb (AR30; 200 μg/mouse; twice a week, on days: 8, 11, 14, 17, and 21). The control group also included 11 mice. Shown are means±S.D. values; FIG. 7B, female nude mice (6 weeks old) were inoculated subcutaneously with MLS ovarian cancer cells ($2 \times 10^6$ per animal). Once tumors became palpable, mice were randomized into four groups. One group (8 mice) was injected intraperitoneally with the AR30 mAb (100 μg/mouse twice a week, on days: 8, 14, 17, 21, 24 and 28). Another group (8 mice) was treated with cisplatin (5 mg/kg; on days 8 and 21). The fourth group was treated with a combination of mAb AR30 and cisplatin. The control group included 12 mice; and FIG. 7C, the indicated MLS tumors were excised, and their average weights determined. Representative tumors were photographed.

Figure 8:
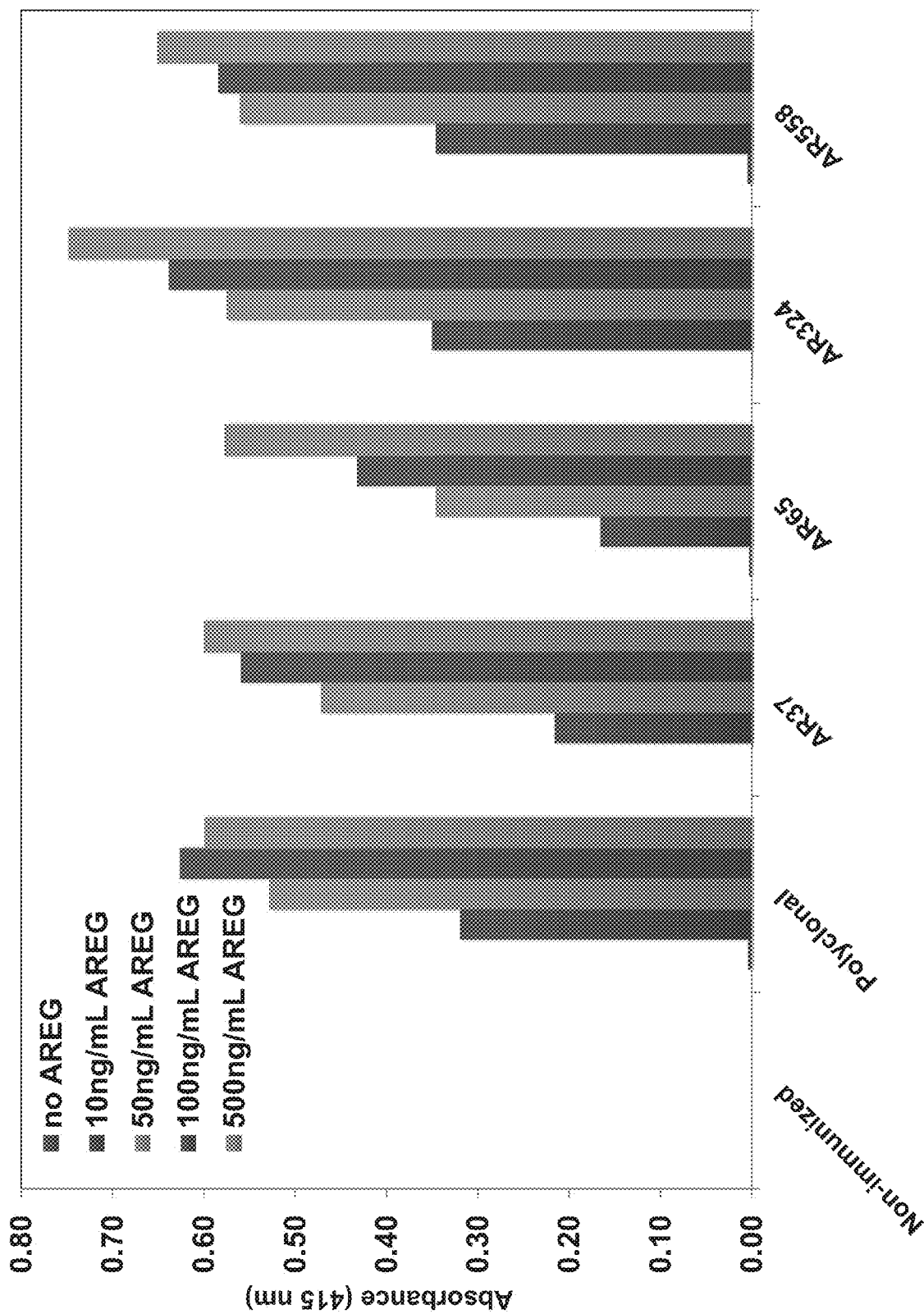

FIG. 8 illustrates the specificity tests of anti-AREG monoclonal antibodies. 96 well plates were coated with human AREG at the indicated concentrations, and then incubated for 2 hours with 4 different mAbs specific to AREG (as indicated). Thereafter, wells were incubated for two hours with an anti-mouse antibody conjugated to HRP, followed by a 30 minute incubation with ATBS. Signals were determined using an ELISA reader (set at 415 nm).

Figure 9A:
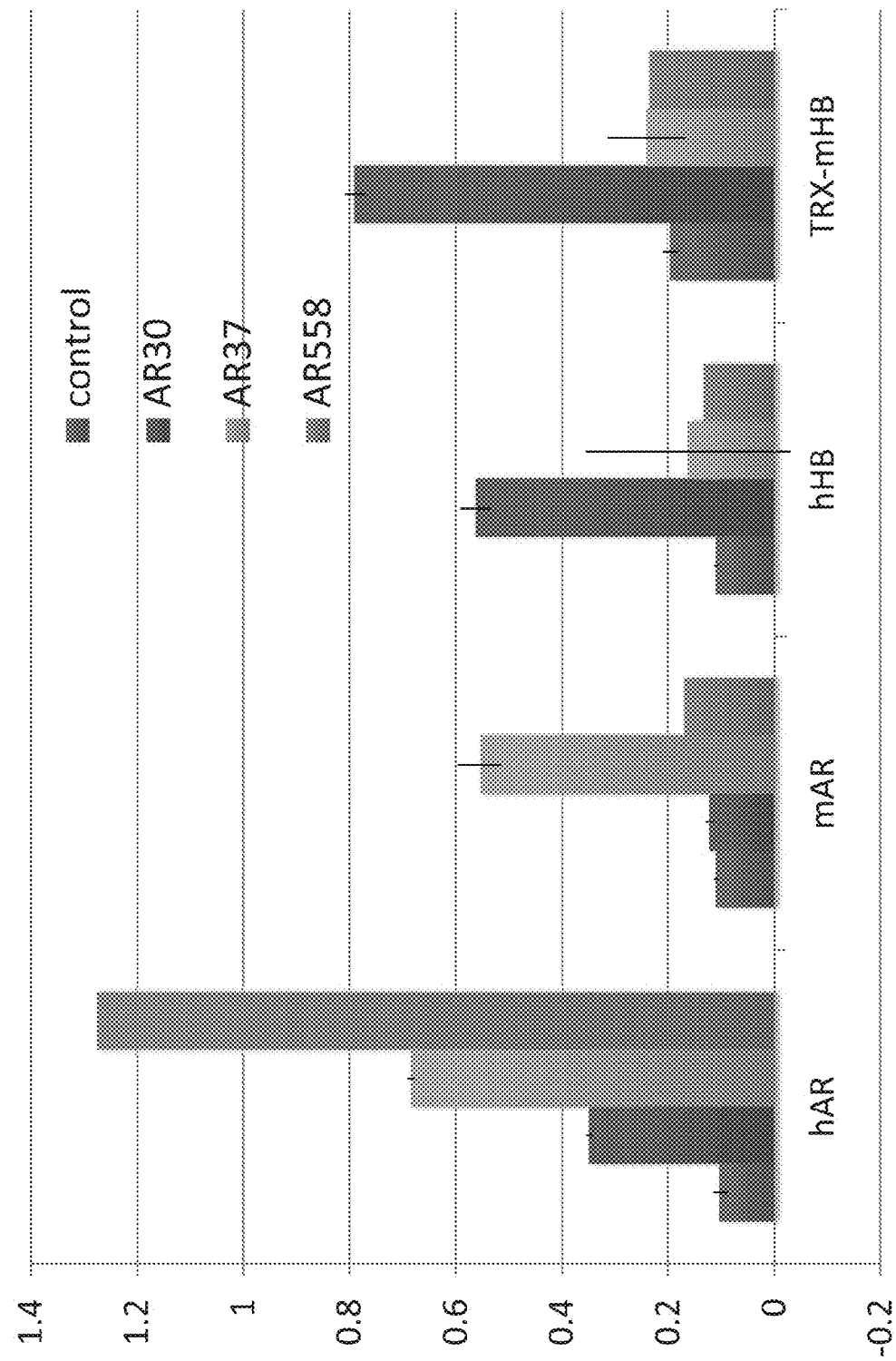
Figure 9B:
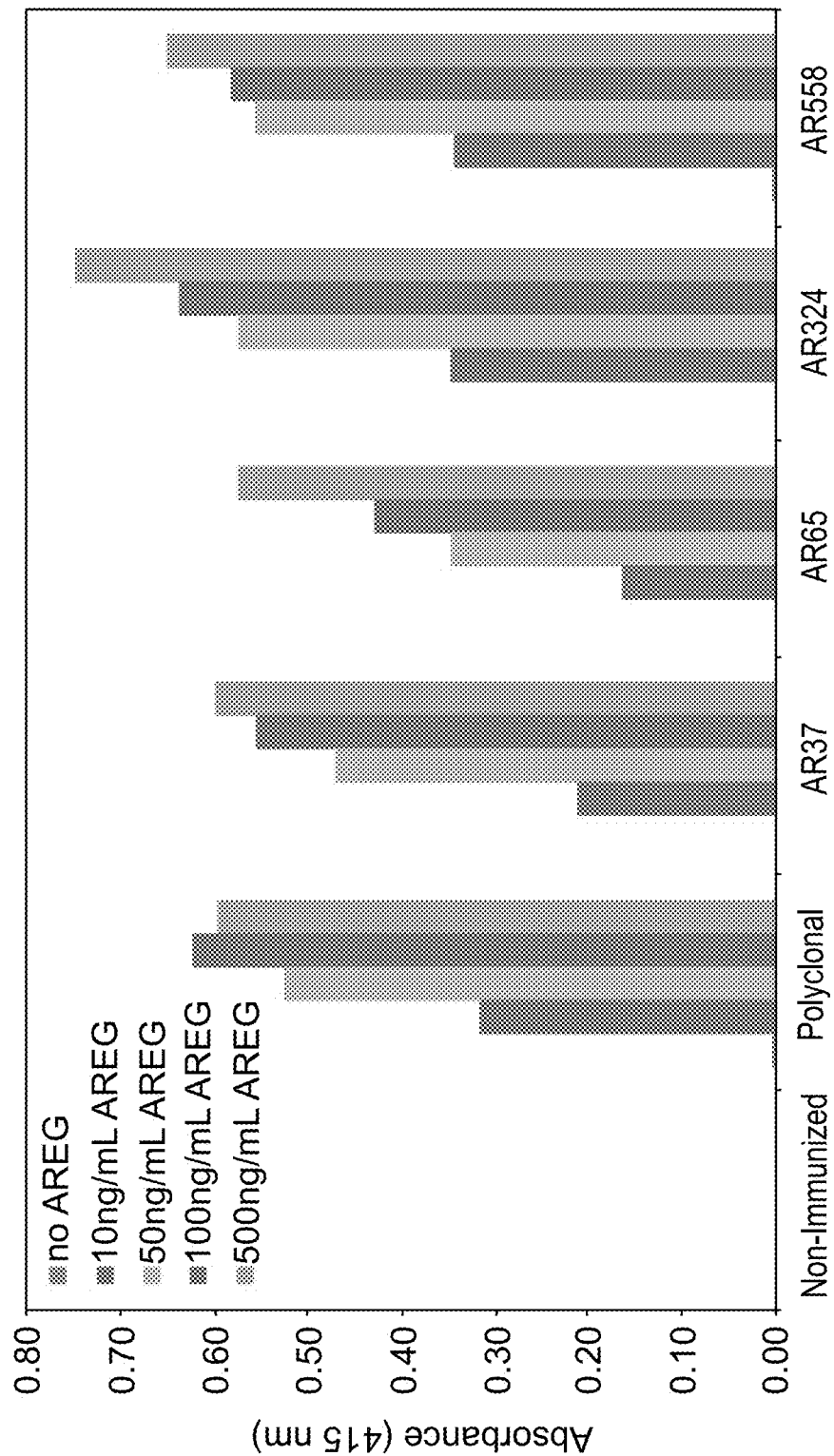
Figure 9C:
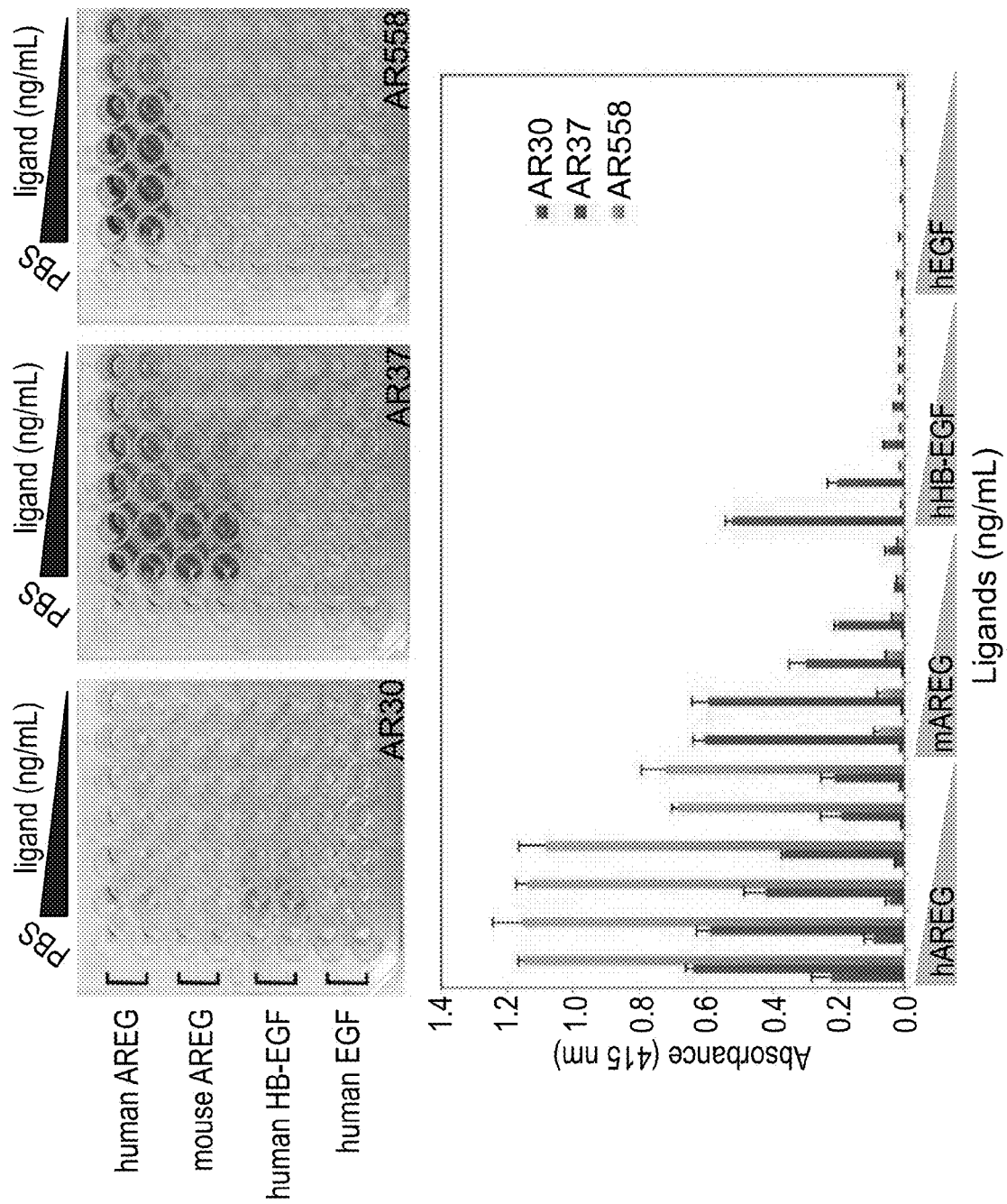

FIGS. 9A-9C illustrate specificity of the anti-AREG mAbs.

FIG. 9A—96 well plates were coated with the indicated ligands (400 ng/mL), including a murine HB-EGF fused to thioredoxin. Plates were incubated for 2 hours with 3 different mAbs specific to AREG (as indicated). Thereafter, wells were incubated for two hours with an anti-mouse antibody conjugated to HRP, followed by a 30 minute incubation with ATBS. Signals were determined using an ELISA reader (set at 415 nm). FIG. 9B—shows specificity tests of anti-AREG monoclonal antibodies: 96-well plates were coated with human AREG at the indicated concentrations, and then incubated for 2 hours with 4 different mAbs specific to AREG. Thereafter, wells were incubated for two hours with an anti-mouse antibody conjugated to HRP, followed by a 30-min incubation with ATBS. Signals were determined using an ELISA reader (set at 415 nm). FIG. 9C—shows species specificity of the anti-AREG mAbs. 96-well plates were coated with decreasing concentrations (400, 200, 100, 50, 25 and 10 ng/mL) of the indicated 3 ligands, and then incubated for 2 hours with three different mAbs specific to AREG (AR30, AR37 and AR558) at 1pg/mL. Thereafter, wells were incubated for two hours with an anti-mouse antibody conjugated to HRP, followed by a 20-min incubation with ATBS. Signals were determined using an ELISA reader (set at 420 nm).

Figure 10A:
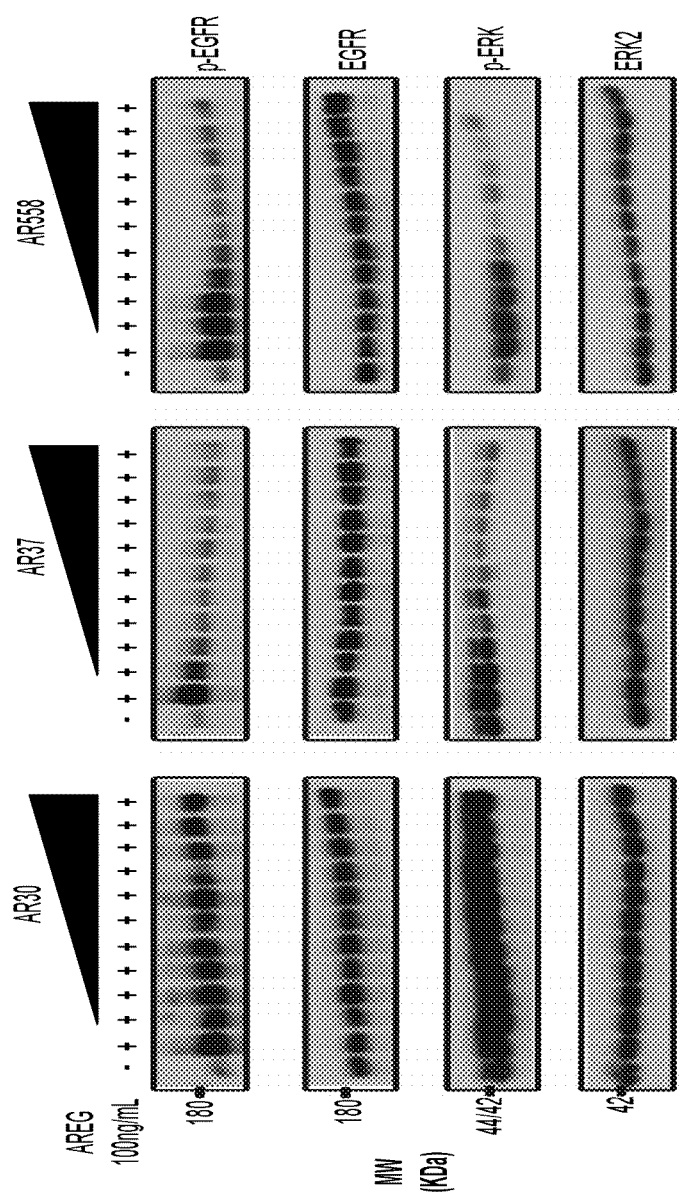

FIG. 10A illustrates that anti-AREG mAbs inhibit ligand-induced activation of EGFR. HeLa cells were incubated with (or without) AREG (100 ng/ml) in the presence of increasing concentrations of mAb AR30, mAb AR 37 or mAb AR558 (0.1, 0.2, 0.5, 0.75, 1.5, 3.5, 6.25, 12.5, 25 and 50 μg/ml). Thereafter, cells were lysed and cleared extracts immunoblotted (IB) using the indicated antibodies, including an antibody specific to the phosphorylated (active) for of EGFR (pEGFR).

Figure 10B:
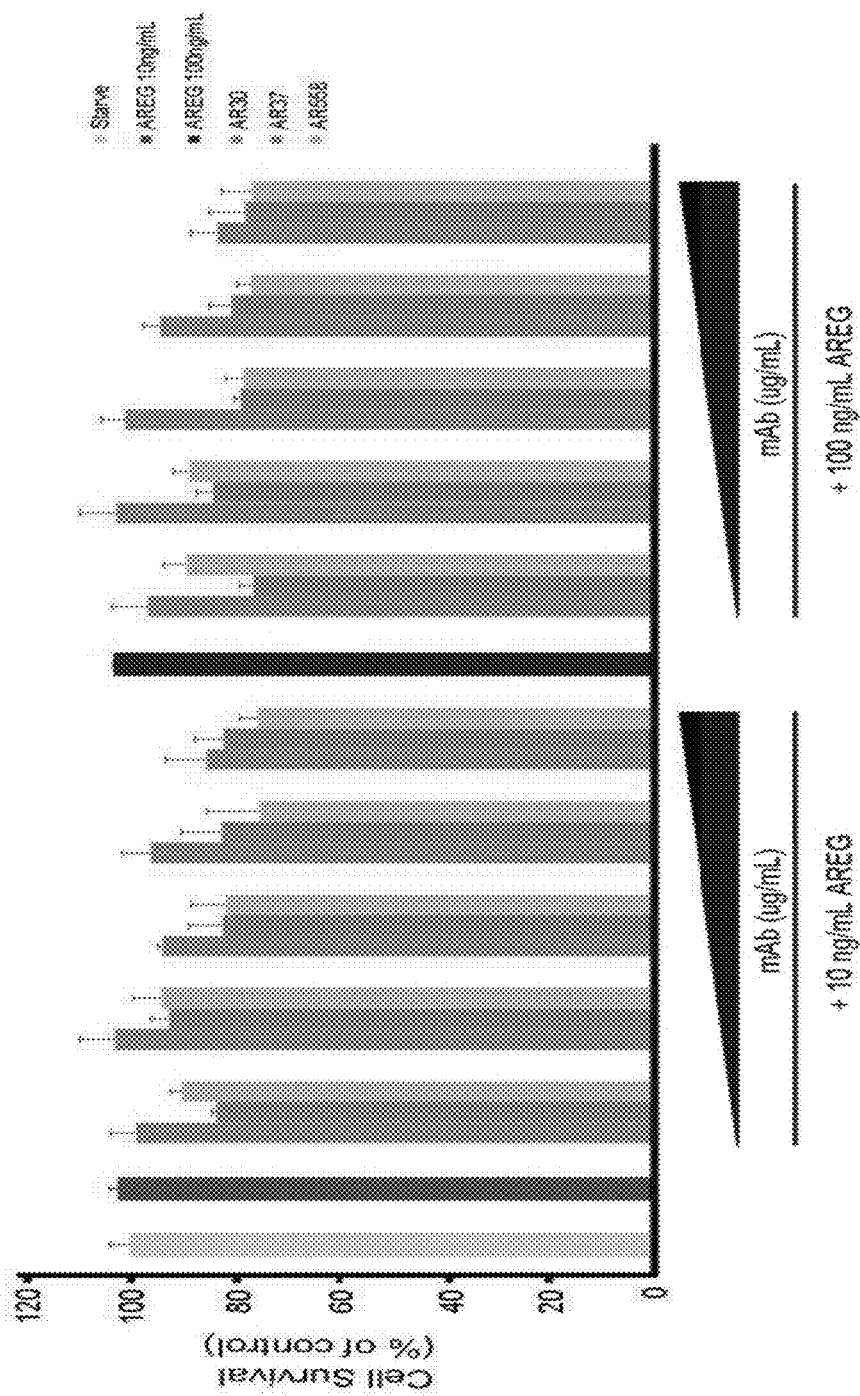

FIG. 10B illustrates that anti-AREG monoclonal antibodies moderately inhibit proliferation of MCF10A cells. Proliferation assays using MTS were performed on MCF10A cells (1,000 cells per well). C ells were plated on the day before and treated for 72 h with the indicated mAbs (1, 5, 10, 20 or 50 ug/mL). Increasing concentrations of the indicated mAbs (either alone or in combination with AREG) were used in medium supplemented with 1% serum and AREG (either at 10 or 100 ng/mL).

Figure 11:
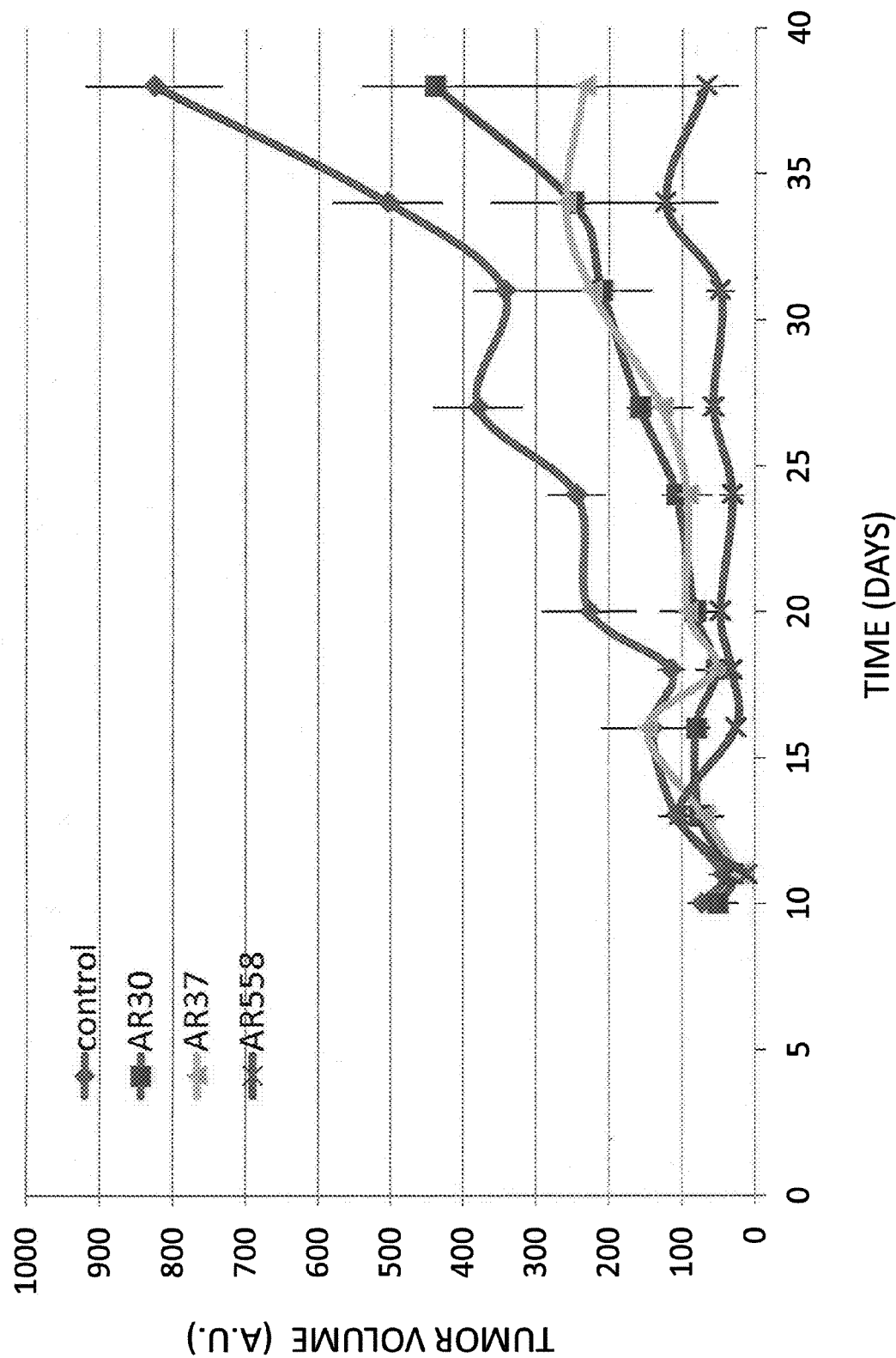

FIG. 11 illustrates that anti-AREG antibodies effectively inhibit tumor growth in mice. Female nude mice were inoculated subcutaneously with Cal-27 human head and neck cancer cells ($2 \times 10^6$). Once tumors became palpable (5-7 days) mice were randomized and intraperitoneally injected with saline (Control), or with anti-AR mAbs: AR30, AR37 or AR558 (each at 300 μg per injection). Mice were treated with mAbs twice a week and tumor volume was followed. Shown are averages and SD values from at least 5 mice per group.

DESCRIPTION OF SPECIFIC EMBODIMENTS OF THE INVENTION

The present invention, in some embodiments thereof, relates to anti-amphiregulin antibodies, compositions comprising same and uses thereof.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Amphiregulin (AREG), an EGF-family ligand, plays pivotal roles in many cellular processes including in mammary gland development, in oocyte maturation, in branching and morphogenesis occurring within epithelial tissues, such as lung, prostate and kidney. Conversely, AREG has also been linked to the oncogenic process in various cancers including prostate, hepatocellular, pancreatic, breast, lung, colon, and head and neck tumors, in which AREG expression has been associated with worse prognosis.

While reducing the present invention to practice, the present inventors have uncovered that AREG expression is high in ascites and pleural fluids of advanced ovarian and lung cancer patients, respectively, relative to other EGF family ligands (Example 1 of the Examples section which follows). The results illustrate that the high levels of AREG reflect two processes: firstly, induction of AREG transcription following patient treatment with genotoxic drugs (Example 6 of the Examples section which follows), and, secondly, inefficient AREG clearance by means of receptor endocytosis (Example 2 of the Examples section which follows). The present inventors have shown both in vitro and in vivo that AREG silencing forms significantly smaller tumors relative to control cells (Example 5 of the Examples section which follows). The present inventors have now generated novel anti-AREG monoclonal antibodies (denoted AR30, AR37 and AR558). The present inventors have illustrated the anti-tumor effect of AR30, AR37 and AR558 (Examples 7 and 10 of the Examples section which follows). Furthermore, the use of an anti-AREG antibody greatly sensitized ovarian cancer cells to a chemotherapeutic agent. Specifically, the combination of cisplatin, a genotoxic drug commonly used in the treatment ovarian cancer patients, and AR30 almost completely inhibited ovarian tumor growth (Example 7 of the Examples section which follows). The novel antibodies AR37 and AR558 were generated in a unique amphiregulin knockout animal model. Utilizing this animal model the present inventors were able to generate antibodies which specifically target human AREG (AR558) and pan-antibodies (AR37) which recognizing both human and mouse AREG. The latter antibodies being specifically useful for testing efficacy and toxicity in mouse animal models. Taken together, these teachings illustrate the generation and the anti-tumor therapeutic potential of anti-AREG antibodies such as AR30, AR37 and AR558.

Thus, according to one aspect of the present invention there is provided a method of determining the suitability of a subject to a treatment with an anti-amphiregulin antibody, wherein the subject has a cancer selected from the group consisting of ovarian cancer, head and neck cancer and pancreatic cancer exhibiting resistance to chemotherapy, the method comprising: analyzing in a biological sample of the subject expression level of amphiregulin, transforming growth factor alpha (TGF-alpha) and heparin-binding epidermal growth factor (HB-EGF), wherein a level of expression of the amphiregulin above a predetermined threshold and no expression of the TGF-alpha and/or the HB-EGF or an expression below a predetermined level of the TGF-alpha and/or the HB-EGF is indicative of the suitability of the subject to treatment with the anti-amphiregulin antibody.

As used herein, the term "subject" refers to a mammalian e.g., human subject, of any age or gender who has been diagnosed with cancer. The subject is typically one having being diagnosed with cancer, with or without metastasis, at any stage of the disease.

According to a specific embodiment, the subject is diagnosed with ovarian, pancreatic or head and neck cancer and exhibits resistance to chemotherapy.

As used herein, the terms "resistant" or "resistance" with respect to a chemotherapeutic agent, refers to a subject who is suffering from a cancer which fails to respond to treatment with a chemotherapeutic agent(s) for a time of greater than 6 months or more, or whose tumor(s) progresses within 6 months of completion of treatment with a chemotherapeutic agent(s).

According to specific embodiments the resistance is an acquired resistance.

As used herein the term "acquired resistance" refers to progression of resistance following initial positive response to therapy (e.g. chemotherapy).

As used herein the term "cancer" refers to any cancerous disease. According to a specific embodiment the cancer depends on amphiregulin (activity and/or expression) for onset and/or progression. Cancer cells may be associated with phenotypes such uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor, such cells may exist locally within an animal (e.g. solid tumor), alternatively, cancer cells may circulate in the blood stream as independent cells, for example, leukemic cells (non-solid tumor), or may be dispersed throughout the body (e.g. metastasis). It will be appreciated that the term cancer as used herein encompasses all types of cancers, at any stage and in any form.

Types of cancerous diseases amenable to treatment by the methods of some embodiments of the invention include benign tumors, warts, polyps, pre-cancers, and malignant tumors/cancers.

Specific examples of cancerous diseases which can be treated using the methods of the present invention include, but are not limited to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple *glomus* tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to a specific embodiment of this aspect of the present invention, the cancer comprises an ovarian cancer, a head and neck cancer or a pancreatic cancer.

As used herein, the phrase "ovarian cancer" refers to any cancerous growth arising in an ovary, including but not limited to, epithelial tumors, germ cell tumors, and sex cord-stromal tumors. The ovarian cancer includes tumors confined to the ovaries (classified as stage I); tumors which involve one or both ovaries with pelvic extension (classified as stage II); tumors which involve one or both ovaries with microscopically-confirmed peritoneal metastases outside the pelvis and/or regional lymph nodes metastasis (classified as stage III); distant metastasis beyond the peritoneal cavity (classified as stage IV); Liver capsule metastasis (considered stage III) and liver parenchymal metastasis (considered stage IV).

As used herein, the phrase "head and neck cancer" refers to any uncontrolled cell growth in the cells of the head and neck, e.g. in the lip, oral cavity, nasal cavity, paranasal sinuses, pharynx, and larynx. Exemplary head and neck cancers include, but are not limited to, squamous cell carcinomas of the head and neck, hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, salivary gland cancer.

As used herein, the phrase "pancreatic cancer" refers to a malignant neoplasm of the pancreas, including but not limited to, adenocarcinomas, adenosquamous carcinomas, signet ring cell carcinomas, hepatoid carcinomas, colloid carcinomas, undifferentiated carcinomas, undifferentiated carcinomas with osteoclast-like giant cells and islet cell carcinomas.

As mentioned, the cancer of some embodiments of the invention exhibits resistance to chemotherapy.

As used herein, the terms "chemotherapy" or "chemotherapeutic" refer to an agent that reduces, prevents, mitigates, limits, and/or delays the growth of neoplasms or metastases, or kills neoplastic cells directly by necrosis or apoptosis of neoplasms or any other mechanism, or that can be otherwise used, in a pharmaceutically-effective amount, to reduce, prevent, mitigate, limit, and/or delay the growth of neoplasms or metastases in a subject with neoplastic disease (e.g. cancer).

Chemotherapeutic agents include, but are not limited to, fluoropyrimidines; pyrimidine nucleosides; purine nucleosides; anti-folates, platinum agents; anthracyclines/anthracenediones; epipodophyllotoxins; camptothecins (e.g., Karenitecin); hormones; hormonal complexes; antihormonals; enzymes, proteins, peptides and polyclonal and/or monoclonal antibodies; immunological agents; *vinca* alkaloids; taxanes; epothilones; antimicrotubule agents; alkylating agents; antimetabolites; topoisomerase inhibitors; antivirals; and various other cytotoxic and cytostatic agents.

According to a specific embodiment, the chemotherapeutic agent includes, but is not limited to, abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

As used herein, the terms "platinum derivative", "platinum medicament" or "platinum compound" include all compounds, compositions, and formulations which contain a platinum ligand in the structure of the molecule. According to one embodiment, the valence of the platinum ligand contained therein may be platinum II or platinum IV. The platinum derivatives, medicaments or compounds disclosed in the present invention include, but are not limited to, cisplatin, oxaliplatin, carboplatin, satraplatin, and analogs and derivatives thereof.

As used herein, the term "taxane medicament" includes, but is not limited to, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof.

The chemotherapeutic agents of the invention may comprise standard as well as experimental chemotherapy drugs. The chemotherapeutic agents may also comprise a combination of more than one chemotherapy drug.

The term chemotherapy may also refer to other anticancer treatments such as radiotherapy, phototherapy and immunotherapy.

According to a specific embodiment, the cancer is ovarian cancer. According to another specific embodiment, the ovarian cancer is resistant to chemotherapy, e.g. to a platinum based chemotherapy and/or to a taxane chemotherapy. Such patients typically have a poor prognosis.

According to a specific embodiment, the subject is diagnosed with ovarian, pancreatic or head and neck cancer and exhibits an acquired resistance to chemotherapy.

As mentioned, determining the suitability of a subject to a treatment with an anti-amphiregulin antibody is carried out by analyzing in a biological sample of the subject expression level of amphiregulin and optionally transforming growth factor alpha (TGF-alpha) and/or heparin-binding epidermal growth factor (HB-EGF) (e.g., analyzing the levels of AREG, AREG and TGF-alpha, AREG and HB-EGF, or AREG and TGF-alpha and HB-EGF), wherein a level of expression of the amphiregulin above a predetermined threshold and no expression of the TGF-alpha and/or the HB-EGF or an expression below a predetermined level of the TGF-alpha and/or the HB-EGF is indicative of the suitability of the subject to treatment with the anti-amphiregulin antibody.

The term "amphiregulin" as used herein (also known as AREG or AR), refers to the gene product (i.e., mRNA or protein), e.g., human AREG, such as set forth in GenBank Accession Nos. NM_001657 or NP_001648.

The term "TGF-alpha" as used herein refers to the transforming growth factor-alpha (TGF-α) gene product (i.e., mRNA or protein), e.g., human TGF-alpha, such as set forth in GenBank Accession Nos. NM_003236, NM_001099691, NP_003227 or NP_001093161.

The term "HB-EGF" refers to the heparin-binding EGF-like growth factor (HB-EGF) gene product (i.e., mRNA or protein), e.g., human HB-EGF, such as set forth in GenBank Accession Nos. NM_001945 or NP_001936.

As described in the Examples section which follows, the present inventors have uncovered that AREG expression level is high in biological samples of advanced ovarian and lung cancer patients relative to other EGF family proteins (Example 1 of the examples section which follows) and that ovarian cancer cells secrete up-regulated levels of AREG following treatment with chemotherapeutic drugs (Example 6 of the examples section which follows).

As used herein, the "expression level" when relating to amphiregulin, TGF-alpha and HB-EGF refers to an intracellular, cell membranal, cell surface and/or cell-proximal amount of same (e.g. mRNA or polypeptide).

According to one embodiment, the term expression level relates to the secreted (e.g. from a cell) level of amphiregulin, TGF-alpha and/or HB-EGF.

In order to select a subject suitable for treatment, a biological sample is first analyzed for amphiregulin and optionally TGF-alpha and/or HB-EGF expression level.

In cases where the analysis is performed in vitro, the biological sample is obtained from the subject prior to analysis thereof.

Such a biological sample includes, but is not limited to, body fluids such as whole blood, serum, plasma, cerebrospinal fluid, urine, lymph fluids, ascites fluids or pleural fluids; and various external secretions of the respiratory, intestinal and genitourinary tracts, tears, saliva, milk as well as white blood cells, malignant tissues, amniotic fluid and chorionic villi.

According to one embodiment the sample comprises a biopsy sample. A biopsy sample may comprise a fluid sample (e.g. lymph fluids, ascites fluids or pleural fluids) or a cell sample (e.g. tissue sample).

Thus, according to an embodiment, the sample may comprise cells including, but not limited to blood cells, bone marrow cells, pancreatic cells, lung cells, hepatic cells, spleen cells, kidney cells, cardiac cells, ovarian cells, breast tissue cells, skin cells (e.g., epithelial cells, fibroblasts, keratinocytes), lymph node cells. According to a specific embodiment the cells comprise cancer cells. According to one embodiment, the cells are cancer cells circulating in the blood (e.g. circulating tumor cells (CTCs)).

According to a specific embodiment, the biological sample is ascites fluid, pleural fluid or blood. According to a specific embodiment, the biological sample is ascites fluid or pleural fluid.

Biological samples can be obtained using methods known in the art, including, but not limited to, blood test, fine needle biopsy, needle biopsy, core needle biopsy and surgical biopsy (e.g., brain, pancreatic or liver biopsy), buccal smear and lavage.

It will be appreciated that the methods of some embodiments of the invention may be implemented in vivo or in situ using detection methods suitable for the human body (e.g. using antibodies, such as the antibodies described in detail below, e.g. conjugated to a label or to a detectable moiety).

Amphiregulin, TGF-alpha and/or HB-EGF expression level can be detected in the biological sample using any structural, biological or biochemical method which is known in the art for detecting the expression level of the RNA encoding amphiregulin, TGF-alpha and/or HB-EGF (using e.g., Northern Blot analysis, RT-PCR analysis, RNA in situ hybridization stain, In situ RT-PCR stain) or the amphiregulin, TGF-alpha and/or HB-EGF protein itself (using e.g., Western blot, Enzyme linked immunosorbent assay (ELISA), Radio-immunoassay (RIA), Fluorescence activated cell sorting (FACS), Immunohistochemical analysis). Alternatively, amphiregulin, TGF-alpha and/or HB-EGF expression level can be detected in vivo using non-invasive optical imaging techniques (e.g. using SPECT and/or CT imaging techniques).

According to some embodiments of the invention, detection of the expression level of the Amphiregulin, TGF-alpha and/or HB-EGF protein(s) is performed by contacting the biological sample, the cell, or fractions or extracts thereof with an antibody (e.g. monoclonal antibody) which specifically binds to a polypeptide expressed from Amphiregulin, TGF-alpha and/or HB-EGF. According to specific embodiments, the contacting is effected under conditions which allow the formation of a complex comprising polypeptide of Amphiregulin, TGF-alpha and/or HB-EGF present in the cell and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Non-limiting examples of methods of detecting formation of the immunocomplex include Enzyme linked immunosorbent assay (ELISA), Western blot analysis, immunoprecipitation (IP), radio-immunoassay (RIA), Fluorescence activated cell sorting (FACS), immunohistochemical analysis, in situ activity assay (using e.g., a chromogenic substrate applied on the cells containing an active enzyme), in vitro activity assays (in which the activity of a particular enzyme is measured in a protein mixture extracted from the cells) and molecular weight-based approach.

Thus, according to one embodiment, there is provided a composition of matter comprising a biological sample of a subject having a cancer selected from the group consisting of ovarian cancer, head and neck cancer and pancreatic cancer exhibiting resistance to chemotherapy, and a monoclonal antibody to amphiregulin and optionally an antibody to TGF-alpha and/or an antibody to HB-EGF. Such a biological sample may be used for diagnostics (e.g., direct ELISA assay).

The expression level of amphiregulin, TGF-alpha and/or HB-EGF is then compared to the expression level in a control sample.

The control sample is typically obtained from a healthy subject (known not to have cancer, values of which may be present also in the literature) or from the same subject prior to the onset of the disease (i.e., healthy). Since biological characteristics depend on, amongst other things, species and age, it is preferable that the control sample is obtained from a subject of the same species, age, gender and from the same sub-population (e.g. smoker/nonsmoker). Alternatively, control data may be taken from databases and literature.

When the expression level of amphiregulin in the test sample is above the control sample (e.g. by about 5%, 10%, 20%, 30%, 40%, 50%, 60%, 70%, 80%, 90%, 100% or more), and there is no apparent expression level of TGF-alpha and/or HB-EGF, or the expression level of TGF-alpha and/or HB-EGF is comparable or below that of the control sample (e.g. by about 5%, 10%, 20%, 30%, 40%, 50%, 60%, 70%, 80%, 90%, 100% or less), the subject is recognized as suitable for treatment.

Once suitability of the subject has been determined, the subject may be treated by an agent which down-regulates amphiregulin expression level and/or activity.

The "activity" of amphiregulin as used herein, refers to binding of same to its appropriate receptor (e.g. binding of amphiregulin to an EGF receptor) and activating same (e.g. activating intracellular signal transduction pathways).

According to one aspect of the invention there is provided a method of treating cancer, the method comprising administering to a subject selected according to the method of some embodiments of the invention (i.e., having cancer and exhibiting resistance to chemotherapy and elevated levels of AREG and optionally reduced levels of HG-EGF and/or TGFα, as described hereinabove) a therapeutically effective amount of an agent which down-regulates an activity or expression of amphiregulin, thereby treating the cancer.

As used herein, the term "treating" refers to alleviating, attenuating, palliating or eliminating the symptoms of a cancer, slowing, reversing or arresting the progression of the cancer, or curing the cancer.

As used herein the term "therapeutically effective amount" in reference to the treatment of cancer, refers to an amount capable of invoking one or more of the following effects: (1) sensitization of cancer cells of the subject to a chemotherapeutic agent; (2) inhibition, to some extent, of tumor growth, including, slowing down and complete growth arrest; (3) reduction in the number of tumor cells; (4) reduction in tumor size; (5) inhibition (i.e., reduction, slowing down or complete stopping) of tumor cell infiltration into peripheral organs; (6) inhibition (i.e., reduction, slowing down or complete stopping) of metastasis; and/or (7) relief, to some extent, of one or more symptoms associated with the cancer. A "therapeutically effective amount" of an amphiregulin down-regulating agent (e.g. anti-AREG antibody) for purposes of anti-cancer treatment may be determined in a routine manner by any method known to one of skill in the art (e.g. ultrasound, x-ray, CT scan, MRI, etc.).

As used herein, the terms "down-regulate" or "down-regulating" when relating to the expression level and/or activity of amphiregulin refers to preventing, reducing, inhibiting, decreasing and/or eliminating the expression level and/or activity of the amphiregulin. According to one embodiment, the decreasing is effected so that the levels are not substantially elevated compared to the control sample.

According to another embodiment, the levels are decreased maximally so as to completely eliminate the activity of amphiregulin.

A number of agents can be used in accordance with this aspect of the present invention to down-regulate the expression level and/or activity of amphiregulin in the cancer cell.

Thus, for example, down-regulation of amphiregulin can be effected on the genomic and/or the transcript level using a variety of molecules which interfere with transcription and/or translation [e.g., RNA silencing agents (e.g., antisense, siRNA, shRNA, micro-RNA), Ribozyme, DNAzyme and a CRISPR system (e.g. CRISPR/Cas)], or on the protein level using e.g., antagonists, antibodies, enzymes that cleave the polypeptide or inhibit functionality of the peptide and the like.

Following is a list of agents capable of decreasing the expression level and/or activity of amphiregulin.

One example, of an agent capable of down-regulating an amphiregulin is an antibody or antibody fragment capable of specifically binding amphiregulin. Preferably, the antibody specifically binds at least one epitope of an amphiregulin. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof (such as Fab, Fab', F(ab')2, Fv, scFv, dsFv, or single domain molecules such as VH and VL) that are capable of binding to an epitope of an antigen.

According to an embodiment, the antibody is isolated, e.g. at least partially separated from the natural environment e.g., from a cell.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, a Fc fragment, and antibody fragments comprising essentially whole variable regions of both light and heavy chains such as an Fv, a single chain Fv (scFv), a disulfide-stabilized Fv (dsFv), an Fab, an Fab', and an F(ab')2.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al. (1991)

Nature 352:624-628 and Marks et al. (1991) J. Mol. Biol. 222:581-597, and further described hereinbelow.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to an embodiment of the present invention, the CDR amino acid sequences of the anti-AREG antibody are as set forth in SEQ ID NOs: 4, 6, 8, 18, 20 and 22 (e.g. AR30).

According to a specific embodiment the isolated antibody comprises SEQ ID NOs: 4 (CDR1), 6 (CDR2) and 8 (CDR3), sequentially arranged from N to C on a heavy chain of the protein, and 18 (CDR1), 20 (CDR2) and 22 (CDR3) sequentially arranged from N to C on a light chain of the protein (e.g., AR30).

According to another embodiment of the invention, the amino acid sequence of the antibody heavy chain is as set forth in SEQ ID NO: 2 and the amino acid sequence of the antibody light chain is as set forth in SEQ ID NO: 16 (i.e., AR30).

According to an embodiment of the present invention, the CDR amino acid sequences are as set forth in SEQ ID NOs: 32, 34, 36, 48, 50 and 52 (e.g. AR558).

According to a specific embodiment the isolated antibody comprises SEQ ID NOs: 32 (CDR1), 34 (CDR2) and 36 (CDR3), sequentially arranged from N to C on a heavy chain of the protein, and 48 (CDR1), 50 (CDR2) and 52 (CDR3), sequentially arranged from N to C on a light chain of the protein (e.g. AR558).

According to another embodiment of the invention, the amino acid sequence of the antibody heavy chain is as set forth in SEQ ID NO: 30 and the amino acid sequence of the antibody light chain is as set forth in SEQ ID NO: 46 (i.e. AR558).

According to an embodiment of the present invention, the CDR amino acid sequences are as set forth in SEQ ID NOs: 64, 66, 68, 94, 95 and 96 (e.g. AR37).

According to a specific embodiment the isolated antibody comprises SEQ ID NOs: 64 (CDR1), 66 (CDR2) and 68 (CDR3), sequentially arranged from N to C on a heavy chain of the protein, and 94 (CDR1), 95 (CDR2) and 96 (CDR3) sequentially arranged from N to C on a light chain of the protein (e.g. AR37).

According to another embodiment of the invention, the amino acid sequence of the antibody heavy chain is as set forth in SEQ ID NO: 62 and the amino acid sequence of the antibody light chain is as set forth in SEQ ID NO: 93 (i.e. AR37).

It will be appreciated that for human therapy or diagnostics, humanized, chimeric, primatized, or human antibodies are preferably used.

Chimeric antibodies are immunoglobulin molecules in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are well known in the art. See e.g., U.S. Pat. Nos. 5,807,715 and 4,816,567, which are incorporated herein by reference.

Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Primatized antibodies refer to antibodies comprising monkey variable regions and human constant regions. Methods for producing primatized antibodies are known in the art. See e.g., U.S. Pat. Nos. 5,658,570; 5,681,722; and 5,693,780, which are incorporated herein by reference.

It will be appreciated that targeting of particular compartment within the cell can be achieved using intracellular antibodies (also known as "intrabodies"). These are essentially single chain antibodies (SCA) to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Marasco et al., 1998 Human Gene Ther 9: 1627-42; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

A specific method of generating anti-AREG antibodies is described herein. Specifically, an amphiregulin knockout animal (e.g. mouse, rat, rabbit, etc.) is first immunized with a human amphiregulin protein or peptide thereof (e.g. AREG's EGF-like domain SEQ ID NO: 91) so as to produce an antibody response against the amphiregulin protein or peptide thereof. Immunization may be carried out by a single administration or by multiple administrations (e.g. 2, 3, 4, 5, 6, 7, 8 or more administrations) for as long as needed for antibody production (e.g. every 2, 3, 4, 5 weeks or more for a total of e.g. 2-10 administrations).

According to some embodiments, the antibodies generated according to this method (e.g. monoclonal antibodies) are specific to humans and can be cross reactive with the animal (e.g. mouse) ligand and thus can be used for both human treatment and for pre-clinical testing of efficacy and toxicity in animal models.

According to one embodiment, the antibodies produced are polyclonal antibodies.

Monoclonal antibodies may be further generated from the antibody producing cells of the amphiregulin knockout animal. Thus, hybridomas may be generated by fusing spleen cells of the amphiregulin knockout animals generating a high titer of specific anti-amphiregulin antibodies with myeloma cells (e.g. NSO myeloma cells at a 25:1, 20:1, 15:1, 10:1, 5:1 or 2:1 ratio, respectively, in the presence of PEG). Hybridomas are then screened for specific binding to human amphiregulin.

It will be appreciated that once the CDRs of an antibody are identified, using conventional genetic engineering techniques can be used to devise expressible polynucleotides encoding any of the forms or fragments of antibodies described herein.

According to one embodiment, the polynucleotide comprises a nucleic acid sequence as set forth in SEQ ID NOs: 3, 5, 7, 17, 19 and 21 (e.g. AR30).

According to another embodiment of the invention, the nucleic acid sequence of the antibody heavy chain is as set forth in SEQ ID NO: 1 and the nucleic acid sequence of the antibody light chain is as set forth in SEQ ID NO: 15 (i.e., AR30).

According to one embodiment, the polynucleotide comprises a nucleic acid sequence as set forth in SEQ ID NOs: 31, 33, 35, 47, 49 and 51 (e.g. AR558).

According to another embodiment of the invention, the nucleic acid sequence of the antibody heavy chain is as set forth in SEQ ID NO: 29 and the nucleic acid sequence of the antibody light chain is as set forth in SEQ ID NO: 45 (i.e., AR558).

According to one embodiment, the polynucleotide comprises a nucleic acid sequence as set forth in SEQ ID NOs: 63, 65, 67, 101 and 102 (e.g. AR37).

According to another embodiment of the invention, the nucleic acid sequence of the antibody heavy chain is as set forth in SEQ ID NO: 61 (i.e. AR37).

According to one embodiment, the antibody of the invention is conjugated to an effector moiety or component.

An "effector" or "effector moiety" or "effector component" according to the present teachings may be a molecule that is bound (or linked or conjugated), either covalently, through a linker or a chemical bond, or non-covalently, through ionic, van der Waals, electrostatic, or hydrogen bonds, to an antibody. The effector moiety can be a variety of molecules including, but not limited to, detection moieties including radioactive compounds, fluorescent compounds, an enzyme or substrate, tags such as epitope tags, a toxin, activatable moieties, a chemotherapeutic or cytotoxic agent, a chemoattractant, a lipase; an antibiotic; or a radioisotope emitting "hard" e.g., beta radiation.

The term "cytotoxic agent" used herein relates to a substance that inhibits or prevents the function of cells and/or causes destruction of cells. The term is intended to include radioactive isotopes (e.g., I.sup.131, I.sup.125, Y.sup.90 and Re.sup.186), chemotherapeutic agents (as detailed hereinabove), and toxins such as enzymatically active toxins of bacterial, fungal, plant or animal origin, or fragments thereof, including but not limited to the *Pseudomonas* exotoxins PE35, PE38, PE40, *Pseudomonas aeroginosa* exotoxin A (ETA'), and diphtheria toxin (DT390).

According to a specific embodiment, the effector moiety is a platinum based chemotherapy.

The terms "label" or "detectable moiety" relates to a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, colloidal gold, luminescent nanocrystals (e.g. quantum dots), haptens and proteins or other entities which can be made detectable, e.g., by incorporating a radiolabel into the peptide or used to detect antibodies specifically reactive with the peptide. The radioisotope may be, for example, .sup.3H, .sup.14C, .sup.32P, .sup.35S, or .sup.125I. In some embodiments, the radioisotopes are used as toxic moieties. The labels may be incorporated into the antibodies at any position. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982). The lifetime of radiolabeled antibody compositions may extended by the addition of substances that stabilize the radiolabeled antibody and protect it from degradation. Any substance or combination of substances that stabilize the radiolabeled antibody may be used including those substances disclosed in U.S. Pat. No. 5,961,955.

The present invention also contemplates multispecific antibodies, e.g. bi-epitopic antibodies, wherein a single antibody is capable of recognizing two different epitopes either on the same ligand (e.g. on amphiregulin) or on different ligands (e.g. on amphiregulin and on another EGFR ligand, or on amphiregulin and on EGFR).

Antibodies (e.g., monoclonal antibodies) of the present invention are characterized by one of the following features:

According to one embodiment, there is provided an antibody capable of sensitizing ovarian cancer cells to a chemotherapeutic agent.

According to one embodiment, there is provided an antibody capable of reducing ovarian tumor size of any ovarian tumor secreting amphiregulin.

The present invention further contemplates the use of combination of antibodies, e.g. any combination of the antibodies designated AR30, AR37 and AR558.

The present invention contemplated antibodies capable of recognizing only human amphiregulin (e.g. antibodies which do not bind to murine forms amphiregulin) as well as pan-antibodies capable of recognizing both human and murine (e.g. mouse) amphiregulin.

According to a specific embodiment, the antibodies designated AR30 and AR37 are pan-antibodies recognizing both human and murine amphiregulin.

According to a specific embodiment, the antibody designated AR558 recognizes only human amphiregulin.

According to another embodiment of this aspect of the present invention, the antibodies bind amphiregulin with a $K_D$ below 10 nM. According to one embodiment, the antibodies bind amphiregulin with a $K_D$ of 0.5-2 nM, 0.5-5 nM, 0.5-10 nM, 1-2 nM, 1-5 nM, 1-10 nM or 5-10 nM.

Downregulation of amphiregulin can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., amphiregulin) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

According to one embodiment, RNA silencing is carried out by short interfering RNAs (siRNAs) such as, for example, the amphiregulin siRNA (e.g. sc-39412, Santa Cruz Biotechnology, Inc.).

According to one embodiment, RNA silencing is carried out by microRNA (miRNA or miR) such as, for example, the amphiregulin miRNA (e.g. Product ID: HmiT009941, GeneCopoeia).

According to one embodiment, downregulation of an amphiregulin is effected using an antisense polynucleotide capable of specifically hybridizing with an mRNA transcript encoding the amphiregulin. For example, a suitable amphiregulin antisense oligonucleotide can be that available from Sigma (e.g. Product ID: A7080, Sigma).

Downregulation of an amphiregulin may further be effected, for example, using ribozyme molecules capable of specifically cleaving mRNA transcripts encoding an amphiregulin or utilizing a RNA-guided endonuclease technology e.g. CRISPR system.

Another agent capable of downregulating amphiregulin would be any molecule which binds to and/or cleaves amphiregulin. Such molecules can be amphiregulin antagonists, or amphiregulin inhibitory peptide and include, for example, heparin, which binds and inhibits AREG activity, glucosamine which induces the synthesis of heparan sulfates, a physiological AREG antagonist, or a soluble EGFR (sEGFR).

The present inventors have shown that in vivo treatment of mice with anti-AREG antibodies reduces tumor volume (see Examples 7 and 10) and sensitizes cancer cells to a chemotherapeutic agent (see Example 7).

According to another aspect of the invention there is provided a method of treating cancer via administration of an antibody or an antibody combination of some embodiments of the invention.

According to the present teachings, a subject is tested for expression levels or activity of amphiregulin and optionally HB-EGF and TGF-alpha prior to administration of the antibody or antibody combination of some embodiments of the invention.

The subject treated is preferably characterized by an expression level of amphiregulin above a predetermined threshold. Optionally, the subject is characterized by no expression of TGF-alpha and/or HB-EGF or an expression below a predetermined level of the TGF-alpha and/or HB-EGF as compared to a healthy subject.

An "antibody combination" as used herein related to at least two antibodies. According to one embodiment, a first antibody of the antibody combination being the antibody described herein (e.g. AR30, AR558, AR37).

According to another specific embodiment, the antibody combination comprises any combination of the antibodies designated AR30, AR37 and AR558, e.g. AR30 and AR558, AR30 and AR37, AR558 and AR37, or AR30 and AR558 and AR37.

According to another specific embodiment, the second antibody of the antibody combination binds an Epidermal Growth Factor Receptor (EGFR) ligand distinctive from the first antibody (e.g. binds betacellulin (BTC), epiregulin (EPR), epigen (EPG) and/or neuregulin).

According to another specific embodiment, the second antibody of the antibody combination binds an Epidermal Growth Factor Receptor (EGFR), such as HER2 (present on some forms of ovarian cancer cells). Exemplary anti-EGFR antibodies which can be used in accordance with the present teachings include Cetuximab (e.g. Erbitux®), Trastuzumab (e.g. Herceptin®) and Pertuzumab (e.g. Perjeta®).

According to another specific embodiment, the second antibody of the antibody combination comprises an antibody which targets a factor expressed (e.g. overexpressed) on cancer cells, e.g. a protein expressed on the cancer cell such the folic acid receptor (present on the surface of some ovarian cancer cells) or a marker present on the cancer cell (e.g., cancer antigen 125 (CA-125) or MUC1 present on some forms of ovarian cancer cells). Accordingly, exemplary antibodies which can be used in accordance with the present teachings include Oregovomab (an anti-CA-125 antibody) and HMFG 1 (an anti-MUC1 antibody).

According to another specific embodiment, the second antibody of the antibody combination comprises an antibody which targets a factor associated with cancer development or angiogenesis, e.g. VEGF. An exemplary anti-VEGF antibody which can be used in accordance with the present teachings includes Bevacizuma (e.g., Avastin®).

According to another specific embodiment, the second antibody of the antibody combination comprises an antibody which targets TNF (i.e. anti-TNF antibody). An exemplary anti-TNF antibody which can be used in accordance with the present teachings includes infliximab (e.g., Remicade®), adalimumab (e.g., Humira®), certolizumab pegol (e.g., Cimzia®), and golimumab (e.g., Simponi®).

Targeting more than one target (i.e., AREG) according to the present teachings may be effected using two distinct antibodies or using a bispecific antibody configuration as is well known in the art.

According to another embodiment of the present invention, a cancer may be treated via the administration of one or more antibodies and a chemotherapeutic agent.

According to a specific embodiment, the chemotherapeutic agent is platinum based. According to another specific embodiment, the chemotherapeutic agent is cisplatin or doxorubicin.

In addition, the present invention may be used along with agents which down-regulate an EGFR, such as small kinase inhibitors and soluble ligand receptor traps/decoys [described in detail in Cardo-Vila et al. (2010) PNAS 107(11) 5118-5123, fully incorporated herein by reference].

In addition, the present invention may be used along with agents which down-regulate metalloproteinase, e.g. metallopeptidase domain 17 (ADAM17)/TACE (tumor necrosis factor-α-converting enzyme). Examples of TACE/ADAM17 inhibitors, include but are not limited to, sulfonic acid or phosphinic acid derivatives, e.g. sulfonamides, sulfonamide hydroxamic acids, phosphinic acid amide hydroxamic acids, e.g. as described in WO 98/16503, WO 98/16506, WO 98/16514, WO 98/16520.

Administration of the different agents (e.g. antibodies, chemotherapeutic agents, etc.) may be carried out concomitantly or subsequent to each other.

It will be appreciated that the agents of the present invention (e.g., antibody) can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. antibodies) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Exemplary models for cancer include, but are not limited to, murine animal models including NCr-nude mice inoculated with MiaPaCa human pancreatic cancer cells (i.e. pancreatic cancer animal model), with the human lung tumor cell line H1437 (i.e. lung cancer animal model), with the Cal-27 human head and neck cancer cells (i.e. head and neck cancer animal model) or with human ovarian MLS carcinoma cells (i.e. ovarian cancer animal model).

Regardless of the above the agents of the present invention are administered at an amount selected to avoid unwanted side-effects.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and administration intervals may be adjusted individually to provide sufficient plasma or tissue levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the article of manufacture may further comprise another therapeutic composition for cancer, e.g. chemotherapeutic agent. Thus, for example, the antibodies or fragments thereof can be packaged in one container while the chemotherapeutic agent may be packaged in a second container both for therapeutic treatment.

In order to enhance treatment of the cancer, the present invention further envisions administering to the subject an additional therapy such as radiotherapy, chemotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. Analgesic agents and other treatment regimens are also contemplated. Examples of chemotherapeutic agents are described in detail hereinabove. According to a specific embodiment, the chemotherapeutic agent is a platinum derivative.

As mentioned, the chemotherapeutic agent (e.g., platinum derivative) can also be conjugated to the antibody of the present invention.

As mentioned, to increase the specific biological activity exerted by the antibody of the present invention such an antibody can further include a cytotoxic agent (i.e., a drug)

such as *Pseudomonas* exotoxins PE35, PE38, PE40, *Pseudomonas aeroginosa* exotoxin A (ETA'), and diphtheria toxin (DT390), to thereby form a specific immunotoxin. Such a cytotoxic agent can be attached to the antibody.

In addition, the antibodies taught by the present invention may be further used for detection of amphiregulin in a cancer cell or tissue, or for assessment of down-regulation of same. For diagnostic applications, antibodies typically will be labeled with a detectable moiety. The detectable moiety can be any one which is capable of producing, either directly or indirectly, a detectable signal. For example, the detectable moiety may be a radioisotope, a fluorescent or chemiluminescent compound, or a tag (such as described hereinabove and to which a labeled antibody can bind). The antibodies of the present invention may be employed in any known assay method, such as competitive binding assays, direct and indirect sandwich assays, and immunoprecipitation assays. [Zola, Monoclonal Antibodies: A Manual of Techniques, pp. 147-158 (CRC Press, Inc., 1987)].

The antibodies of this aspect of the present invention can be included in a diagnostic kit, in which the antibodies and optionally solid support and imaging reagents (e.g., antibodies, chromogenic substrate etc.) can be packaged in suitable containers with appropriate buffers and preservatives and used for diagnosis.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Materials and Cell Lines

The following antibodies were used: anti-EGFR (clone 13G8) from Enzo Life Science, anti-phospho EGFR (pTyr1068, clone D7A5) from Cell Signaling Technologies, anti-phospho ERK1/2 (pThr185/pTyr187, clone MAPK-YT) from Sigma-Aldrich, anti-ERK2 (clone C14) and anti-ubiquitin (clone P4D1) from Santa Cruz Biotechnology. All growth factors were from Peprotech.

Ovarian cancer cell lines were from the Cell Line Core Facility of the Weizmann Institute of Science. The MCF10A cells were purchased from the American Type Culture Collection (ATCC CRL-10317™). Both ovarian and lung cell lines were grown in RPMI-1640 supplemented with 10% fetal calf serum (FCS) and 1% PenStrep (100 U/mL Penicilium and 100 µg/mL Streptomycin) with the exception of OVCAR3 cells, which were grown in 20% FCS. MCF10A cells were grown as previously described [Tarcic et al. (2012) FASEB journal: official publication of the Federation of American Societies for Experimental Biology 26, 1582-1592].

Patient Specimens

Ascites fluids from ovarian cancer patients and pleural effusions from lung cancer patients were collected at the Sheba Medical Center in Tel Hashomer (Israel). The study was approved by the Ethics Committee of the Medical Center.

ELISA Assays

Human cancer cell lines were seeded in 10 cm plates, covered with medium (6 mL) and incubated for 4 days. The supernatants were collected and centrifuged at 1200 rpm for 5 minutes. The levels of the EGF-family ligands AREG, BTC, EGF, HB-EGF, NRG1 and TGF-alpha were analyzed using an ELISA kit (DuoSet ELISA kit—R&D Systems).

Ligand Displacement and Receptor Downregulation Assays

For ligand displacement assays, cells were grown in 12-well plates and serum-starved for 12-15 hours. Thereafter, cells were washed with binding medium (RPMI medium containing 20 mM of HEPES, pH 7.5, and 1% albumin) and incubated for 3 hours on ice with a radiolabeled EGF (50 ng/mL; from Perkin-Elmer) in the absence or presence of increasing concentrations of a competing unlabeled ligand. The cells were later washed, lysed and their radioactivity counted.

For receptor downregulation assays, cells were serum-starved as described and were subsequently stimulated with EGF (10 ng/mL), TGF-alpha (10 ng/mL) or AREG (50 ng/mL) for 30, 60, 90 or 120 minutes. At the end of the incubation period, the cells were placed on ice, washed with ice cold medium and subjected to mild acid wash (0.2 M Na-acetate buffer, pH 4.5, and 0.5 M NaCl) for 2 minutes, followed by 2 washes in ice cold medium. Thereafter, cells were incubated for 60 minutes at 4° C. with a radiolabeled EGF. Control wells were incubated with a radiolabeled EGF and an excess (50×) of unlabeled EGF. Finally, cells were lysed in 1 N NaOH, and their radioactivity was determined.

Ligand-Induced Receptor Ubiquitination Assays

Cells were serum-starved overnight, and then stimulated with EGF, TGF-alpha or AREG for 10 minutes. For determination of ligand-induced receptor ubiquitination, cells were extracted in lysis buffer (50 mM HEPES pH 7.5, 150 mM NaCl, 10% glycerol, 1% Triton X-100, 1 mM EDTA, 1 mM EGTA, 10 mM NaF and 30 mM 3-glycerol phosphate) with freshly added 0.2 mM Na3VO4, a protease inhibitor cocktail and 2 mM N-ethylmaleimide (NEM). Twenty µL of protein G agarose beads and 1 µg of antibody were added to 500 µg of protein lysate. After a 2 hour incubation at 4° C., the immunoprecipitates were collected by centrifugation at 14,000 rpm at 4° C. for 1 minute. The supernatant was discarded and the pellet was washed thrice, prior to electrophoresis.

RNA Isolation and qPCR

Total RNA was extracted using the PerfectPure RNA Cultured Cell Kit (5-prime) according to the manufacturer's instructions. Total RNA quantity and quality were determined using the NanoDrop® ND-1000 Spectrophotometer. Complementary DNA was synthesized using the High Capacity Reverse Transcription kit (Applied Biosystems, Life Technologies). Primers for the positive (EREG, TGF-alpha and HB-EGF), negative regulators (MIG6/RALT, DUSP1 and DUSP6) and beta2-microglobulin (B2M) were as previously described (Lauriola M et al., (2014) Nat Commun. 5: 5073). The KiCqStart primers from Sigma-Aldrich were used to detect the levels of human AREG (H_AREG_3). Real-time qPCR analysis was performed with SYBR Green (Applied Biosystems) and specific primers on the StepOne Plus Real-Time PCR system (Applied Biosystems). qPCR signals (cT) were normalized to B2M.

TABLE 4

List of primers used for qPCR amplification of transcripts encoding for negative and positive regulators of EGFR signaling

| Gene | Primer Sequence (5'→3') | SEQ ID NO |
|---|---|---|
| DUSP1_Fw | ACTTCATAGACTCCATCAAGAA | 77 |
| DUSP1_Rev | CTCGTCCAGCTTGACTCGAT | 78 |
| EREG_Fw | TCCATCTTCTACAGGCAGTCCT | 79 |
| EREG_Rev | AGCCACACGTGGATTGTCTT | 80 |
| DUSP6_Fw | CACTGGAGCCAAAACCTGTC | 81 |
| DUSP6_Rev | AGTGACTGAGCGGCTAATGC | 82 |
| HBEGF_Fw | GCTGTGGTGCTGTCATCTGT | 83 |
| HBEGF_Rev | TCATGCCCAACTTCACTTTCT | 84 |
| TGFA_Fw | GTTTTTGGTGCAGGAGGACA | 85 |
| TGFA_Rev | CACCAACGTACCCAGAATGG | 86 |
| MIG6_Fw | GCCACTGCTTTGCAGAAAAT | 87 |
| MIG6_Rev | CCTCTTCATGTGGTCCCAAG | 88 |
| B2M_Fw | TGCCTGCCGTGTGAACCATGT | 89 |
| B2M_Rev | TGCGGCATCTTCAAACCTCCATGA | 90 |

Lentiviral Constructs shRNAs targeting AREG were obtained from Sigma-Aldrich (TRCN0000414423, TRCN0000419935, TRCN0000420315, TRCN0000423298, TRCN0000426883). The vector for the scrambled shRNA was obtained from Addgene (plasmid 1864). Lentiviruses were packaged by co-transfection of constructs with the Sigma-Aldrich MISSION Lentiviral Packaging Mix. In brief, lentiviruses were produced by transfection of HEK293FT cells with Lipofectamine 2000 (Invitrogen) according to the manufacturer's protocol. OVCAR5 cells were subsequently infected and selected with 2 µg/mL of puromycin to create the stable shControl and shAREG cell lines. The efficacy of AREG knockdown was assessed at the RNA level using qPCR, and at the protein level by means of ELISA.

Luciferase Reporter Assays

For promoter reporter assays, MLS and A549 cells were co-transfected with a *Renilla* luciferase plasmid containing the promoter region of AREG, TGF-alpha, a positive control of promoter activity, namely GAPDH, or a random control vector R01 used as a negative control (SwitchGear Genomics). Additionally, the pGL3-Control vector containing Firefly luciferase (Promega) was transfected as a control for transfection efficiency. Promoter activity was determined using the dual-luciferase reporter assay system according to the manufacturer's instructions (Promega). *Renilla* luciferase luminescence values were normalized to Firefly luminescence and quantified relative to control.

Surface Plasmon Resonance (SPR) Measurements

SPR was performed on a BIAcore 3000 instrument (BIAcore, Uppsala, Sweden). Proteins were diluted in 100 mM Na-acetate (pH 4.6) to 20 µg/ml and immobilized on a CM5 sensor chip using a standard protocol of amine coupling. The protein solution was flown over the chip for 5 minutes at a rate of 20 µl/min. The binding assay was performed by injecting the analyte solutions at 25° C. at 8 different concentrations (depending on the ligand: hAREG 1-30 nM, mAREG 500-5000 nM, hHB-EGF 1-100 nM and mHB-EGF 1-20 uM). These conditions resulted in a linear relation between protein concentration and maximal (steady-state) response, indicating a pseudo first order regime in relation to the immobilized ligand. The net signal was obtained by subtracting the blank signal (plain dextran matrix) from the signal recorded from the immobilized surface. The association phase for analyte binding to all ligands was followed for 4 minutes, and dissociation phases were monitored for 3 minutes. Surface regeneration between consecutive binding cycles included a 1 min injection of 2 mM NaOH. The response was monitored as a function of time (sensorgram). Multi-concentration data underwent fitting using the software BIAevaluation 3.2.

Generation of Monoclonal Antibodies

A monoclonal antibody which targets human AREG, termed AR30, was generated as previously described [Lindzen M. et al. (2010) Proceedings of the National Academy of Sciences of the United States of America 107, 12559-12563]. Specifically, as it is known that highly conserved three disulfide bonds are responsible for the correct folding and activity of the EGF-like domain of all ErbB ligands, the EGF-like domain of AREG was expressed in bacteria as a fusion protein, linked to the thioredoxin protein (TRX). The fused protein also contained a histidine repeat. Following expression in bacteria, AREG was purified using a metal column, and its biological activity was verified by confirming its ability to induce EGFR phosphorylation. The results obtained ensured that the recombinant ligand represented the respective functionally active conformation. Hence, mice were subsequently immunized with the active TRX-fused AREG.

Following four injections of TRX-AREG, sera were obtained from mice and examined for anti-ligand responses. Antisera of immunized mice were tested for their ability to inhibit ligand-induced EGFR phosphorylation. Subsequently, the spleens of two mice were used to establish hybridomas, which were screened for their ability to recognize AREG by ELISA.

To functionally characterize a selected anti-AREG mAb, its specificity was tested using an Enzyme-Linked Immunosorbent Assay (ELISA) assay covered with different ligands. Further, the anti-AREG mAb could immunoprecipitate a commercial preparation of AREG, and specifically inhibit AREG-induced EGFR phosphorylation. The AR30 affinity to the different ligand was assessed by Surface plasmon resonance (SPR).

Xenograft Mouse Models

All animal procedures were approved by the Weizmann Institute of Science's review board. Female athymic NCr-nude mice (6 weeks old) were inoculated subcutaneously with $2\times10^6$ human ovarian MLS cancer cells. Once tumors became palpable (5-7 days), the mice were randomized into groups and injected intraperitoneally at the indicated time points with the indicated monoclonal antibodies, chemotherapy or the combination. Tumor volumes were monitored twice a week, and body weights were measured once a week.

Cloning and Expression of the EGF-Like Domain of Amphiregulin (AREG) in Bacteria AREG's EGF-like domain (SEQ ID NO: 91) was cloned into the pET32b vector, and expressed as C-terminal thioredoxin (TRX) fusion proteins with a Factor Xa cleavage site flanking the N-terminal residue of the EGF-like domain [as previously described in Lindzen M. et al. (2010), supra]. The fusion proteins were expressed in *Escherichia coli* (BL21) using standard procedures. Following sonication, cleared extracts were transferred to pre-equilibrated NiNTA beads. The beads were washed, and bound proteins were eluted with 300 mM immidazole. Construction of fusion proteins comprising a GPI motif was performed in two steps. The first PCR reaction was performed on the GPI signal of the rat contactin-1. The 5' primer introduced a NsiI cleavage site, which was followed by an HA tag, and the 3' primer introduced a NotI site. The product was cloned into the pIRES-Hyg vector using NsiI and NotI restriction enzymes. The second step employed overlapping PCR. The first reaction used the signal peptide of HER2 as a template, and a 3' primer that included the 5' sequence of the respective EGF-like domain. The second PCR reaction used the respective EGF-like domain as a template, and a 5' primer which included the 3' end of the HER2 signal peptide. The products of both reactions served as templates for another PCR reaction. The final PCR product was cloned into pIRES-Hyg-GPI, by using BamHI and NsiI cleavage sites. To establish clones of CHO cells, the corresponding pIRES-Hyg were transfected using Lipofectamine (Invitrogen, Carlsbad, Calif.), and selected clones using hygromycin (2 µg/ml).

Generation of Antibodies in Knockout Mice and Specificity Tests of Monoclonal Anti-AREG Antibodies Five $AREG^{-/-}$ mice (3 month old) were injected subcutaneously, and into the foot pad, with 30 ag AREG protein in complete Freund's adjuvant (Tifco, Detroit, Mich.). Three weeks later, a second injection was performed in incomplete Freund's adjuvant. This injection was followed by 3-5 injections at intervals of 3 weeks. A month after the last boost, the two mice with the highest titer received two more injections on two consecutive days. Four days after the last boost, cells from each spleen were fused with $20\times10^6$ NS0/1 myeloma line as previously described [Eshhar Z. et al. (1980) J Immunol 124, 775-780]. Following fusion, cells were distributed into 96-well plates, at concentration of $2\times10^4$ viable myeloma cells/well. Hybrid cells were selected for growth in the presence of HAT. Positive hybrid cultures were weaned out of HAT, cloned and re-cloned in limiting dilution.

Example 1

Amphiregulin and Other EGF-Family Ligands are Detectable in Fluids from Cancer Patients, as Well as in Media Conditioned by Cancer Cells

Due to the established roles for a variety of growth factors in cancer progression, an ELISA was used to determine the repertoire of EGF-like ligands present in fluids collected from advanced stage ovarian and lung cancer patients. Ascites fluids that were collected from 43 ovarian cancer patients, who were previously treated with chemotherapy, identified AREG as one of the two most frequently secreted factors (FIG. 1A and Table 1): 37 out of the 43 patients (86%) expressed AREG, and the levels displayed wide variation (10-1,800 pg/ml). The ELISA analysis similarly identified TGF-alpha in the analyzed fluid samples, but HB-EGF (60%), EGF (44%), NRG1 (21%) and BTC (6.9%) were not only detected in fewer patients, but their levels rarely exceeded 200 pg/ml. A somewhat similar pattern was observed in media conditioned by 13 ovarian cancer cell lines (FIG. 1C): AREG (92% of the analyzed cell lines), TGF-alpha, HB-EGF (54%), and NRG1 were detectable, though the latter was observed in only one of the cell lines. Notably, EGF was undetectable in the conditioned media, but it was detected in 44% of patients' fluids, raising the possibility of a non-tumor origin. Similarly, BTC was undetected in any ovarian cancer cell line, but a minority of patients' ascites fluids contained this growth factor.

TABLE 1

Determination of EGF-like ligands in ascites fluid from 43 ovarian cancer patients. Ligands were quantified by using the DuoSet ELISA kit (R&D Systems). Ligand concentrations are indicated in pg/mL ± S.D.

| Patient | AREG | BTC | EGF | HB-EGF | NRG-beta1 | TGF-α |
|---|---|---|---|---|---|---|
| 1 | 1858.4 ± 0.0 | — | 13.6 ± 0.0 | 34.1 ± 2.4 | — | 12.3 ± 1.4 |
| 2 | 1433.9 ± 24.8 | — | — | 80.2 ± 2.8 | — | 11.4 ± 2.5 |
| 3 | 1373.6 ± 0.1 | — | 66.7 ± 0.0 | 330.8 ± 22.8 | 192.5 ± 63.6 | 64.0 ± 3.1 |
| 4 | 760.5 ± 0.0 | — | — | 3.6 ± 0.0 | — | 5.9 ± 0.0 |
| 5 | 634.8 ± 0.0 | — | — | — | — | 2.8 ± 0.0 |
| 6 | 529.8 ± 0.0 | 133.4 ± 6.4 | 190.9 ± 0.0 | 1116.3 ± 2.3 | 232.5 ± 35.4 | 174.8 ± 1.9 |
| 7 | 379.9 ± 106.4 | — | 8.0 ± 0.0 | 104.1 ± 0.8 | — | 46.6 ± 4.2 |
| 8 | 307.4 ± 106.5 | 177.5 ± 30.1 | 60.4 ± 0.0 | 320.4 ± 114.2 | — | 95.3 ± 17.6 |
| 9 | 298.4 ± 0.0 | — | — | — | — | 9.6 ± 0.0 |
| 10 | 251.2 ± 0.0 | — | — | — | — | — |
| 11 | 208.0 ± 26.0 | — | — | — | — | — |
| 12 | 185.9 ± 3.3 | — | — | — | — | 4.3 ± 0.0 |
| 13 | 182.7 ± 46.0 | — | 198.8 ± 0.0 | 329.8 ± 1.8 | — | 49.2 ± 12.4 |
| 14 | 105.5 ± 3.5 | — | — | 264.3 ± 25.1 | — | 62.9 ± 9.6 |
| 15 | 102.9 ± 27.3 | — | — | 105.5 ± 1.6 | — | 27.5 ± 2.0 |
| 16 | 83.9 ± 9.7 | — | — | 15.2 ± 6.7 | — | 3.1 ± 0.0 |
| 17 | 79.8 ± 0.0 | 73.4 ± 5.7 | 20.1 ± 0.0 | 306.9 ± 3.1 | 222.5 ± 21.2 | 78.9 ± 7.6 |
| 18 | 53.2 ± 0.5 | — | — | 84.9 ± 3.9 | — | 32.7 ± 0.8 |
| 19 | 52.6 ± 0.0 | — | 15.7 ± 0.0 | 5.2 ± 0.0 | 242.5 ± 63.6 | 9.0 ± 1.9 |
| 20 | 52.5 ± 1.4 | — | — | — | — | 8.6 ± 0.0 |
| 21 | 45.5 ± 0.0 | — | — | — | 182.5 ± 21.2 | — |
| 22 | 44.6 ± 0.0 | — | — | 12.4 ± 5.5 | — | 6.2 ± 0.0 |
| 23 | 39.7 ± 0.0 | — | 9.3 ± 0.0 | 5.8 ± 0.0 | — | 4.7 ± 0.0 |
| 24 | 38.9 ± 0.0 | — | 10.4 ± 0.0 | — | — | 3.4 ± 0.0 |
| 25 | 35.8 ± 0.0 | — | — | — | — | 4.5 ± 0.0 |
| 26 | 30.8 ± 0.0 | — | — | — | — | — |
| 27 | 29.9 ± 0.0 | — | 12.2 ± 0.0 | — | 232.5 ± 91.9 | 2.3 ± 0.0 |
| 28 | 28.2 ± 0.1 | — | — | 93.0 ± 8.6 | 247.5 ± 0.0 | 27.9 ± 2.7 |
| 29 | 26.4 ± 0.0 | — | 10.7 ± 0.0 | 94.1 ± 3.9 | — | 18.0 ± 0.4 |
| 30 | 22.0 ± 0.0 | — | 8.0 ± 0.0 | 191.3 ± 0.0 | — | 42.5 ± 6.8 |
| 31 | 21.4 ± 0.1 | — | 9.6 ± 0.0 | — | — | 3.6 ± 0.0 |
| 32 | 20.8 ± 0.0 | — | 8.8 ± 0.0 | 14.7 ± 0.0 | — | 9.0 ± 0.0 |
| 33 | 20.2 ± 0.0 | — | 19.3 ± 0.0 | 25.2 ± 0.0 | — | 9.2 ± 0.0 |
| 34 | 16.2 ± 0.0 | — | 11.2 ± 0.0 | 66.3 ± 2.4 | 157.5 ± 42.4 | 16.6 ± 0.2 |
| 35 | 15.6 ± 0.0 | — | — | — | — | 5.7 ± 0.0 |
| 36 | 11.9 ± 0.0 | — | — | 11.3 ± 0.0 | — | 7.4 ± 0.0 |
| 37 | 9.7 ± 0.0 | — | 13.8 ± 0.0 | — | — | 6.1 ± 0.0 |
| 38 | — | — | — | — | — | — |
| 39 | — | — | — | — | — | 2.3 ± 0.0 |
| 40 | — | — | — | — | — | 3.7 ± 0.0 |
| 41 | — | — | 7.5 ± 0.0 | 4.1 ± 0.0 | — | 4.5 ± 0.0 |
| 42 | — | — | — | 235.8 ± 15.7 | 282.5 ± 49.5 | 55.1 ± 0.9 |
| 43 | — | — | — | 116.3 ± 2.4 | — | 28.7 ± 1.9 |

A parallel analysis was performed on pleural effusions from lung cancer patients (FIG. 1B and Table 2). In similarity to the ovarian patients' fluids, the major growth factor detected in pleural effusions from lung cancer patients was AREG; 16 of 18 samples contained relatively high concentrations of this growth factor. In addition, like in the collection of ascites fluids from ovarian cancer patients, approximately 50% of the lung cancer fluids contained TGF-alpha and HB-EGF. Analysis of the conditioned media of 7 lung cancer cell lines identified AREG as a common and almost exclusive trait (FIG. 1D); no other ligand, with the exception of HB-EGF (in H522 cells), was detectable. Taken together, these results propose that self-produced AREG is a most prevalent EGF-like growth factor of both ovarian and lung cancer.

30% receptor downregulation. Similarly, using MCF10A cells and either equimolar concentrations of EGF, TGF-alpha and AREG, or a 100-fold higher concentration of the latter ligand (FIG. 2H), an effective downregulation of EGFR was observed only when testing very high concentrations of AREG. These observations are in line with the

TABLE 2

Determination of EGF-like ligands in pleural effusion fluid samples from 18 lung cancer patients. Ligands were quantified by using the DuoSet ELISA kit (R&D Systems). Ligand concentrations are indicated in pg/mL ± S.D.

| | Ligands (pg/mL) | | | | | |
|---|---|---|---|---|---|---|
| Patient | AREG | BTC | EGF | HB-EGF | NRG-beta1 | TGF-α |
| 1 | 631.0 ± 73.0 | — | — | — | — | — |
| 2 | 413.0 ± 42.0 | — | 13.8 ± 2.4 | — | — | — |
| 3 | 349.0 ± 19.0 | — | — | 78.3 ± 9.4 | — | 39.0 ± 1.7 |
| 4 | 291.0 ± 36.0 | — | 15.0 ± 0.6 | 98.0 ± 14.1 | — | 72.0 ± 8.3 |
| 5 | 287.4 ± 17.5 | — | — | — | — | 1.7 ± 0.0 |
| 6 | 285.0 ± 76.0 | — | — | 80.0 ± 7.1 | — | 67.0 ± 6.2 |
| 7 | 259.0 ± 52 | — | — | — | — | — |
| 8 | 236.0 ± 73 | — | — | — | — | — |
| 9 | 210.5 ± 6.4 | — | — | — | — | 20.9 ± 0.8 |
| 10 | 209.0 ± 2.8 | — | — | 167.0 ± 21.2 | — | 64.4 ± 3.3 |
| 11 | 190.0 ± 43.8 | — | — | — | — | — |
| 12 | 138.0 ± 12.0 | — | — | — | — | — |
| 13 | 109.0 ± 21.1 | — | — | 167.0 ± 11.8 | — | 191.0 ± 8.7 |
| 14 | 52.5 ± 25.5 | — | — | — | — | — |
| 15 | 46.5 ± 14 | — | — | — | — | — |
| 16 | 28.6 ± 7.1 | — | — | 50.0 ± 1.9 | — | 11.8 ± 6.3 |
| 17 | 12.9 ± 0.0 | — | — | 115.8 ± 3.1 | — | 25.5 ± 0.0 |
| 18 | — | — | 12.8 ± 0.0 | 49.7 ± 5.5 | — | 35.3 ± 2.1 |

Example 2

AREG is Inefficiently Depleted and Causes Weaker Receptor Downregulation than EGF or TGF-Alpha The observed wide distribution and high concentrations of AREG in patients' fluids raised the possibility that this factor confers a selective advantage, which may not be shared by the other seven EGF-like ligands. Hence, the biological activity of AREG was compared to those of the better-understood family members. It is notable that George Todaro and colleagues, who discovered AREG in 1989, reported that it binds to EGFR but not as avidly as EGF does, but it nevertheless fully supplants the requirement for EGF or TGF-alpha in keratinocyte growth [Shoyab M. et al. (1989) Science 243, 1074-1076]. These early observations might relate to the duration of inducible EGFR signaling, which is directly correlated to binding affinity and the intracellular fate of the membrane bound EGFR: depending on ligand identity, occupied EGFRs will either undergo degradation or recycle back to the plasma membrane, ready for re-activation. To specifically address relations between binding affinity and receptor endocytosis, the MCAS ovarian cancer cell line was used. As expected, displacement of a radiolabeled EGF by AREG indicated an approximately 100-fold lower binding affinity, compared to EGF (FIG. 2A). This difference was observed also in MCF10A immortalized mammary cells (FIG. 2G), suggesting independence from cellular context. In line with relatively low affinity, only limited effect of AREG on endocytosis-mediated downregulation of EGFR was observed, in comparison with similar or lower concentrations of EGF and TGF-alpha (FIG. 2B): while EGF (10 ng/ml) induced approximately 80% down-regulation and TGF-alpha (10 ng/ml) achieved 70-75% reduction, AREG (50 ng/ml) induced only approximately lower apparent affinity of AREG, as compared to EGF and TGF-alpha, and they propose that the observed, relatively high concentrations of AREG in patients' fluids are due, in part, to inefficient removal of this ligand by means of receptor-mediated endocytosis.

Example 3

AREG Induces Relatively Weak Ubiquitination of EGFR

Early observations demonstrated that EGFR signals undergo rapid desensitization through endocytosis, followed by degradation in lysosomes [Carpenter, G. and Cohen, S. (1976) The Journal of cell biology 71, 159-171], and later studies associated this process with receptor ubiquitination [Levkowitz, G. et al. (1999) Molecular cell 4, 1029-1040]. Therefore, the capabilities of EGF, TGF-alpha and AREG to induce ubiquitination of EGFR in human ovarian cancer cells (MCAS and MLS), as well as in lung cancer cells (H358 and A549; FIGS. 2C-2F) were compared. To this end, cells were incubated for 10 minutes with the respective growth factor, and subsequently EGFR ubiquitination was assayed using anti-ubiquitin antibodies. Whereas EGF and TGF-alpha were able to induce strong ubiquitination and initiate receptor degradation, similar concentrations of AREG failed to do so, in line with previous reports that examined other cell types [see e.g. Baldys A. et al., (2009) Biochemistry 48, 1462-1473]. Interestingly, a ten-fold higher concentration of AREG was capable of inducing comparable levels of receptor ubiquitination as EGF and TGF-alpha, suggesting that the lower binding affinity of AREG was responsible for this effect. Notably, the same phenomenon was observed in both the ovarian and the lung cancer cell lines, attesting to a general mechanism, which is cell type independent. In conclusion, unlike other ligands of EGFR, AREG might escape receptor ubiquitination and signaling desensitization, potentially explaining why advanced ovarian and lung tumors frequently secrete this factor.

Example 4

Induction of Gene Expression Programs Requires Relatively High Concentrations of AREG EGFR activation and the cytoplasmic events it later evokes translate to the induction of complex gene expression programs, which, among other functions, propel positive and negative feedback regulatory loops. Because previous reports have not addressed relations between AREG's concentrations and the induction of gene expression programs, high and low concentrations (10 and 100 ng/ml) of the growth factor were applied and qPCR was used to analyze several components of both positive (i.e., the early induced ligands of EGFR, namely EREG, TGF-alpha and HB-EGF) and negative feedback regulatory loops. The latter comprised MIG6/RALT, an inducible inhibitor of EGFR, along with two members of the dual specificity phosphatases of the DUSP/MKP group. In line with low affinity and weak activity, the lower concentration of AREG induced hardly detectable signals, but the 10-fold higher concentration resulted in clear, time dependent transcription of the six tested genes (FIGS. 3A-F). Interestingly, the effects of EGF were even higher and with both ligands an oscillatory pattern of several transcripts was observed. In conclusion, in similarity to EGF, AREG is able to instigate gene expression programs that carve biological outcomes. However, this requires relatively high concentrations of the growth factor.

Example 5

AREG Silencing in Human Ovarian Cancer Cells Inhibits their Tumorigenic Growth in Animals In order to examine the prediction that AREG secretion contributes to the tumorigenic virulence of ovarian cancer, a model cell system was established consisting of the OVCAR5 cancer cell line that secretes relatively large quantities of AREG (see FIG. 1C). Cells were transduced with viral vectors encoding either a scrambled short hairpin RNA (shControl) or an AREG-targeting shRNA (shAREG). Analyses of both mRNA levels (using qPCR) and protein secretion (using ELISA) confirmed effective reduction of AREG expression by the specific hairpin (FIG. 4A). When cultured, the corresponding cell lines displayed marked differences in their rate of proliferation (FIG. 4B). Hence, in the next step the two derivative sub-lines were inoculated in the flanks of immunocompromised animals (Balb/c nude; 10 mice per group) and monitored tumor growth over a period of 4 weeks. As shown in FIG. 4C, shAREG-expressing cells formed significantly smaller tumors relative to the control cells ($p<0.005$), in agreement with their in vitro growth rates. In conclusion, and in line with the in vitro data, AREG secretion might play an important role in ovarian tumor growth, at least in a model animal system.

Example 6

AREG Expression is Increased after Treatment of Ovarian Cancer Cells with a Chemotherapeutic Drug Platinum-based anti-tumor agents have been the mainstay of ovarian cancer chemotherapy for the last three decades, but various mechanisms of resistance, including defects in drug transport, limit therapeutic efficacy. In this context, it is interesting noting that a previous study found that resistance of MCF7 mammary cancer cells to cisplatin was accompanied by both inactivation of the p53 pathway and a selective up-regulation of AREG expression [Eckstein N. et al. (2008) The Journal of biological chemistry 283, 739-750]. Because the majority of the body fluids which were analyzed were from patients treated with chemotherapy, the possibility that high level secretion of AREG by ovarian and lung cancer cells could be attributed to patient exposure to chemotherapeutic agents, such as cisplatin, was examined. Hence, a luciferase reporter DNA construct was introduced containing the promoter region of AREG into both MLS ovarian cancer cells and A549 lung cancer cells. Upon treatment of cells with increasing concentrations of cisplatin a 2-fold and 1.5-fold increases was observed in the reporter activity in ovarian and lung cells, respectively (FIGS. 5A and 5B). A similar experiment that used a luciferase reporter corresponding to TGF-alpha (or GAPDH, as control) and MLS cells detected no consistent, cisplatin-induced changes in TGF-alpha induction (FIGS. 5C-5D). Yet another line of evidence supporting specificity of the cisplatin effect to the AREG promoter is presented in FIGS. 5E-5F: Exposure of both ovarian and lung cancer cells to the chemotherapeutic agent was followed by increased secretion of AREG, not EGF, TGF-alpha or HB-EGF to the medium. Collectively these results propose that formation of DNA adducts, in response to treatment with genotoxic agents, might specifically increase expression and secretion of AREG by ovarian and lung cancer cells.

Example 7

A Monoclonal Antibody Specific to AREG Inhibits Ovarian Tumor Xenografts in Animals and Sensitizes them to a Chemotherapeutic Drug Drugs targeting EGFR or the homologous protein ERBB2/HER2 are already used to clinically treat breast, lung, gastric, pancreatic, colorectal and head and neck cancers [Yarden, Y. and Pines, G. (2012) Nature reviews Cancer 12, 553-563]. In ovarian cancer, EGFR has been proposed as a potential drug target, but EGFR antagonists have so far shown only limited clinical benefits [Murphy M. and Stordal, B. (2011) Drug resistance updates: reviews and commentaries in antimicrobial and anticancer chemotherapy 14, 177-190]. Nevertheless, aberrant EGFR expression has been associated with poor outcome of ovarian cancer patients, raising the possibility that targeting other ligands of EGFR might be effective. In an attempt to test this prediction, a previously described approach to generate monoclonal antibodies [Lindzen M. et al., (2010), supra] was employed generating an antibody termed AR30 targeting human AREG. Using plasmon resonance and immunoblotting, high affinity binding of AR30 with human AREG was confirmed (Table 3 and FIG. 6D). Interestingly, AR30 recognized no other EGFR ligand, except for the human form of HB-EGF. Notably, it has been previously reported that an anti-HB-EGF antibody can bind with AREG [Sato S. et al. (2012) PloS one 7, e51964], suggesting that the two growth factors share structural determinants.

TABLE 3

Binding affinities of mAb AR30 toward the indicated EGF family ligands. Solutions containing increasing concentrations (1-20,000 nM) of different ligands, were passed over surfaces coated with AR30, an anti-AREG mAb, to derive the indicated dissociation constants using plasmon resonance measurements.

| LIGAND | Kd (nM) |
|---|---|
| hAREG | 1.7 |
| hHB-EGF | 80 |
| hTGF-alpha | >10,000 |
| hEGF | >10,000 |
| hBTC | >10,000 |
| hNRG1 | >10,000 |
| hEPG | >10,000 |
| mAREG | >10,000 |
| mHB-EGF | 6650 |

Figure 6F:
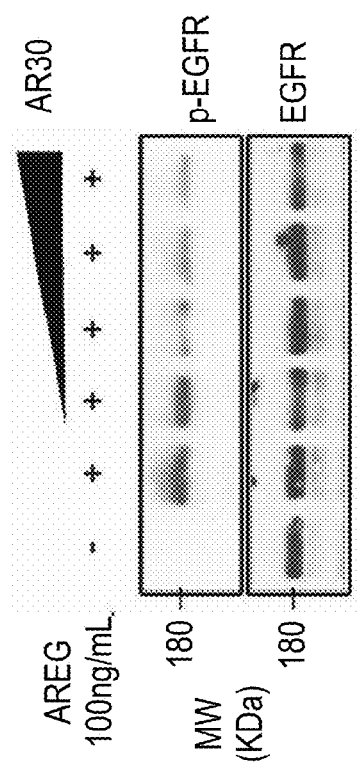

Next, the ability of AR30 to intercept AREG-induced phosphorylation of EGFR and activation of downstream signals was analyzed. To this end, the ability of increasing concentrations of AREG to elevate tyrosine auto-phosphorylation of EGFR was tested, and observed a consistent dose-response pattern that, as expected, did not reach the strong signal elicited by EGF (data not shown). Importantly, AR30 only partially reduced the effect of AREG on receptor phosphorylation, and this was independent of the concentration of either AREG or AR30 (FIGS. 6E-6F). Accordingly, the partial inhibitory effect of AR30 was insufficient for blocking downstream signaling to ERK, as revealed by using an antibody specific to the phosphorylated (active) form of ERK (data not shown).

The observed partial inhibition of EGFR phosphorylation by AR30 prompted an investigation directed to the impact on tumorigenic growth of AREG-secreting ovarian cells. In the first set of experiments the anti-tumor effects of AR30 and cetuximab, a clinically approved anti-EGFR antibody, was compared. MLS cells were inoculated subcutaneously into the flanks of female nude mice and once tumors became palpable, mice were randomized into groups of 9-11 animals. Thereafter, the antibodies were injected into the peritoneum, and tumor growth was monitored over a period of six weeks (data not shown). Both antibodies partly inhibited tumor growth, and AR30 was at least as effective as cetuximab. The next set of animal tests assumed that chemotherapy-induced up-regulation of AREG secretion (see FIGS. 5A-5F) supports tumor growth under platinum-based treatment. Hence, using mice bearing MLS tumors a combination of cisplatin and the anti-AREG antibody, AR30, was examined. Following randomization, mice were treated with or without AR30, along with cisplatin (5 mg/kg bodyweight). The results presented in FIG. 7B show that as single agents, both cisplatin and the AR30 antibody only mildly inhibited MLS tumors under the conditions selected. Nonetheless, the combination of cisplatin and AR30 almost completely inhibited tumor growth (FIGS. 7B and 7C).

In summary, using ascites and pleural fluids relatively high concentrations of AREG were detected in the majority of advanced ovarian and lung cancer patients. The in vitro studies propose that high abundance of AREG in clinical samples might reflect two processes: Firstly, induction of AREG transcription following patient treatment with genotoxic drugs, and, secondly, inefficient AREG clearance by means of receptor endocytosis. Presumably, high abundance of AREG, relative to other EGF family ligands, compensates for the low affinity interactions of this growth factor with EGFR. Accordingly, the present inventors show that high concentrations of AREG are needed for enhancement of tyrosine phosphorylation and induction of gene expression programs. In line with critical roles in progression of ovarian cancer, intercepting AREG by using a newly generated anti-AREG antibody (denoted AR30) greatly sensitized ovarian cancer cells to a chemotherapeutic agent. These observations might open a way for clinical testing of a humanized version of AR30.

Example 8

Monoclonal and Polyclonal Antibodies Specific to AREG were Generated in AREG Knockout Mice Monoclonal and polyclonal anti-AREG antibodies were generated in AREG knockout mice. FIG. 8 presents results obtained when testing the polyclonal as well as monoclonal antibodies on human AREG. mAbs AR37 and AR558 were selected for further analysis. FIG. 9A presents results obtained when murine AREG was used in the ELISA test. As can be seen, mAb AR37 recognized the murine molecule better than the other two mAbs tested.

FIG. 9B presents additional results obtained when testing the polyclonal as well as monoclonal antibodies AR37, AR65, AR324, AR558 on human AREG. FIG. 9C presents results obtained when murine AREG was used in the ELISA test. As can be seen, mAb AR37 recognised the murine molecule.

Example 9

In Vitro Tests of Selected Anti-AREG Monoclonal Antibodies

Following large scale production and purification of antibodies, mAbs AR30, AR37 and AR558 were applied to in vitro assays. The results presented in FIG. 10A illustrate that low concentrations of the antibodies were sufficient for blocking AREG-induced phosphorylation of EGFR of living HeLa cells. In addition, the antigenic determinant targeted by the two mAbs was examined and in comparison to the previously described AR30 antibody. (data not shown) The results obtained indicated that each of the three antibodies engages a different determinant of human AREG. Next, the ability of the antibodies to inhibit proliferation of MCF10A mammary cells was tested in the absence or presence of AREG. The results are presented in FIG. 10B. Moderate inhibition was observed at relatively high concentrations of each of the three mAbs we examined.

Example 10

In Vivo Tests of Selected Anti-AREG Monoclonal Antibodies

To test the ability of anti-AREG antibodies to reduce growth of human tumor cells implanted in immunocompromised mice, Cal 27 tumor cells were used which were inoculated subcutaneously and randomized for treatment after tumors became palpable. The results presented in FIG. 11 demonstrate that the novel mAbs AR30 and AR37 comparably inhibit tumor growth, while AR558 exceeded the activity of either antibody. Furthermore, studies testing pairs of two mAbs illustrate their enhanced anti-tumor activities (data not shown), this can be attributed to the fact that the mAbs bind to distinct antigenic determinants of amphiregulin.

FURTHER ANALYSIS

While normal cells often send signals to neighboring cells, and the latter reciprocate by supplying various growth factors, one hallmark shared by cancer cells of various tissues of origin is their capability to autonomously sustain proliferative signaling in a number of alternative ways: they may overexpress a receptor for a growth factor or present an activating mutation in the receptor or in downstream signaling pathways. Alternatively, they may produce growth factor ligands, to which they can respond via the expression of cognate receptors, resulting in autocrine proliferative stimulation. EGFR well exemplifies this attribute of transformed cells: on the one hand, ductal morphogenesis of the mammary gland is regulated by a paracrine mechanism that involves shedding of AREG by epithelial cells and subsequent stimulation of EGFR of stromal cells. On the other hand, co-expression of EGFR and AREG characterizes a wide variety of carcinomas and skin tumors. This extends to several other ligands, which are co-expressed with EGFR in a variety of tumors.

Since almost a full decade, intercepting EGFR signaling using kinase inhibitors or mAbs has become a mainstay clinical protocol, for example in the treatment of lung and colorectal cancer, respectively. However, rather weak responses that are limited to small groups of patients, along with early onset of resistance to drugs, currently limit clinical applications. Nevertheless, several newer strategies are under development and they include specific aptamers and combinations of 2-3 antibodies, each directed to a distinct receptor's epitope. Directly intercepting EGFR's ligands represents another yet un-approved approach. A decoy recombinant fusion protein containing portions of EGFR and HER4 was able to inhibit all eleven ligands of the EGF family, as well as inhibit several tumor xenografts [Lindzen M. et al. (2012) Oncogene 31, 3505-3515]. To reduce toxicity, it might be critical to intercept fewer ligands, within the context of specific tumors. For example, the present inventors have previously demonstrated that co-inhibition of TGF-alpha and HB-EGF, using a mixture of the respective mAbs, effectively retarded tumorigenic growth of several tumor xenografts [Lindzen M. et al. (2010), supra]. Knowing the repertoire of growth factors produced by a given primary or secondary tumor is a prerequisite, and thus it is offered to sample tumors e.g. by liquid biopsies, even those that may not be easily imaged or localized.

Ascites and pleural fluids of cancer patients are routinely available, often in quite large volumes. The common denominator of the majority of the 56 fluids which were analyzed herein (from ovarian and lung cancer patients) has been high concentrations and almost ubiquitous presence of AREG (FIGS. 1A-1F). High AREG expression already serves as a marker of better response of colorectal cancer patients to EGFR-targeting mAbs. Similarly, in lung cancer patients treated with gefitinib or erlotinib, high AREG was associated with stable, rather than progressive disease. Thus, AREG might serve as a predictor of patient response, and probably also as a target for combination therapy, as elaborated below. The logic behind the common occurrence and high abundance of AREG in liquid biopsies might be attributed to several aspects of the biology of AREG: clearance of AREG from the circulation might be retarded by binding to heparin sulfate proteoglycans, as well as by the relatively low EGFR binding affinity of this ligand and its tendency to increase receptor recycling rather than receptor degradation (see FIGS. 2A-2H). The effect of slow clearance might be augmented by more rapid rates of AREG synthesis, especially in patients undergoing treatment with cytotoxic drugs or patients displaying high estrogen concentrations: both estrogen and a chemotherapeutic agent, cisplatin, enhance AREG expression. In addition, several attributes associated with advanced tumors or with cancer treatment have been linked to AREG induction. The list includes chronic inflammation, high serum levels of the lysophosphatidic acid (LPA), loss of the BRCA1 tumor suppressor, expression of a mutant form of p53 and hypoxic conditions.

The biological and clinical features of AREG, along with frequent expression in ascites fluids obtained from chemotherapy-treated, advanced ovarian cancer patients, prompted the present inventors to generate a new antibody to the human factor, and test it on xenografts of ovarian cancer cells. It is worth mentioning that only 20% of ovarian cancers are diagnosed while they are limited to the ovaries, and although at least 70% of patients will initially respond to a combination of platinum- and taxane-based therapy, many will develop resistance and eventually progress. Importantly, when singly applied on ovarian xenografts the antibody generated by the present teachings (AR30) induced only moderate effects on tumor growth, but these were comparable or superior to the effect of a clinically approved, blocking antibody to EGFR. While the partial anti-tumor effect of AR30 might be due to an inability to completely block AREG-induced phosphorylation of EGFR, the combination with cisplatin remarkably inhibited growth of ovarian tumors in animals. This observation raises the possibility that anti-AREG antibodies, like anti-EGFR antibodies, might delay the onset of patient resistance to chemotherapy. While this prediction is a matter for future investigation, it is worthwhile noting that AREG expression has been correlated not only with resistance to conventional chemotherapeutic agents, such as doxorubicin and cisplatin, in both liver and breast cancer cells [Chang C. J. et al. (2009) Cellular and molecular life sciences: CMLS 66, 1755-1765]; according to a more recent study AREG associates also with resistance to treatment of hepatocellular carcinoma with sorafenib, a multi-target kinase inhibitor [Blivet-Van Eggelpoel M.-J. et al. (2012) Journal of Hepatology 57, 108-115]. Therefore, AR30 and derivative humanized molecules may serve as therapeutics in cases of AREG-expressing, therapy-resistant tumors of ovarian, liver and other origins.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody comprising an antigen recognition domain which specifically binds amphiregulin and comprises:

(i) complementarity determining regions (CDRs) as set forth in SEQ ID NOs: 4, 6, 8, 18, 20 and 22, wherein said CDRs set forth in SEQ ID NOs: 18, 20 and 22 are arranged in a sequential order from N to C on a light chain of the antibody and said CDRs set forth in SEQ ID NOs: 4, 6 and 8 are arranged in a sequential order from N to C on a heavy chain of said antibody;

(ii) CDRs as set forth in SEQ ID NOs: 32, 34, 36, 48, 50 and 52, wherein said CDRs set forth in SEQ ID NOs:

48, 50 and 52 are arranged in a sequential order from N to C on a light chain of the antibody and said CDRs set forth in SEQ ID NOs: 32, 34 and 36 are arranged in a sequential order from N to C on a heavy chain of said antibody; or (iii) CDRs as set forth in SEQ ID NOs: 64, 66, 68, 94, 95 and 96, wherein said CDRs set forth in SEQ ID NOs: 94, 95 and 96 are arranged in a sequential order from N to C on a light chain of the antibody and said CDRs set forth in SEQ ID NOs: 64, 66 and 68 are arranged in a sequential order from N to C on a heavy chain of the antibody.

2. The antibody of claim 1, wherein the antibody is conjugated to an effector moiety selected from the group consisting of a radioactive compound, a toxin, a chemotherapeutic agent and a label.

3. A composition of matter comprising the antibody of claim 1 and a second antibody.

4. The composition of matter of claim 3, wherein the second antibody binds betacellulin (BTC), epiregulin (EREG), epigen (EPG) and/or neuregulin.

5. An article of manufacture comprising the composition of claim 3 packaged in one container and a chemotherapeutic agent in a second container.

6. A pharmaceutical composition comprising as an active ingredient the antibody of claim 1 and a pharmaceutically acceptable carrier.

7. The antibody of claim 1, being a monoclonal antibody.

8. A composition of matter comprising at least two of antibodies (i) (ii) and (iii) of claim 1.

9. An article of manufacture comprising the composition of claim 8 packaged in one container and a chemotherapeutic agent in a second container.

* * * * *